(12) United States Patent
Allum et al.

(10) Patent No.: US 9,132,250 B2
(45) Date of Patent: Sep. 15, 2015

(54) METHODS, SYSTEMS AND DEVICES FOR NON-INVASIVE VENTILATION INCLUDING A NON-SEALING VENTILATION INTERFACE WITH AN ENTRAINMENT PORT AND/OR PRESSURE FEATURE

(75) Inventors: Todd Allum, Livermore, CA (US); Joey Aguirre, San Ramon, CA (US); Joseph Cipollone, San Ramon, CA (US); Darius Eghbal, Oakland, CA (US); Gregory Kapust, San Ramon, CA (US); Anthony D. Wondka, Thousand Oaks, CA (US)

(73) Assignee: Breathe Technologies, Inc., Irvine, CA (US)

( * ) Notice: Subject to any disclaimer, the term of this patent is extended or adjusted under 35 U.S.C. 154(b) by 978 days.

(21) Appl. No.: 12/876,098

(22) Filed: Sep. 3, 2010
(Under 37 CFR 1.47)

(65) Prior Publication Data

US 2011/0214676 A1    Sep. 8, 2011

Related U.S. Application Data

(63) Continuation-in-part of application No. 12/753,846, filed on Apr. 2, 2010, and a continuation-in-part of application No. 12/753,851, filed on Apr. 2, 2010, and a continuation-in-part of application No. 12/753,853,
(Continued)

(51) Int. Cl.
*A61M 15/08* (2006.01)
*A61M 16/00* (2006.01)

(52) U.S. Cl.
CPC ..................................... *A61M 16/00* (2013.01)

(58) Field of Classification Search
None
See application file for complete search history.

(56) References Cited

U.S. PATENT DOCUMENTS

| 50,641 A | 10/1865 | Stone |
| 428,592 A | 5/1890 | Chapman |

(Continued)

FOREIGN PATENT DOCUMENTS

| CN | 101365508 | 12/2012 |
| DE | 19626924 | 1/1998 |

(Continued)

OTHER PUBLICATIONS

In the U.S. Patent and Trademark Office, Supplemental Notice of Allowance dated in re: U.S. Appl. No. 10/771,803, dated Dec. 2, 2008, 2 pages.

(Continued)

*Primary Examiner* — Tan-Uyen T Ho
*Assistant Examiner* — Eric Bryant
(74) *Attorney, Agent, or Firm* — Stetina Brunda Garred & Brucker

(57) ABSTRACT

Systems and methods may include a gas source, a gas delivery circuit, and a nasal interface allowing breathing ambient air through the nasal interface. A gas flow path through the nasal interface may have a distal gas flow path opening. A nozzle may be associated with a proximal end of the nasal interface a distance from the distal end gas flow path opening. At least a portion of an entrainment port may be between the nozzle and the distal end gas flow opening. The nozzle may deliver gas into the nasal interface to create a negative pressure area in the gas flow path at the entrainment port. The nasal interface and the nozzle may create a positive pressure area between the entrainment port and the distal end gas flow path opening. Gas from the gas delivery source and air entrained

SECTION A-A through the entrainment port may increase airway pressure or lung pressure or provide ventilatory support.

65 Claims, 25 Drawing Sheets

Related U.S. Application Data filed on Apr. 2, 2010, and a continuation-in-part of application No. 12/753,854, filed on Apr. 2, 2010, and a continuation-in-part of application No. 12/753,856, filed on Apr. 2, 2010, and a continuation-in-part of application No. PCT/US2010/029871, filed on Apr. 2, 2010, and a continuation-in-part of application No. PCT/US2010/029873, filed on Apr. 2, 2010, and a continuation-in-part of application No. PCT/US2010/029874, filed on Apr. 2, 2010, and a continuation-in-part of application No. PCT/US2010/029875, filed on Apr. 2, 2010.

(60) Provisional application No. 61/239,728, filed on Sep. 3, 2009, provisional application No. 61/255,760, filed on Oct. 28, 2009, provisional application No. 61/294,363, filed on Jan. 12, 2010, provisional application No. 61/306,370, filed on Feb. 19, 2010.

(56) References Cited

U.S. PATENT DOCUMENTS

| | | |
|---|---|---|
| 697,181 A | 4/1902 | Smith |
| 718,785 A | 1/1903 | McNary |
| 853,439 A | 5/1907 | Clark |
| 859,156 A | 7/1907 | Warnken |
| 909,002 A | 1/1909 | Lambert |
| 1,125,542 A | 1/1915 | Humphries |
| 1,129,619 A | 2/1915 | Zapf |
| 1,331,297 A | 2/1920 | Walker |
| 2,178,800 A | 11/1939 | Lombard |
| 2,259,817 A | 10/1941 | Hawkins |
| 2,552,595 A | 5/1951 | Seeler |
| 2,663,297 A | 12/1953 | Turnberg |
| 2,693,800 A | 11/1954 | Caldwell |
| 2,735,432 A | 2/1956 | Hudson |
| 2,792,000 A | 5/1957 | Richardson |
| 2,843,122 A | 7/1958 | Hudson |
| 2,859,748 A | 11/1958 | Hudson |
| 2,931,358 A | 4/1960 | Sheridan |
| 2,947,938 A | 8/1960 | Bennett |
| 3,172,407 A | 3/1965 | Von Pechmann |
| 3,267,935 A | 8/1966 | Andreasen et al. |
| 3,319,627 A | 5/1967 | Windsor |
| 3,357,424 A | 12/1967 | Schreiber |
| 3,357,427 A | 12/1967 | Wittke et al. |
| 3,357,428 A | 12/1967 | Carlson |
| 3,437,274 A | 4/1969 | Apri |
| 3,460,533 A | 8/1969 | Riú Plá |
| 3,493,703 A | 2/1970 | Finan |
| 3,513,844 A | 5/1970 | Smith |
| 3,610,247 A | 10/1971 | Jackson |
| 3,625,206 A | 12/1971 | Charnley |
| 3,625,207 A | 12/1971 | Agnew |
| 3,631,438 A | 12/1971 | Lewin |
| 3,643,660 A | 2/1972 | Hudson et al. |
| 3,657,740 A | 4/1972 | Cialone |
| 3,682,171 A | 8/1972 | Dali et al. |
| 3,721,233 A | 3/1973 | Montgomery et al. |
| 3,726,275 A | 4/1973 | Jackson et al. |
| 3,727,606 A | 4/1973 | Sielaff |
| 3,733,008 A | 5/1973 | Churchill et al. |
| 3,741,208 A | 6/1973 | Jonsson et al. |
| 3,754,552 A | 8/1973 | King |
| 3,794,026 A | 2/1974 | Jacobs |
| 3,794,072 A | 2/1974 | Diedrich et al. |
| 3,802,431 A | 4/1974 | Farr |
| 3,831,596 A | 8/1974 | Cavallo |
| 3,881,480 A | 5/1975 | Lafourcade |
| 3,896,800 A | 7/1975 | Cibulka |
| 3,903,881 A | 9/1975 | Weigl |
| 3,905,362 A | 9/1975 | Eyrick et al. |
| 3,949,749 A | 4/1976 | Stewart |
| 3,951,143 A | 4/1976 | Kitrilakis et al. |
| 3,961,627 A | 6/1976 | Ernst et al. |
| 3,972,327 A | 8/1976 | Ernst et al. |
| 3,985,131 A | 10/1976 | Buck et al. |
| 3,991,790 A | 11/1976 | Russell |
| 4,003,377 A | 1/1977 | Dahl |
| 4,036,253 A | 7/1977 | Fegan et al. |
| 4,054,133 A | 10/1977 | Myers |
| 4,067,328 A | 1/1978 | Manley |
| 4,106,505 A | 8/1978 | Salter et al. |
| 4,146,885 A | 3/1979 | Lawson, Jr. |
| 4,206,754 A | 6/1980 | Cox et al. |
| 4,211,086 A | 7/1980 | Leonard et al. |
| 4,216,769 A | 8/1980 | Grimes |
| 4,231,363 A | 11/1980 | Grimes |
| 4,231,365 A | 11/1980 | Scarberry |
| 4,256,101 A | 3/1981 | Ellestad |
| 4,261,355 A | 4/1981 | Glazener |
| 4,263,908 A | 4/1981 | Mizerak |
| 4,265,237 A | 5/1981 | Schwanbom et al. |
| 4,266,540 A | 5/1981 | Panzik et al. |
| 4,273,124 A | 6/1981 | Zimmerman |
| 4,274,162 A | 6/1981 | Joy et al. |
| 4,278,082 A | 7/1981 | Blackmer |
| 4,282,869 A | 8/1981 | Zidulka |
| 4,306,567 A | 12/1981 | Krasner |
| 4,323,064 A | 4/1982 | Hoenig et al. |
| 4,354,488 A | 10/1982 | Bartos |
| 4,365,636 A | 12/1982 | Barker |
| 4,367,735 A | 1/1983 | Dali |
| 4,377,162 A | 3/1983 | Staver |
| 4,393,869 A | 7/1983 | Boyarsky et al. |
| 4,406,283 A | 9/1983 | Bir |
| 4,411,267 A | 10/1983 | Heyman |
| 4,413,514 A | 11/1983 | Bowman |
| 4,421,113 A | 12/1983 | Gedeon et al. |
| 4,422,456 A | 12/1983 | Tiep |
| 4,449,523 A | 5/1984 | Szachowicz et al. |
| 4,454,880 A | 6/1984 | Muto et al. |
| 4,462,398 A | 7/1984 | Durkan et al. |
| 4,469,097 A | 9/1984 | Kelman |
| 4,481,944 A | 11/1984 | Bunnell |
| 4,488,548 A | 12/1984 | Agdanowski |
| 4,495,946 A | 1/1985 | Lemer |
| 4,506,666 A | 3/1985 | Durkan |
| 4,506,667 A | 3/1985 | Ansite |
| 4,519,387 A | 5/1985 | Durkan et al. |
| 4,520,812 A | 6/1985 | Freitag et al. |
| 4,527,557 A | 7/1985 | DeVries et al. |
| 4,535,766 A | 8/1985 | Baum |
| 4,537,188 A | 8/1985 | Phuc |
| 4,539,984 A | 9/1985 | Kiszel et al. |
| 4,548,590 A | 10/1985 | Green |
| 4,559,940 A | 12/1985 | McGinnis |
| 4,570,631 A | 2/1986 | Durkan |
| 4,571,741 A | 2/1986 | Guillaumot |
| 4,584,996 A | 4/1986 | Blum |
| 4,590,951 A | 5/1986 | O'Connor |
| 4,592,349 A | 6/1986 | Bird |
| 4,621,632 A | 11/1986 | Bartels et al. |
| 4,630,606 A | 12/1986 | Weerda et al. |
| 4,630,614 A | 12/1986 | Atlas |
| 4,644,947 A | 2/1987 | Whitwam et al. |
| 4,648,395 A | 3/1987 | Sato et al. |
| 4,648,398 A | 3/1987 | Agdanowski et al. |
| 4,658,832 A | 4/1987 | Brugnoli |
| 4,660,555 A | 4/1987 | Payton |
| 4,682,591 A | 7/1987 | Jones |
| 4,684,398 A | 8/1987 | Dunbar et al. |
| 4,686,974 A | 8/1987 | Sato et al. |
| 4,686,975 A | 8/1987 | Naimon et al. |
| 4,688,961 A | 8/1987 | Shioda et al. |
| 4,705,034 A | 11/1987 | Perkins |
| 4,744,356 A | 5/1988 | Greenwood |
| 4,747,403 A | 5/1988 | Gluck et al. |
| 4,753,233 A | 6/1988 | Grimes |
| 4,773,411 A | 9/1988 | Downs |
| 4,776,333 A | 10/1988 | Miyamae |
| 4,782,832 A | 11/1988 | Trimble et al. |
| 4,784,130 A | 11/1988 | Kenyon et al. |

(56) References Cited

U.S. PATENT DOCUMENTS

| | | |
|---|---|---|
| 4,803,981 A | 2/1989 | Vickery |
| 4,807,616 A | 2/1989 | Adahan |
| 4,807,617 A | 2/1989 | Nesti |
| 4,808,160 A | 2/1989 | Timmons et al. |
| 4,813,431 A | 3/1989 | Brown |
| 4,817,897 A | 4/1989 | Kreusel |
| 4,818,320 A | 4/1989 | Weichselbaum |
| 4,823,788 A | 4/1989 | Smith et al. |
| 4,825,859 A | 5/1989 | Lambert |
| 4,827,922 A | 5/1989 | Champain et al. |
| 4,832,014 A | 5/1989 | Perkins |
| 4,838,255 A | 6/1989 | Lambert |
| 4,841,953 A | 6/1989 | Dodrill |
| 4,848,333 A | 7/1989 | Waite |
| 4,850,350 A | 7/1989 | Jackson |
| 4,865,586 A | 9/1989 | Hedberg |
| 4,869,718 A | 9/1989 | Brader |
| 4,899,740 A | 2/1990 | Napolitano |
| 4,905,688 A | 3/1990 | Vicenzi et al. |
| 4,915,103 A | 4/1990 | Visveshwara et al. |
| 4,915,105 A | 4/1990 | Lee |
| 4,919,128 A | 4/1990 | Kopala et al. |
| 4,919,132 A | 4/1990 | Miser |
| 4,938,212 A | 7/1990 | Snook et al. |
| 4,944,310 A | 7/1990 | Sullivan |
| 4,967,743 A | 11/1990 | Lambert |
| 4,971,049 A | 11/1990 | Rotariu et al. |
| 4,982,735 A | 1/1991 | Yagata et al. |
| 4,986,269 A | 1/1991 | Hakkinen |
| 4,989,599 A | 2/1991 | Carter |
| 4,990,157 A | 2/1991 | Roberts et al. |
| 5,000,175 A | 3/1991 | Pue |
| 5,002,050 A | 3/1991 | McGinnis |
| 5,005,570 A | 4/1991 | Perkins |
| 5,018,519 A | 5/1991 | Brown |
| 5,022,394 A | 6/1991 | Chmielinski |
| 5,024,219 A | 6/1991 | Dietz |
| 5,025,805 A | 6/1991 | Nutter |
| 5,038,771 A | 8/1991 | Dietz |
| 5,042,478 A | 8/1991 | Kopala et al. |
| 5,046,491 A | 9/1991 | Derrick |
| 5,046,492 A | 9/1991 | Stackhouse et al. |
| 5,048,515 A | 9/1991 | Sanso |
| 5,048,516 A | 9/1991 | Soderberg |
| 5,052,400 A | 10/1991 | Dietz |
| 5,054,484 A | 10/1991 | Hebeler, Jr. |
| 5,058,580 A | 10/1991 | Hazard |
| 5,074,299 A | 12/1991 | Dietz |
| 5,076,267 A | 12/1991 | Pasternack |
| 5,090,408 A | 2/1992 | Spofford et al. |
| 5,097,827 A | 3/1992 | Izumi |
| 5,099,836 A | 3/1992 | Rowland et al. |
| 5,099,837 A | 3/1992 | Russel, Sr. et al. |
| 5,101,820 A | 4/1992 | Christopher |
| 5,103,815 A | 4/1992 | Siegel et al. |
| 5,105,807 A | 4/1992 | Kahn et al. |
| 5,107,830 A | 4/1992 | Younes |
| 5,107,831 A | 4/1992 | Halpern et al. |
| 5,113,857 A | 5/1992 | Dickerman et al. |
| 5,117,818 A | 6/1992 | Palfy |
| 5,117,819 A | 6/1992 | Servidio et al. |
| 5,127,400 A | 7/1992 | DeVries et al. |
| 5,134,995 A | 8/1992 | Gruenke et al. |
| 5,134,996 A | 8/1992 | Bell |
| 5,140,045 A | 8/1992 | Askanazi et al. |
| 5,148,802 A | 9/1992 | Sanders et al. |
| 5,161,525 A | 11/1992 | Kimm et al. |
| 5,165,397 A | 11/1992 | Arp |
| 5,181,509 A | 1/1993 | Spofford et al. |
| 5,184,610 A | 2/1993 | Marten et al. |
| 5,186,167 A | 2/1993 | Kolobow |
| 5,193,532 A | 3/1993 | Moa et al. |
| 5,193,533 A | 3/1993 | Body et al. |
| 5,199,424 A | 4/1993 | Sullivan et al. |
| 5,211,170 A | 5/1993 | Press |
| 5,217,008 A | 6/1993 | Lindholm |
| 5,233,978 A | 8/1993 | Callaway |
| 5,233,979 A | 8/1993 | Strickland |
| 5,239,994 A | 8/1993 | Atkins |
| 5,239,995 A | 8/1993 | Estes et al. |
| 5,243,972 A | 9/1993 | Huang |
| 5,245,995 A | 9/1993 | Sullivan et al. |
| 5,255,675 A | 10/1993 | Kolobow |
| 5,258,027 A | 11/1993 | Berghaus |
| 5,269,296 A | 12/1993 | Landis |
| 5,271,388 A | 12/1993 | Whitwam et al. |
| 5,271,391 A | 12/1993 | Graves |
| 5,275,159 A | 1/1994 | Griebel |
| 5,279,288 A | 1/1994 | Christopher |
| 5,287,852 A | 2/1994 | Arkinstall |
| 5,303,698 A | 4/1994 | Tobia et al. |
| 5,303,700 A | 4/1994 | Weismann et al. |
| 5,318,019 A | 6/1994 | Celaya |
| 5,331,995 A | 7/1994 | Westfall et al. |
| 5,335,656 A | 8/1994 | Bowe et al. |
| 5,339,809 A | 8/1994 | Beck, Jr. et al. |
| 5,349,946 A | 9/1994 | McComb |
| 5,368,017 A | 11/1994 | Sorenson et al. |
| 5,370,112 A | 12/1994 | Perkins |
| 5,373,842 A | 12/1994 | Olsson et al. |
| 5,375,593 A | 12/1994 | Press |
| 5,388,575 A | 2/1995 | Taube |
| 5,394,870 A | 3/1995 | Johansson |
| 5,398,676 A | 3/1995 | Press et al. |
| 5,398,682 A | 3/1995 | Lynn |
| 5,400,778 A | 3/1995 | Jonson et al. |
| 5,419,314 A | 5/1995 | Christopher |
| 5,438,979 A | 8/1995 | Johnson, Jr. et al. |
| 5,438,980 A | 8/1995 | Phillips |
| 5,443,075 A | 8/1995 | Holscher |
| 5,460,174 A | 10/1995 | Chang |
| 5,460,613 A | 10/1995 | Ulrich et al. |
| 5,474,062 A | 12/1995 | DeVires et al. |
| 5,477,852 A | 12/1995 | Landis et al. |
| 5,485,850 A | 1/1996 | Dietz |
| 5,490,502 A | 2/1996 | Rapoport et al. |
| 5,503,146 A | 4/1996 | Froehlich et al. |
| 5,503,497 A | 4/1996 | Dudley et al. |
| 5,507,282 A | 4/1996 | Younes |
| 5,509,409 A | 4/1996 | Weatherholt |
| 5,513,628 A | 5/1996 | Coles et al. |
| 5,513,631 A | 5/1996 | McWilliams |
| 5,513,635 A | 5/1996 | Bedi |
| 5,522,382 A | 6/1996 | Sullivan et al. |
| 5,526,806 A | 6/1996 | Sansoni |
| 5,529,060 A | 6/1996 | Salmon et al. |
| 5,533,506 A | 7/1996 | Wood |
| 5,535,738 A | 7/1996 | Estes et al. |
| 5,537,997 A | 7/1996 | Mechlenburg et al. |
| 5,538,002 A | 7/1996 | Boussignac et al. |
| 5,542,415 A | 8/1996 | Brody |
| 5,546,935 A | 8/1996 | Champeau |
| 5,549,106 A | 8/1996 | Gruenke et al. |
| 5,551,419 A | 9/1996 | Froehlich et al. |
| 5,558,086 A | 9/1996 | Smith et al. |
| 5,564,416 A | 10/1996 | Jones |
| 5,575,282 A | 11/1996 | Knoch et al. |
| 5,582,164 A | 12/1996 | Sanders |
| 5,593,143 A | 1/1997 | Ferrarin |
| 5,595,174 A | 1/1997 | Gwaltney |
| 5,598,837 A | 2/1997 | Sirianne, Jr. et al. |
| 5,598,840 A | 2/1997 | Iund et al. |
| 5,603,315 A | 2/1997 | Sasso, Jr. |
| 5,605,148 A | 2/1997 | Jones |
| 5,626,131 A | 5/1997 | Chua et al. |
| 5,632,269 A | 5/1997 | Zdrojkowski |
| 5,636,630 A | 6/1997 | Miller et al. |
| 5,645,053 A | 7/1997 | Remmers et al. |
| 5,645,054 A | 7/1997 | Cotner et al. |
| 5,647,351 A | 7/1997 | Weismann et al. |
| 5,669,377 A | 9/1997 | Fenn |
| 5,669,380 A | 9/1997 | Garry et al. |
| 5,676,132 A | 10/1997 | Tillotson et al. |
| 5,676,135 A | 10/1997 | McClean |

(56) References Cited

U.S. PATENT DOCUMENTS

| | | | |
|---|---|---|---|
| 5,682,878 A | 11/1997 | Ogden |
| 5,682,881 A | 11/1997 | Winthrop et al. |
| 5,687,713 A | 11/1997 | Bahr et al. |
| 5,687,714 A | 11/1997 | Kolobow et al. |
| 5,687,715 A | 11/1997 | Landis et al. |
| 5,690,097 A | 11/1997 | Howard et al. |
| 5,692,497 A | 12/1997 | Schnitzer et al. |
| 5,697,364 A | 12/1997 | Chua et al. |
| 5,704,345 A | 1/1998 | Berthon-Jones |
| 5,711,296 A | 1/1998 | Kolobow |
| 5,715,812 A | 2/1998 | Deighan et al. |
| 5,715,815 A | 2/1998 | Lorenzen et al. |
| 5,720,278 A | 2/1998 | Lachmann et al. |
| 5,735,268 A | 4/1998 | Chua et al. |
| 5,735,272 A | 4/1998 | Dillon et al. |
| 5,740,796 A | 4/1998 | Skog |
| 5,752,511 A | 5/1998 | Simmons et al. |
| 5,762,638 A | 6/1998 | Shikani et al. |
| 5,791,337 A | 8/1998 | Coles et al. |
| 5,819,723 A | 10/1998 | Joseph |
| 5,826,579 A | 10/1998 | Remmers et al. |
| 5,845,636 A | 12/1998 | Gruenke et al. |
| 5,865,173 A | 2/1999 | Froehlich |
| 5,865,174 A | 2/1999 | Kloeppel |
| 5,881,723 A | 3/1999 | Wallace et al. |
| 5,904,648 A | 5/1999 | Arndt et al. |
| 5,906,204 A | 5/1999 | Beran et al. |
| 5,911,756 A | 6/1999 | Debry |
| 5,915,379 A | 6/1999 | Wallace et al. |
| 5,915,381 A | 6/1999 | Nord |
| 5,918,597 A | 7/1999 | Jones et al. |
| 5,921,238 A | 7/1999 | Bourdon |
| 5,921,942 A | 7/1999 | Remmers et al. |
| 5,921,952 A | 7/1999 | Desmond, III et al. |
| 5,927,276 A | 7/1999 | Rodriguez |
| 5,928,189 A | 7/1999 | Phillips et al. |
| 5,931,160 A | 8/1999 | Gilmore et al. |
| 5,931,162 A | 8/1999 | Christian |
| 5,937,853 A | 8/1999 | Strom |
| 5,937,855 A | 8/1999 | Zdrojkowski et al. |
| 5,938,118 A | 8/1999 | Cooper |
| 5,954,050 A | 9/1999 | Christopher |
| 5,957,136 A | 9/1999 | Magidson et al. |
| 5,964,223 A | 10/1999 | Baran |
| 5,975,077 A | 11/1999 | Hofstetter et al. |
| 5,975,081 A | 11/1999 | Hood et al. |
| 5,979,440 A | 11/1999 | Honkonen et al. |
| 5,989,193 A | 11/1999 | Sullivan |
| 6,000,396 A | 12/1999 | Melker et al. |
| 6,019,101 A | 2/2000 | Cotner et al. |
| 6,039,696 A | 3/2000 | Bell |
| 6,050,260 A | 4/2000 | Daniell et al. |
| 6,076,519 A | 6/2000 | Johnson |
| 6,085,747 A | 7/2000 | Axe et al. |
| 6,091,973 A | 7/2000 | Colla et al. |
| 6,093,169 A | 7/2000 | Cardoso |
| 6,105,575 A | 8/2000 | Estes et al. |
| 6,109,264 A | 8/2000 | Sauer |
| 6,112,746 A | 9/2000 | Kwok et al. |
| 6,119,694 A | 9/2000 | Correa et al. |
| 6,120,460 A | 9/2000 | Abreu |
| 6,123,668 A | 9/2000 | Abreu |
| 6,131,571 A | 10/2000 | Lampotang et al. |
| 6,135,970 A | 10/2000 | Kadhiresan et al. |
| 6,152,132 A | 11/2000 | Psaros |
| 6,152,134 A | 11/2000 | Webber et al. |
| 6,158,432 A | 12/2000 | Biondi et al. |
| 6,192,883 B1 | 2/2001 | Miller, Jr. |
| 6,203,502 B1 | 3/2001 | Hilgendorf et al. |
| 6,213,119 B1 | 4/2001 | Brydon et al. |
| 6,213,955 B1 | 4/2001 | Karakasoglu et al. |
| 6,220,244 B1 | 4/2001 | McLaughlin |
| 6,224,560 B1 | 5/2001 | Gazula et al. |
| 6,227,200 B1 | 5/2001 | Crump et al. |
| 6,247,470 B1 | 6/2001 | Ketchedjian |
| 6,269,811 B1 | 8/2001 | Duff et al. |
| 6,269,812 B1 | 8/2001 | Wallace et al. |
| 6,273,859 B1 | 8/2001 | Remmers et al. |
| 6,286,508 B1 | 9/2001 | Remmers et al. |
| D449,376 S | 10/2001 | McDonald et al. |
| D449,883 S | 10/2001 | McDonald et al. |
| 6,298,850 B1 | 10/2001 | Argraves |
| 6,305,374 B1 | 10/2001 | Zdrojkowski et al. |
| 6,314,957 B1 | 11/2001 | Boissin et al. |
| 6,315,739 B1 | 11/2001 | Merilainen et al. |
| D451,598 S | 12/2001 | McDonald et al. |
| 6,328,038 B1 | 12/2001 | Kessler et al. |
| 6,328,753 B1 | 12/2001 | Zammit |
| 6,332,463 B1 | 12/2001 | Farrugia et al. |
| 6,345,619 B1 | 2/2002 | Finn |
| 6,357,438 B1 | 3/2002 | Hansen |
| 6,357,440 B1 | 3/2002 | Hansen et al. |
| 6,360,741 B2 | 3/2002 | Truschel |
| 6,360,745 B1 | 3/2002 | Wallace et al. |
| 6,363,933 B1 | 4/2002 | Berthon-Jones |
| 6,367,474 B1 | 4/2002 | Berthon-Jones et al. |
| 6,369,838 B1 | 4/2002 | Wallace et al. |
| 6,371,114 B1 | 4/2002 | Schmidt et al. |
| 6,378,520 B1 | 4/2002 | Davenport |
| 6,390,091 B1 | 5/2002 | Banner et al. |
| 6,394,088 B1 | 5/2002 | Frye et al. |
| 6,398,739 B1 | 6/2002 | Sullivan et al. |
| 6,418,928 B1 | 7/2002 | Bordewick et al. |
| 6,419,476 B1 * | 7/2002 | Ouellette ..................... 425/567 |
| 6,422,240 B1 | 7/2002 | Levitsky et al. |
| 6,423,001 B1 | 7/2002 | Abreu |
| 6,427,690 B1 | 8/2002 | McCombs et al. |
| 6,431,172 B1 | 8/2002 | Bordewick |
| 6,439,228 B1 | 8/2002 | Hete et al. |
| 6,439,229 B1 | 8/2002 | Du et al. |
| 6,439,234 B1 | 8/2002 | Curti et al. |
| 6,439,235 B1 | 8/2002 | Larquet et al. |
| 6,450,164 B1 | 9/2002 | Banner et al. |
| 6,450,166 B1 | 9/2002 | McDonald et al. |
| 6,457,472 B1 | 10/2002 | Schwartz et al. |
| 6,467,477 B1 | 10/2002 | Frank et al. |
| 6,478,026 B1 | 11/2002 | Wood |
| 6,494,202 B2 | 12/2002 | Farmer |
| 6,494,206 B1 | 12/2002 | Bergamaschi et al. |
| 6,505,623 B1 | 1/2003 | Hansen |
| 6,505,624 B1 | 1/2003 | Campbell, Sr. |
| 6,516,801 B2 | 2/2003 | Boussignac |
| 6,520,176 B1 | 2/2003 | Dubois et al. |
| 6,520,183 B2 | 2/2003 | Amar |
| 6,530,373 B1 | 3/2003 | Patron et al. |
| 6,532,958 B1 | 3/2003 | Buan et al. |
| 6,532,960 B1 | 3/2003 | Yurko |
| 6,536,432 B2 | 3/2003 | Truschel |
| 6,536,436 B1 | 3/2003 | McGlothen |
| 6,550,478 B2 | 4/2003 | Remmers et al. |
| 6,553,992 B1 | 4/2003 | Berthon-Jones et al. |
| 6,561,188 B1 | 5/2003 | Ellis |
| 6,561,193 B1 | 5/2003 | Noble |
| 6,564,797 B1 | 5/2003 | Mechlenburg et al. |
| 6,564,800 B1 | 5/2003 | Olivares |
| 6,568,391 B1 | 5/2003 | Tatarek et al. |
| 6,571,794 B1 | 6/2003 | Hansen |
| 6,571,796 B2 | 6/2003 | Banner et al. |
| 6,571,798 B1 | 6/2003 | Thornton |
| 6,575,159 B1 | 6/2003 | Frye et al. |
| 6,575,944 B1 | 6/2003 | McNary et al. |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,591,834 B1 | 7/2003 | Colla et al. |
| 6,591,835 B1 | 7/2003 | Blanch |
| 6,595,207 B1 | 7/2003 | McDonald et al. |
| 6,595,215 B2 | 7/2003 | Wood |
| 6,609,517 B1 | 8/2003 | Estes et al. |
| 6,622,726 B1 | 9/2003 | Du |
| 6,626,174 B1 | 9/2003 | Genger et al. |
| 6,626,175 B2 | 9/2003 | Jafari et al. |
| 6,629,525 B2 | 10/2003 | Hill et al. |
| 6,629,527 B1 | 10/2003 | Estes et al. |

(56) References Cited

U.S. PATENT DOCUMENTS

| | | |
|---|---|---|
| 6,629,529 B2 | 10/2003 | Arnott |
| 6,631,919 B1 | 10/2003 | West et al. |
| 6,634,356 B1 | 10/2003 | O'Dea et al. |
| 6,635,021 B1 | 10/2003 | Sullivan et al. |
| 6,640,806 B2 | 11/2003 | Yurko |
| 6,644,305 B2 | 11/2003 | MacRae et al. |
| 6,644,311 B1 | 11/2003 | Truitt et al. |
| 6,644,315 B2 | 11/2003 | Ziaee |
| 6,651,653 B1 | 11/2003 | Honkonen et al. |
| 6,651,656 B2 | 11/2003 | Demers et al. |
| 6,651,658 B1 | 11/2003 | Hill et al. |
| 6,655,382 B1 | 12/2003 | Kolobow |
| 6,655,385 B1 | 12/2003 | Curti et al. |
| 6,666,208 B1 | 12/2003 | Schumacher et al. |
| 6,668,828 B1 | 12/2003 | Figley et al. |
| 6,668,829 B2 | 12/2003 | Biondi et al. |
| 6,669,712 B1 | 12/2003 | Cardoso |
| 6,675,796 B2 | 1/2004 | McDonald |
| 6,675,801 B2 | 1/2004 | Wallace et al. |
| 6,679,265 B2 | 1/2004 | Strickland et al. |
| 6,681,764 B1 | 1/2004 | Honkonen et al. |
| 6,684,883 B1 | 2/2004 | Burns |
| 6,691,702 B2 | 2/2004 | Appel et al. |
| 6,691,707 B1 | 2/2004 | Gunaratnam et al. |
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |
| 6,722,360 B2 | 4/2004 | Doshi |
| 6,722,362 B2 | 4/2004 | Hete et al. |
| 6,742,517 B1 | 6/2004 | Frye et al. |
| 6,745,768 B2 | 6/2004 | Colla et al. |
| 6,752,150 B1 | 6/2004 | Remmers et al. |
| 6,752,151 B2 | 6/2004 | Hill |
| 6,752,152 B2 | 6/2004 | Gale et al. |
| 6,755,193 B2 | 6/2004 | Berthon-Jones et al. |
| 6,758,217 B1 | 7/2004 | Younes |
| 6,761,172 B2 | 7/2004 | Boussignac et al. |
| 6,763,832 B1 | 7/2004 | Kirsch et al. |
| 6,769,432 B1 | 8/2004 | Keifer |
| 6,776,162 B2 | 8/2004 | Wood |
| 6,776,163 B2 | 8/2004 | Dougill et al. |
| 6,789,539 B2 | 9/2004 | Martinez |
| 6,796,305 B1 | 9/2004 | Banner et al. |
| 6,799,575 B1 | 10/2004 | Carter |
| 6,805,126 B2 | 10/2004 | Dutkiewicz |
| 6,807,966 B2 | 10/2004 | Wright |
| 6,807,967 B2 | 10/2004 | Wood |
| 6,810,876 B2 | 11/2004 | Berthon-Jones |
| 6,814,073 B2 | 11/2004 | Wickham |
| 6,814,077 B1 | 11/2004 | Eistert |
| 6,823,866 B2 | 11/2004 | Jafari et al. |
| 6,827,340 B2 | 12/2004 | Austin et al. |
| 6,837,238 B2 | 1/2005 | McDonald |
| 6,840,240 B1 | 1/2005 | Berthon-Jones et al. |
| 6,843,247 B2 | 1/2005 | Frye et al. |
| 6,848,446 B2 | 2/2005 | Noble |
| 6,854,462 B2 | 2/2005 | Berthon-Jones et al. |
| 6,863,069 B2 | 3/2005 | Wood |
| 6,866,041 B2 | 3/2005 | Hardy, Jr. et al. |
| 6,877,511 B2 | 4/2005 | DeVries et al. |
| 6,880,556 B2 | 4/2005 | Uchiyama et al. |
| 6,910,480 B1 | 6/2005 | Berthon-Jones |
| 6,910,482 B2 | 6/2005 | Bliss et al. |
| 6,910,510 B2 | 6/2005 | Gale et al. |
| 6,913,601 B2 | 7/2005 | St. Goar et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,938,620 B2 | 9/2005 | Payne, Jr. |
| 6,941,950 B2 | 9/2005 | Wilson et al. |
| 6,948,497 B2 | 9/2005 | Zdrojkowski et al. |
| 6,951,217 B2 | 10/2005 | Berthon-Jones |
| 6,971,382 B1 | 12/2005 | Corso |
| 6,986,353 B2 | 1/2006 | Wright |
| 6,994,089 B2 | 2/2006 | Wood |
| 6,997,177 B2 | 2/2006 | Wood |
| 6,997,881 B2 | 2/2006 | Green et al. |
| 7,000,612 B2 | 2/2006 | Jafari et al. |
| 7,004,170 B1 | 2/2006 | Gillstrom |
| 7,007,692 B2 | 3/2006 | Aylsworth et al. |
| 7,011,091 B2 | 3/2006 | Hill et al. |
| 7,013,892 B2 | 3/2006 | Estes et al. |
| 7,013,898 B2 | 3/2006 | Rashad et al. |
| 7,017,574 B2 | 3/2006 | Biondi et al. |
| 7,017,575 B2 | 3/2006 | Yagi et al. |
| 7,024,945 B2 | 4/2006 | Wallace |
| 7,036,504 B2 | 5/2006 | Wallace et al. |
| 7,044,129 B1 | 5/2006 | Truschel et al. |
| 7,047,969 B2 | 5/2006 | Noble |
| 7,047,974 B2 | 5/2006 | Strickland et al. |
| 7,051,735 B2 | 5/2006 | Mechlenburg et al. |
| 7,055,522 B2 | 6/2006 | Berthon-Jones |
| 7,059,328 B2 | 6/2006 | Wood |
| 7,066,173 B2 | 6/2006 | Banner et al. |
| 7,066,178 B2 | 6/2006 | Gunaratnam et al. |
| 7,077,132 B2 | 7/2006 | Berthon-Jones |
| 7,077,133 B2 | 7/2006 | Yagi et al. |
| 7,080,645 B2 | 7/2006 | Genger et al. |
| 7,080,646 B2 | 7/2006 | Wiesmann et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,121,277 B2 | 10/2006 | Strom |
| 7,128,578 B2 | 10/2006 | Lampotang et al. |
| 7,152,598 B2 | 12/2006 | Morris et al. |
| 7,152,604 B2 | 12/2006 | Hickle et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,188,621 B2 | 3/2007 | DeVries et al. |
| 7,188,624 B2 | 3/2007 | Wood |
| 7,195,016 B2 | 3/2007 | Loyd et al. |
| 7,195,018 B1 | 3/2007 | Goldstein |
| 7,201,169 B2 | 4/2007 | Wilkie et al. |
| 7,201,269 B2 | 4/2007 | Buscher et al. |
| D542,912 S | 5/2007 | Gunaratnam et al. |
| 7,222,623 B2 | 5/2007 | DeVries et al. |
| 7,225,811 B2 | 6/2007 | Ruiz et al. |
| 7,234,465 B2 | 6/2007 | Wood |
| 7,237,205 B2 | 6/2007 | Sarel |
| 7,246,620 B2 | 7/2007 | Conroy, Jr. |
| D549,323 S | 8/2007 | Kwok et al. |
| 7,255,103 B2 | 8/2007 | Bassin |
| 7,255,107 B1 | 8/2007 | Gomez |
| 7,267,122 B2 | 9/2007 | Hill |
| 7,267,123 B2 | 9/2007 | Aylsworth et al. |
| 7,270,126 B2 | 9/2007 | Wallace et al. |
| 7,270,128 B2 | 9/2007 | Berthon-Jones et al. |
| 7,296,569 B2 | 11/2007 | Frye et al. |
| 7,296,573 B2 | 11/2007 | Estes et al. |
| D557,802 S | 12/2007 | Miceli, Jr. et al. |
| 7,302,950 B2 | 12/2007 | Berthon-Jones et al. |
| 7,305,987 B2 | 12/2007 | Scholler et al. |
| 7,318,437 B2 | 1/2008 | Gunaratnam et al. |
| 7,320,321 B2 | 1/2008 | Pranger et al. |
| 7,328,703 B1 | 2/2008 | Tiep |
| 7,353,826 B2 | 4/2008 | Sleeper et al. |
| 7,367,337 B2 | 5/2008 | Berthon-Jones et al. |
| 7,370,652 B2 | 5/2008 | Matula, Jr. et al. |
| 7,373,939 B1 | 5/2008 | DuBois et al. |
| 7,406,966 B2 | 8/2008 | Wondka |
| 7,418,965 B2 | 9/2008 | Fukunaga et al. |
| 7,422,015 B2 | 9/2008 | Delisle et al. |
| 7,431,035 B2 | 10/2008 | Mizuta et al. |
| 7,451,762 B2 | 11/2008 | Chua et al. |
| 7,455,717 B2 | 11/2008 | Sprinkle |
| 7,461,656 B2 | 12/2008 | Gunaratnam et al. |
| 7,468,040 B2 | 12/2008 | Hartley et al. |

(56) References Cited

U.S. PATENT DOCUMENTS

| | | |
|---|---|---|
| 7,469,697 B2 | 12/2008 | Lee et al. |
| 7,472,702 B2 | 1/2009 | Beck et al. |
| 7,478,641 B2 | 1/2009 | Rousselet |
| 7,481,219 B2 | 1/2009 | Lewis et al. |
| 7,481,221 B2 | 1/2009 | Kullik et al. |
| 7,487,774 B2 | 2/2009 | Acker |
| 7,487,778 B2 | 2/2009 | Freitag |
| 7,490,605 B2 | 2/2009 | Frye et al. |
| D588,258 S | 3/2009 | Judson et al. |
| D589,139 S | 3/2009 | Guney et al. |
| 7,500,482 B2 | 3/2009 | Biederman |
| 7,509,957 B2 | 3/2009 | Duquette et al. |
| D591,419 S | 4/2009 | Chandran et al. |
| 7,533,670 B1 | 5/2009 | Freitag et al. |
| 7,556,038 B2 | 7/2009 | Kirby et al. |
| 7,559,327 B2 | 7/2009 | Hernandez |
| 7,562,657 B2 | 7/2009 | Blanch et al. |
| 7,562,659 B2 | 7/2009 | Matarasso |
| 7,578,294 B2 | 8/2009 | Pierro et al. |
| 7,588,033 B2 | 9/2009 | Wondka |
| 7,591,265 B2 | 9/2009 | Lee et al. |
| 7,631,642 B2 | 12/2009 | Freitag et al. |
| 7,640,934 B2 | 1/2010 | Zollinger et al. |
| 7,658,189 B2 | 2/2010 | Davidson et al. |
| D614,288 S | 4/2010 | Judson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 | 9/2011 | Christopher et al. |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0112730 A1 | 8/2002 | Dutkiewicz |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0020493 A1 | 2/2004 | Wood |
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0159323 A1 | 8/2004 | Schmidt et al. |
| 2004/0206352 A1 | 10/2004 | Conroy |
| 2004/0221848 A1 | 11/2004 | Hill |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |
| 2005/0034724 A1 | 2/2005 | O'Dea |
| 2005/0061322 A1 | 3/2005 | Freitag |

(56) References Cited

U.S. PATENT DOCUMENTS

| | | |
|---|---|---|
| 2005/0061326 A1 | 3/2005 | Payne |
| 2005/0072430 A1 | 4/2005 | Djupesland |
| 2005/0081849 A1 | 4/2005 | Warren |
| 2005/0087190 A1 | 4/2005 | Jafari et al. |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0247308 A1 | 11/2005 | Frye et al. |
| 2005/0257793 A1 | 11/2005 | Tatsumoto |
| 2005/0274381 A1 | 12/2005 | Deane et al. |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |
| 2006/0070625 A1 | 4/2006 | Ayappa et al. |
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0124131 A1 | 6/2006 | Chandran et al. |
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1* | 8/2006 | Matarasso ............... 128/204.18 |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Iobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1* | 4/2007 | Duquette et al. ......... 128/204.18 |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0163600 A1 | 7/2007 | Hoffman |
| 2007/0173705 A1 | 7/2007 | Teller et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272249 A1 | 11/2007 | Chandran et al. |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunaratnam et al. |
| 2008/0092905 A1 | 4/2008 | Gunaratnam et al. |
| 2008/0092906 A1 | 4/2008 | Gunaratnam et al. |
| 2008/0099024 A1 | 5/2008 | Gunaratnam et al. |
| 2008/0099027 A1 | 5/2008 | Gunaratnam et al. |
| 2008/0105264 A1 | 5/2008 | Gunaratnam et al. |
| 2008/0110462 A1 | 5/2008 | Chekal et al. |
| 2008/0121230 A1 | 5/2008 | Cortez et al. |
| 2008/0135044 A1 | 6/2008 | Freitag et al. |
| 2008/0142019 A1* | 6/2008 | Lewis et al. ............... 128/207.18 |
| 2008/0161653 A1 | 7/2008 | Lin et al. |
| 2008/0173304 A1 | 7/2008 | Zaiser et al. |
| 2008/0178874 A1* | 7/2008 | Doshi et al. ............... 128/200.24 |
| 2008/0178880 A1 | 7/2008 | Christopher et al. |
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |
| 2008/0223369 A1 | 9/2008 | Warren |
| 2008/0245368 A1* | 10/2008 | Dunsmore et al. ......... 128/205.24 |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0078255 A1 | 3/2009 | Bowman et al. |
| 2009/0078258 A1 | 3/2009 | Bowman et al. |
| 2009/0095298 A1 | 4/2009 | Gunaratnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151719 A1 | 6/2009 | Wondka et al. |
| 2009/0151724 A1 | 6/2009 | Wondka et al. |
| 2009/0151726 A1 | 6/2009 | Freitag |
| 2009/0151729 A1 | 6/2009 | Judson et al. |
| 2009/0156953 A1 | 6/2009 | Wondka et al. |
| 2009/0165799 A1 | 7/2009 | Duquette et al. |
| 2009/0173347 A1 | 7/2009 | Berthon-Jones |

(56) References Cited

U.S. PATENT DOCUMENTS

| | | |
|---|---|---|
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0241947 A1 | 10/2009 | Bedini et al. |
| 2009/0241951 A1 | 10/2009 | Jafari et al. |
| 2009/0250066 A1 | 10/2009 | Daly |
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293873 A1 * | 12/2009 | Djupesland et al. ..... 128/203.15 |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0043786 A1 | 2/2010 | Freitag et al. |
| 2010/0071693 A1 | 3/2010 | Allum et al. |
| 2010/0071697 A1 | 3/2010 | Jafari et al. |
| 2010/0083968 A1 | 4/2010 | Wondka et al. |
| 2010/0108073 A1 | 5/2010 | Zollinger et al. |
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |
| 2010/0224196 A1 | 9/2010 | Jablons |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0252044 A1 | 10/2010 | Duquette et al. |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Seiver et al. |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunaratnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0114098 A1 | 5/2011 | McAuley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0162655 A1 | 7/2011 | Gunaratnam et al. |
| 2011/0178419 A1 | 7/2011 | Wood et al. |
| 2011/0180068 A1 | 7/2011 | Kenyon et al. |
| 2011/0197885 A1 | 8/2011 | Wondka et al. |
| 2011/0209705 A1 | 9/2011 | Freitag |
| 2011/0220105 A1 | 9/2011 | Meier |
| 2011/0232642 A1 | 9/2011 | Bliss et al. |
| 2011/0247625 A1 | 10/2011 | Boussignac |
| 2011/0253147 A1 | 10/2011 | Gusky et al. |
| 2011/0259327 A1 | 10/2011 | Wondka et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |

FOREIGN PATENT DOCUMENTS

| | | | |
|---|---|---|---|
| DE | 29902267 U1 | 7/1999 | |
| DE | 19841070 | 5/2000 | |
| DE | 19849571 | 5/2000 | |
| DE | 10337138.9 | 3/2005 | |
| DE | 10 2006 023 637.8 | 11/2007 | |
| EP | 0125424 | 11/1984 | |
| EP | 0692273 | 1/1996 | |
| EP | 0778035 | 6/1997 | |
| EP | 1359961 | 11/2003 | |
| EP | 2377462 | 11/2010 | |
| GB | 2174609 | 11/1986 | |
| GB | 2201098 | 8/1988 | |
| GB | 1055148 | 6/1989 | |
| GB | 2338420 | 12/1999 | |
| JP | 4502117 | 4/1992 | |
| JP | S63-57060 | 3/1998 | |
| JP | 2002-204830 | 7/2002 | |
| JP | 2005517505 | 6/2005 | |
| JP | 2007125408 | 5/2007 | |
| JP | 2007518451 | 7/2007 | |
| JP | 2007229207 | 9/2007 | |
| JP | 2007527271 | 9/2007 | |
| JP | 2009519759 | 5/2009 | |
| JP | 2009520514 | 5/2009 | |
| JP | 2009523055 | 6/2009 | |
| WO | WO90/06149 | * 6/1990 | ............ A61M 16/00 |
| WO | WO9006149 | 6/1990 | |
| WO | WO-92/11054 | 7/1992 | |
| WO | WO-98/01176 | 1/1998 | |
| WO | WO-99/04841 | 2/1999 | |
| WO | WO-00/64521 | 11/2000 | |
| WO | WO-01/76655 | 10/2001 | |
| WO | WO-02/062413 | 8/2002 | |
| WO | WO02096342 | 12/2002 | |
| WO | WO03068301 | 8/2003 | |
| WO | WO03070306 | 8/2003 | |
| WO | WO-2004/009169 | 1/2004 | |
| WO | WO2005007056 | 1/2005 | |
| WO | WO-2005/014091 | 2/2005 | |
| WO | WO2005010608 | 2/2005 | |
| WO | WO2005011556 | 2/2005 | |
| WO | WO-2005/018524 | 3/2005 | |
| WO | WO-2006/138580 | 12/2006 | |
| WO | WO-2007/035804 | 3/2007 | |
| WO | WO2007064668 | 6/2007 | |
| WO | WO2007081801 | 7/2007 | |
| WO | WO-2007/139531 | 12/2007 | |
| WO | WO-2007142812 | 12/2007 | |
| WO | WO-2008/014543 | 2/2008 | |
| WO | WO-2008/019102 | 2/2008 | |
| WO | WO-2008/052534 | 5/2008 | |
| WO | WO2008060295 | 5/2008 | |
| WO | WO-2008/112474 | 9/2008 | |
| WO | WO-2008/138040 | 11/2008 | |
| WO | WO-2008/144589 | 11/2008 | |
| WO | WO-2008/144669 | 11/2008 | |
| WO | WO-2009/042973 | 4/2009 | |

(56) References Cited

FOREIGN PATENT DOCUMENTS

| WO | WO-2009/042974 | 4/2009 |
| WO | WO-2009/059353 | 5/2009 |
| WO | WO-2009/064202 | 5/2009 |
| WO | WO-2009/074160 | 6/2009 |
| WO | WO-2009/082295 | 7/2009 |
| WO | WO-2009/087607 | 7/2009 |
| WO | WO-2009/092057 | 7/2009 |
| WO | WO-2009/103288 | 8/2009 |
| WO | WO-2009/109005 | 9/2009 |
| WO | WO-2009/115944 | 9/2009 |
| WO | WO-2009/115948 | 9/2009 |
| WO | WO 2009/115949 | 9/2009 |
| WO | WO-2009/129506 | 10/2009 |
| WO | WO-2009/136101 | 11/2009 |
| WO | WO-2009/139647 | 11/2009 |
| WO | WO-2009/149351 | 12/2009 |
| WO | WO-2009/149353 | 12/2009 |
| WO | WO 2009/149355 | 12/2009 |
| WO | WO 2009/149357 | 12/2009 |
| WO | WO-2009/151344 | 12/2009 |
| WO | WO 2009/151791 | 12/2009 |
| WO | WO-2010/000135 | 1/2010 |
| WO | WO 2010/021556 | 2/2010 |
| WO | WO 2010/022363 | 2/2010 |
| WO | WO 2010/039989 | 4/2010 |
| WO | WO 2010/041966 | 4/2010 |
| WO | WO 2010/044034 | 4/2010 |
| WO | WO-2010/057268 | 5/2010 |
| WO | WO-2010/059049 | 5/2010 |
| WO | WO-2010/060422 | 6/2010 |
| WO | WO-2010/068356 | 6/2010 |
| WO | WO 2010/070493 | 6/2010 |
| WO | WO 2010/070497 | 6/2010 |
| WO | WO 2010/070498 | 6/2010 |
| WO | WO 2010/076711 | 7/2010 |
| WO | WO-2010/081223 | 7/2010 |
| WO | WO-2010/091157 | 8/2010 |
| WO | WO 2010/099375 | 9/2010 |
| WO | WO-2010/102094 | 9/2010 |
| WO | WO 2010/115166 | 10/2010 |
| WO | WO 2010/115168 | 10/2010 |
| WO | WO 2010/115169 | 10/2010 |
| WO | WO 2010/115170 | 10/2010 |
| WO | WO 2010/116275 | 10/2010 |
| WO | WO-2010/132853 | 11/2010 |
| WO | WO-2010/136923 | 12/2010 |
| WO | WO-2010/139014 | 12/2010 |
| WO | WO-2010/150187 | 12/2010 |
| WO | WO 2011/002608 | 1/2011 |
| WO | WO 2011/004274 | 1/2011 |
| WO | WO-2011/006184 | 1/2011 |
| WO | WO-2011/006199 | 1/2011 |
| WO | WO-2011/014931 | 2/2011 |
| WO | WO-2011/017033 | 2/2011 |
| WO | WO-2011/017738 | 2/2011 |
| WO | WO-2011/021978 | 2/2011 |
| WO | WO-2011/022779 | 3/2011 |
| WO | WO-2011/024383 | 3/2011 |
| WO | WO 2011/029073 | 3/2011 |
| WO | WO 2011/029074 | 3/2011 |
| WO | WO-2011/035373 | 3/2011 |
| WO | WO-2011/038950 | 4/2011 |
| WO | WO-2011/038951 | 4/2011 |
| WO | WO-2011/044627 | 4/2011 |
| WO | WO-2011/057362 | 5/2011 |
| WO | WO 2011/059346 | 5/2011 |
| WO | WO-2011/061648 | 5/2011 |
| WO | WO-2011/062510 | 5/2011 |
| WO | WO-2011/086437 | 7/2011 |
| WO | WO-2011/086438 | 7/2011 |
| WO | WO 2011/112807 | 9/2011 |

OTHER PUBLICATIONS

In the U.S. Patent and Trademark Office, Supplemental Notice of Allowance dated in re: U.S. Appl. No. 10/771,803, dated Nov. 7, 2008, 2 pages.
In the U.S. Patent and Trademark Office, Examiner's Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiner's Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14, 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Restriction Requirement in re: U.S. Appl. No. 12/754,437, dated Aug. 16, 2011, 5 pages.
In the U.S. Patent and Trademark Office, Non-Final Office Action dated in re: U.S. Appl. No. 10/567,746, dated Oct. 5, 2009, 9 pages.
In the U.S. Patent and Trademark Office, Notice of Allowance and Examiner's Interview Summary in re: U.S. Appl. No. 11/523,519, dated Jan. 16, 2009, 10 pages.
In the U.S. Patent and Trademark Office, Examiner's Interview Summary in re: U.S. Appl. No. 11/523,519, dated Jan. 13, 2009, 4 pages.
In the U.S. Patent and Trademark Office, Final Office Action in re: U.S. Appl. No. 11/523,519, dated Jul. 11, 2008, 13 pages.
In the U.S. Patent and Trademark Office, Examiner's Interview Summary in re: U.S. Appl. No. 11/523,519, dated Apr. 10, 2008, 3 pages.
In the U.S. Patent and Trademark Office, Final Office Action in re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.
In the U.S. Patent and Trademark Office, Supplemental Notice of Allowance in re: U.S. Appl. No. 11/798,965, dated Aug. 21, 2009, 4 pages.
In the U.S. Patent and Trademark Office, Notice of Allowance in re: U.S. Appl. No. 11/798,965, dated Jul. 17, 2009, 5 pages.
In the U.S. Patent and Trademark Office, Final Office Action in re: U.S. Appl. No. 11/798,965, dated Apr. 9, 2009, 6 pages.
In the U.S. Patent and Tademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.
In the U.S. Patent and Trademark Office, Examiner's Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/493,677, dated Aug. 5, 2011, 5 pages.
In the U.S. Patent and Trademark Office, Restriction/Election Requirement in re: U.S. Appl. No. 12/153,423, dated Oct. 6, 2011, 8 pages.
In the U.S. Patent and Trademark Office, Notice of Allowance in re: U.S. Appl. No. 10/922,054, dated Feb. 12, 2008, 6 pages.
In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.

(56) References Cited

OTHER PUBLICATIONS

In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiners Interview Summary in re: U.S. Appl. No. 12/076,062, dated Nov. 2, 2011, 8 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, Ex Parte Quayle Office Action in re: U.S. Appl. No. 29/388,700, dated Oct. 7, 2011, 5 pages.
"AARC Clinical Practice Guideline: Oxygen Therapy in the Home or Extended Care Facility," *Resp. Care*, 1992: 37(8), pp. 918-922.
"ATS Statement: Guidelines for the Six-Minute Walk Test," *Am. J. Respir. Crit. Care Med.*, 2002: 166, pp. 111-117.
"Passy-Muir Speaking Valves," *Respiratory*, Nov. 13, 1998, 7 pages.
Ambrosino, "Exercise and noninvasive ventilatory support," *Monaldi Arch Chest Dis.*, 2000: 55(3): 242-246.
Ambrosino, "Weaning and Respiratory Muscle Dysfunction: The Egg Chicken Dilemma," *Chest*, 2005: 128(2), pp. 481-483.
Bach et al., "Intermittent Positive Pressure Ventilation via Nasal Access in the Management of Respiratory Insufficiency," *Chest*, 1987: 92(1), pp. 168-170.
Banner et al., "Extubating at a Pressure Support Ventilation Level Corresponding to Zero Imposed Work of Breathing," *Anesthesiology*, Sep. 1994: 81(3A), p. A271.
Banner et al., "Imposed Work of Breathing and Methods of Triggering a Demand-Flow, Continuous Positive Airway Pressure System," *Critical Care Medicine*, 1993: 21(2), pp. 183-190.
Banner et al., "Site of Pressure Measurement During Spontaneous Breathing with Continuous Positive Airway Pressure: Effect on Calculating Imposed Work of Breathing," *Critical Care Medicine*, 1992: 20(4), pp. 528-533.
Barakat et al., "Effect of noninvasive ventilatory support during exercise of a program in pulmonary rehabilitation in patients with COPD," *Int. J. Chron. Obstruct. Pulmon. Dis.*, 2007: 2(4), pp. 585-591.
Barreiro et al., "Noninvasive ventilation," *Crit Care Clin.*, 2007; 23(2): 201-22.
Bauer et al., "ADAM Nasal CPAP Circuit Adaptation: A Case Report," *Sleep*, 1991: 14(3), pp. 272-273.
Blanch, "Clinical Studies of Tracheal Gas Insufflation," *Resp. Care*, 2001: 45(2), pp. 158-166.
Borghi-Silva et al., "Non-invasive ventilation improves peripheral oxygen saturation and reduces fatigability of quadriceps in patients with COPD," Respirology, 2009, 14:537-546.
Bossi et al., "Continuous Positive Airway Pressure in the Spontaneously Breathing Newborn by Means of Bilateral Nasal Cannulation," *Monatsschr Kinderheilkd*, 1975: 123(4), pp. 141-146.
Boussarsar et al., "Relationship between ventilatory settings and barotrauma in the acute respiratory distress syndrome," Intensive Care Med., 2002: 28(4): 406-13.
Chang et al., "Reduced Inspiratory Muscle Endurance Following Successful Weaning From Prolonged Mechanical Ventilation," *Chest*, 2005: 128(2), pp. 553-559.
Charlotte Regional Medical Center, "Application of the Passy-Muir Tracheostomy and Ventilator," *Speech-Language Pathology Department*, Jan. 1995, 8 pages.
Christopher et al., "Preliminary Observations of Transtracheal Augmented Ventilation for Chronic Severe Respiratory Disease," *Resp. Care*, 2001: 46(1), pp. 15-25.
Christopher, et al., "Transtracheal Oxygen Therapy for Refractory Hypoxemia," *JAMA*, 1986: 256(4), pp. 494-497.
Ciccolella et al.; "Administration of High-Flow, Vapor-phased, Humidified Nasal Cannula Air (HF-HNC) Decreases Work of Breathing (WOB) in Healthy Subjects During Exercise," *AmJRCCM*, Apr. 2001: 163(5), Part 2, pp. A622. (Abstract Only).
Clini et al., "The Italian multicentre study on noninvasive ventilation in chronic obstructive pulmonary disease patients," *Eur. Respir. J.*, 2002, 20(3): 529-538.
Costa et al., "Influence of noninvasive ventilation by BiPAP® on exercise tolerance and respiratory muscle strength in chronic obstructive pulmonary disease patients (COPD)," *Rev. Lat. Am. Enfermagem.*, 2006: 14(3), pp. 378-382.
Díaz et al., "Breathing Pattern and Gas Exchange at Peak Exercise in COPD Patients With and Without Tidal Flow Limitation at Rest," *European Respiratory Journal*, 2001: 17, pp. 1120-1127.
Enright, "The six-minute walk test," *Resp. Care*, 2003: 8, pp. 783-785.
Ferreira et al., "Trigger Performance of Mid-level ICU Mechanical Ventilators During Assisted Ventilation: A Bench Study," *Intensive Care Medicine*, 2008,34:1669-1675.
Fink, "Helium-Oxygen: An Old Therapy Creates New Interest," *J. Resp. Care. Pract. now RT for Decision Makers in Respiratory Care*, 1999, pp. 71-76.
Gaughan et al., "A Comparison in a Lung Model of Low- and High-Flow Regulators for Transtracheal Jet Ventilation," *Anesthesiology*, 1992: 77(1), pp. 189-199.
Gregoretti, et al., "Transtracheal Open Ventilation in Acute Respiratory Failure Secondary to Severe Chronic Obstructive Pulmonary Disease Exacerbation," *Am. J. Resp. Crit. Care. Med.*, 2006: 173(8), pp. 877-881.
Haenel et al., "Efficacy of Selective Intrabronchial Air Insufflation in Acute Lobar Colapse," *Am. J. Surg.*, 1992: 164(5), pp. 501-505.
Keilty et al., "Effect of inspiratory pressure support on exercise tolerance and breathlessness in patients with severe stable chronic obstructive pulmonary disease," *Thorax*, 1994, 49(10): 990-994.
Köhnlein et al., "Noninvasive ventilation in pulmonary rehabilitation of COPD patients," *Respir. Med.*, 2009, 103: 1329-1336.
Koska et al., "Evaluation of a Fiberoptic System for Airway Pressure Monitoring," *J. Clin. Monit.*, 1993: 10(4), pp. 247-250.
Lewis, "Breathless No More, Defeating Adult Sleep Apnea," *FDA Consumer Magazine*, Jun. 1992, pp. 33-37.
Limberg et al., "Changes in Supplemental Oxygen Prescription in Pulmonary Rehabilitation," *Resp. Care*, 2006:51(11), p. 1302.
MacInryre, "Long-Term Oxygen Therapy: Conference Summary," *Resp. Care*, 2000: 45(2), pp. 237-245.
MacIntyre et al., "Acute exacerbations and repiratory failure in chronic obstructive pulmonary disease," *Proc. Am. Thorac. Soc.*, 2008: 5(4), pp. 530-535.
Massie et al., "Clinical Outcomes Related to Interface Type in Patients With Obstructive Sleep Apnea/Hypopnea Syndrome Who Are Using Continuous Positive Airway Pressure," *Chest*, 2003: 123(4), pp. 1112-1118.
McCoy, "Oxygen Conservation Techniques and Devices," *Resp. Care*, 2000: 45(1), pp. 95-104.
McGinley, "A nasal cannula can be used to treat obstructive sleep apnea"; *Am. J. Resp. Crit. Care Med.*, 2007: 176(2), pp. 194-200.
Menadue et al., "Non-invasive ventilation during arm exercise and ground walking in patients with chronic hypercapnic respiratory failure," *Respirology*, 2009, 14(2): 251-259.
Menon et al., "Tracheal Perforation. A Complication Associated with Transtracheal Oxygen Therapy," *Chest*, 1993: 104(2), pp. 636-637.
Messinger et al., "Tracheal Pressure Triggering a Demand-Flow CPAP System Decreases Work of Breathing," Anesthesiology, 1994: 81(3A), p. A272.
Messinger et al., "Using Tracheal Pressure to Trigger the Ventilator and Control Airway Pressure During Continuous Positive Airway Pressure Decreases Work of Breathing," *Chest*, 1995: vol. 108(2), pp. 509-514.
Mettey, "Use of CPAP Nasal Cannula for Aids of the Newborns in Tropical Countries," *Medecine Tropicale*, 1985: 45(1), pp. 87-90.
Nahmias et al., "Treatment of the Obstructive Sleep Apnea Syndrome Using a Nasopharyngeal Tube", *Chest*, 1988:94(6), pp. 1142-1147.
Nava et al., "Non-invasive ventilation," *Minerva Anestesiol.*, 2009: 75(1-2), pp. 31-36.
Passy-Muir Inc., "Clinical Inservice Outline", Apr. 2004, 19 pages.
Peters et al., "Combined Physiological Effects of Bronchodilators and Hyperoxia on Exertional Dyspnea in Normoxic COPD," *Thorax*, 2006: 61, pp. 559-567.

(56) References Cited

OTHER PUBLICATIONS

Polkey et al., "Inspiratory pressure support reduces slowing of inspiratory muscle relations rate during exhaustive treadmill walking in sever COPD," Am. J. Resp. Crit. Care Med., 1996: 154(4, 10), pp. 1146-1150.
Porta et al., "Mask proportional assist vs pressure support ventilation in patients in clinically stable condition with chronic venilatory failure," Chest, 2002: 122(2), pp. 479-488.
Prigent et al., "Comparative Effects of Two Ventilatory Modes on Speech in Tracheostomized Patients with Neuromuscular Disease," Am. J. Resp. Crit. Care Med., 2003: 167(8), pp. 114-119.
Puente-Maestu et al., "Dyspnea, Ventilatory Pattern, and Changes in Dynamic Hyperinflation Related to the Intensity of Constant Work Rate Exercise in COPD," Chest, 2005: 128(2), pp. 651-656.
Ram et al., "Non-invasive positive pressure ventilation for treatment of respiratory failure due to exacerbations of chroic obstructive pulmonary disease," Cochrane Database Syst Rev., 2004(3):1-72.
Rothe et al., "Near Fatal Complication of Transtracheal Oxygen Therapy with the Scoop(R) System," Pneumologie, 1996: 50(10), pp. 700-702. (English Abstract provided.)
Rothfleisch et al., "Facilitation of fiberoptic nasotracheal intubation in a morbidly obese patient by simultaneous use of nasal CPAP," Chest, 1994, 106(1): 287-288.
Sanders et al., "CPAP Via Nasal Mask: A Treatment for Occlusive Sleep Apnea," Chest, 1983: 83(1), pp. 144-145.
Sinderby et al., "Neural control of mechanical ventilation in respiratory failure," Nat. Med., 1999: 5(12), pp. 1433-1436.
Somfay et al., "Dose-Response Effect of Oxygen on Hyperinflation and Exercise Endurance in Nonhypoxaemic COPD Patients," Eur. Resp. J., 2001: 18, pp. 77-84.
Sullivan et al., "Reversal of Obstructive Sleep Apnoea by Continuous Positive Airway Pressure Applied Through The Nares," The Lancet, 1981: 1(8225), pp. 862-865.
Sullivan, "Home treatment of obstructive sleep apnoea with continuous positive airway pressure applied through a nose-mask," Bull Eur Physiopathol Respir., 1984: 20(1), pp. 49-54.
Tiep et al., "Pulsed nasal and transtracheal oxygen delivery," Chest, 1990: 97, pp. 364-368.
Tsuboi et al., "Ventilatory Support During Exercise in Patients With Pulmonary Tuberculosis Sequelae," Chest, 1997: 112(4), pp. 1000-1007.
VHA/DOD Clinical Practice Guideline, "Management of Chronic Obstructive Pulmonary Disease," Aug. 1999, Ver. 1.1a, Updated Nov. 1999.
Wijkstra et al., "Nocturnal non-invasive positive pressure ventilation for stable chronic obstructive pulmonary disease," Cochrane Database Syst. Rev., 2002, 3: 1-22.
Yaeger et al., "Oxygen Therapy Using Pulse and Continuous Flow With a Transtracheal Catheter and a Nasal Cannula," Chest, 1994: 106, pp. 854-860.
Walsh, "McGraw Hill Pocket reference Machinists' and Metalworker' Pocket Reference," New York McGraw-Hill, 2000, pp. 3-67, submitting 3 pages.
International Preliminary Report and Written Opinion on Patentability for PCT/DE2004/001646, dated Jul. 3, 2006.
European patent Office Search Report issued Oct. 19, 2007 in co-pending EP 04762494.
International Search Report and Written Opinion for PCT/US04/26800 issued Jun. 22, 2006.
International Search Report and Written Opinion for PCT/US07/12108, dated Aug. 8, 2008.
International Search Report and Written Opinion for PCT/US07/17400, dated Apr. 28, 2008.
International Search Report and Written Opinion for PCT/US08/64015, dated Sep. 26, 2008.
International Search Report and Written Opinion for PCT/US08/64164, dated Sep. 29, 2008.
International Search Report and Written Opinion for PCT/US08/78031, dated Nov. 24, 2008.
International Search Report and Written Opinion for PCT/US08/78033, dated Dec. 3, 2008.
International Search Report and Written Opinion for PCT/US09/054673, dated Oct. 8, 2009.
International Search Report and Written Opinion for PCT/US09/41027, dated Dec. 14, 2009.
International Search Report and Written Opinion for PCT/US09/59272, dated Dec. 2, 2009.
International Search Report and Written Opinion for PCT/US2006/036600, dated Apr. 3, 2007.
International Search Report and Written Opinion for PCT/US2009/031355 issued Mar. 11, 2009.
International Search Report and Written Opinion for PCT/US2009/041034, dated Jun. 10, 2009.
International Search Report and Written Opinion for PCT/US2010/029871, dated Jul. 12, 2010.
International Search Report and Written Opinion for PCT/US2010/029873, dated Jun. 28, 2010.
International Search Report and Written Opinion for PCT/US2010/029874, dated Jul. 12, 2010.
International Search Report and Written Opinion for PCT/US2010/029875, dated Jul. 12, 2010.
International Search Report and Written Opinion for PCT/US2010/047920, dated Nov. 1, 2010.
International Search Report and Written Opinion for PCT/US2010/047921, dated Jan. 27, 2011.
International Search Report for PCT/DE2004/001646, dated Jan. 17, 2005.
European Search Report and Written Opinion for International Application No. PCTUS2010047920, Feb. 9, 2014, 7 Pages.
Espacenet, English Abstract JP2007229207, Sep. 13, 2007, 4 pages.
Haruyuki Kanemaru, English Translation of Office Action, Jul. 30, 2014, 5 pages.
Haruyuki Kanemaru, JP Office Action, Jul. 30, 2014, 6 pages.
Chinese Office Action issued by SIPO for Chinese Patent Application No. 201080049145.0.

* cited by examiner

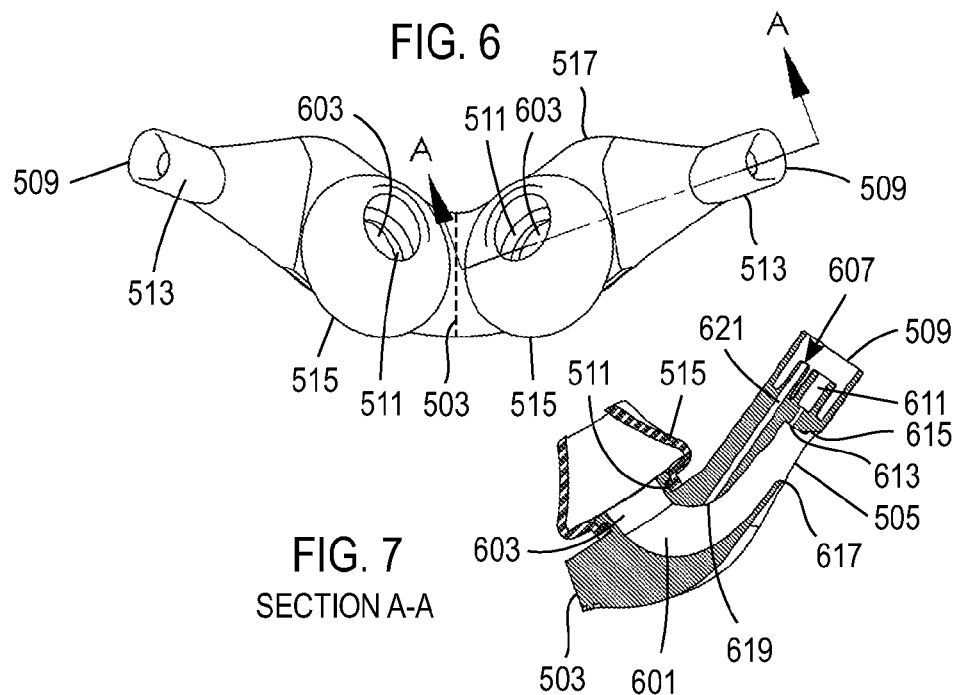
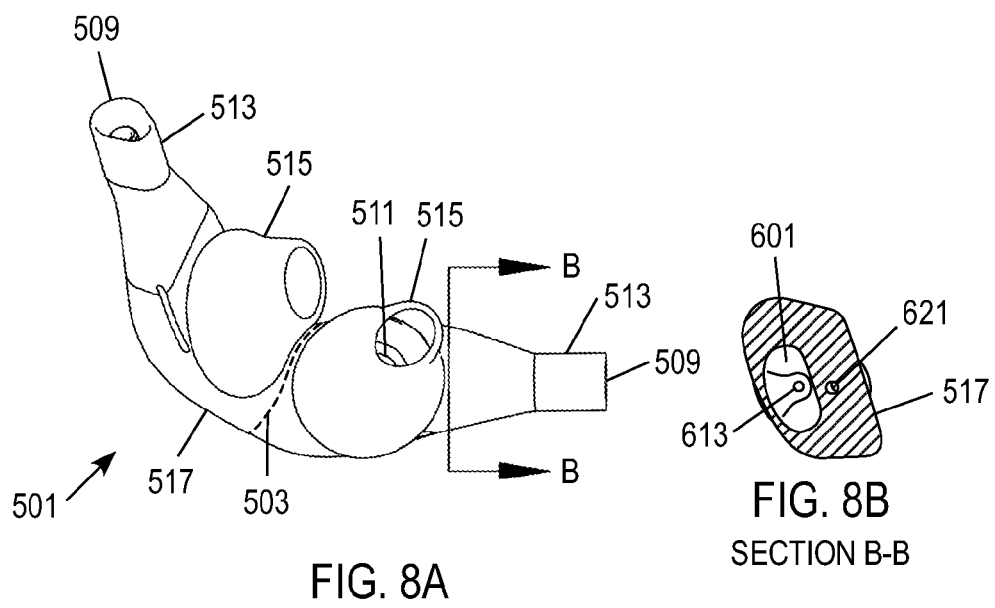

SECTION C-C

SECTION D-D

SECTION E-E

SECTION F-F

SECTION G-G

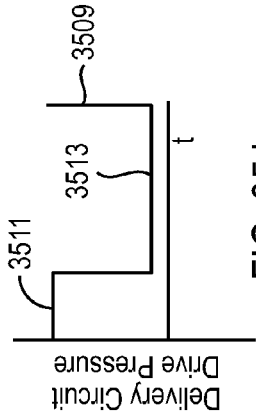
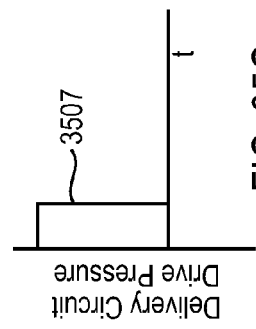
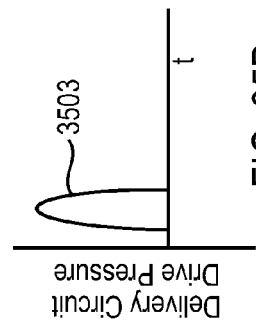
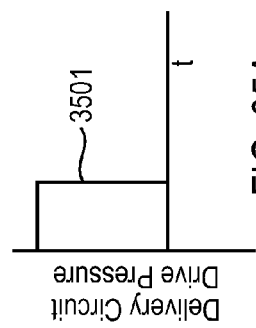
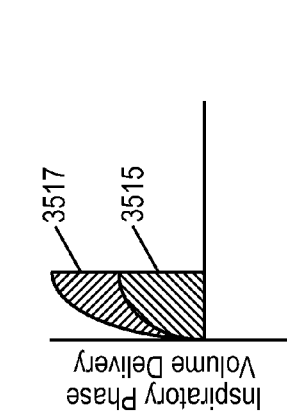
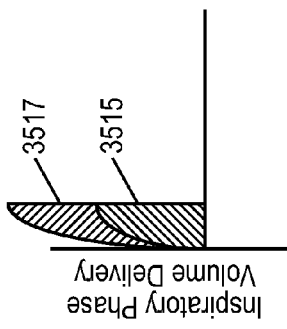
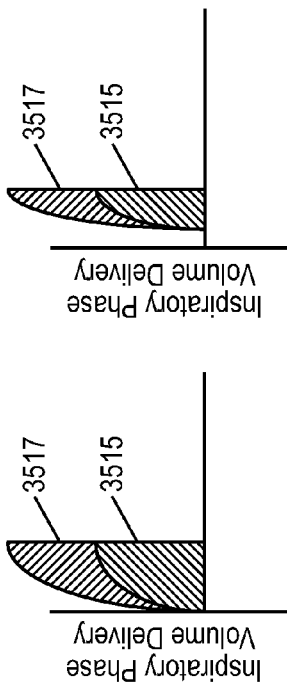
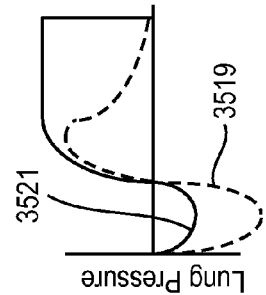
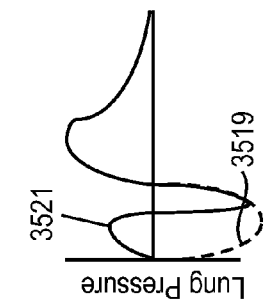
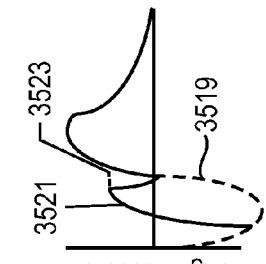
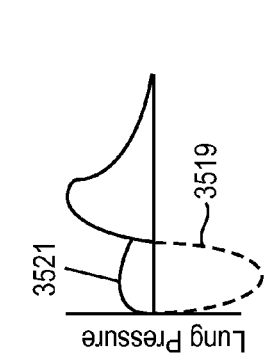

METHODS, SYSTEMS AND DEVICES FOR NON-INVASIVE VENTILATION INCLUDING A NON-SEALING VENTILATION INTERFACE WITH AN ENTRAINMENT PORT AND/OR PRESSURE FEATURE

CROSS-REFERENCE TO RELATED APPLICATIONS

This application claims priority to U.S. Provisional Patent Application No. 61/239,728, filed Sep. 3, 2009, U.S. Provisional Patent Application No. 61/255,760, filed Oct. 28, 2009, U.S. Provisional Patent Application No. 61/294,363, filed Jan. 12, 2010, and U.S. Provisional Patent Application No. 61/306,370, filed Feb. 19, 2010; the contents of which are incorporated by reference herein in their entireties. This application also claims priority to U.S. Non-Provisional patent application Ser. No. 12/753,846, filed Apr. 2, 2010, PCT Patent Application No. PCT/US2010/029871, filed Apr. 2, 2010, U.S. Non-Provisional patent application Ser. No. 12/753,851, filed Apr. 2, 2010, PCT/US2010/029873, filed Apr. 2, 2010, U.S. Non-Provisional patent application Ser. No. 12/753,853, filed Apr. 2, 2010, U.S. Non-Provisional patent application Ser. No. 12/753,854, filed Apr. 2, 2010, PCT Application No. PCT/US2010/029874, filed Apr. 2, 2010, U.S. Non-Provisional patent application Ser. No. 12/753,856, filed Apr. 2, 2010, and PCT Patent Application No. PCT/US2010/029875, filed Apr. 2, 2010; the contents of which are incorporated by reference herein in their entireties. This application incorporates by reference U.S. Non-Provisional patent application Ser. No. 12/876,099, filed Sep. 3, 2010, entitled "METHODS, SYSTEMS AND DEVICES FOR NON-INVASIVE VENTILATION INCLUDING A NON-SEALING VENTILATION INTERFACE WITH A FREE SPACE NOZZLE FEATURE", and PCT Patent Application No. PCT/US2010/47920, filed Sep. 3, 2010, entitled "METHODS, SYSTEMS AND DEVICES FOR NON-INVASIVE VENTILATION INCLUDING A NON-SEALING VENTILATION INTERFACE WITH A FREE SPACE NOZZLE FEATURE".

FIELD OF THE INVENTION

The present invention relates to the field of ventilation therapy for persons suffering from respiratory and breathing disorders, such as respiratory insufficiency and sleep apnea. More specifically, the present invention relates to providing open airway ventilation with methods and devices that use non-sealing non-invasive nasal ventilation patient interfaces.

BACKGROUND OF INVENTION

There is a need for a minimally obtrusive nasal mask and ventilation system that delivers mechanical ventilatory support or positive airway pressure, and which unencumbers the patient. There are a range of clinical syndromes that require ventilation therapy that would benefit from such a mask and system, such as respiratory insufficiency, airway or sleeping disorders, congestive heart failure, neuromuscular disease, and a range of situations that would be benefited, such as chronic, acute, emergency, mass casualty and pandemic situations.

Oxygen therapy is available with devices that do not encumber the patient. However, oxygen therapy is used for far less severe forms of clinical syndromes compared to ventilation therapy. For example, some nasal mask oxygen therapy systems have been developed for the purpose of delivering mixtures of air and oxygen by entraining air into the mask, however these are not considered ventilation therapy or respiratory support, because they do not mechanically help in the work of breathing. Recently, a variant of oxygen therapy has been employed, known as high flow oxygen therapy (HFOT). In this case, the oxygen flow rate is increased beyond standard long term oxygen therapy (LTOT), for example, above 15 LPM. Because of the high flow rate, the oxygen must be humidified to prevent drying out the patient's airway. It has been reported that HFOT can slightly reduce the patient's absolute pleural pressure during spontaneous breathing, thus have a slight effect on work of breathing. These systems are inefficient in that they consume a significant quantity of oxygen, rendering them non-mobile systems and encumbering the patient.

Respiratory support and ventilation therapies exist that provide mechanical ventilation (MV) to the patient, and mechanically contribute to the work of breathing. MV therapies connect to the patient by intubating the patient with a cuffed or uncuffed tracheal tube, or a sealing face or nasal mask or sealing nasal cannula. While helpful in supporting the work of breathing, the patient interfaces used for MV are obtrusive and/or invasive to the user, and MV does not facilitate mobility or activities of daily living, therefore encumbers that patient and is a drawback to many potential users. Non-invasive ventilation (NIV) exists which ventilates a patient with a face or nasal mask rather than requiring intubation, which can be an advantage in many situations. However, the patient cannot use their upper airway because the interface makes an external seal against the nose and/or mouth, and in addition the system is not mobile, the combination of which does not enable activities of daily living.

For treating obstructive sleep apnea (OSA), the gold standard ventilation therapy is continuous positive airway pressure (CPAP) or bilevel positive airway pressure (BiPAP), which is a variant to NIV in that the patient partially exhales through exhaust ports in the mask and back into large gas delivery tubing, rather than through an exhalation circuit as in MV. Continuous positive pressure applied by the ventilator to the patient by a nasal or face mask that seals against the nose or face prevents upper airway obstruction. While effective, this therapy has poor patient compliance because the patient interface is obtrusive to the patient and the patient unnaturally breathes through both a mask and gas delivery circuit.

In summary, existing therapies and prior art have the following disadvantages: they do not offer respiratory support or airway support in a manner that unencumbers the patient and (1) is non-invasive, and un-obtrusive such that it allows for mobility and activities of daily living, (2) allows the sensation of breathing from the ambient surroundings normally, and (3) is provided in an easily portable system or a system that can be easily borne or worn by the patient.

SUMMARY OF INVENTION

The invention provides ventilation to a patient using non-invasive open-airway ventilation (NIOV), and a non-sealing nasal mask interface with a Venturi arrangement that does not completely cover or seal the opening of the patient's mouth or nose. A non-invasive open-airway non-sealing mask is preferably configured with a Venturi arrangement to create a change from negative pressure to positive pressure within the mask.

Embodiments of the present invention may include a system for providing ventilatory support, the system including: a gas source; a gas delivery circuit; a nasal interface that allows the patient to breathe ambient air through the nasal interface;

a gas flow path through the nasal interface, wherein the gas flow path comprises a distal end gas flow path opening; a nozzle associated with a proximal end of the nasal interface at a distance from the distal end gas flow path opening; and an entrainment port associated with the nasal interface, wherein at least a portion of the entrainment port is between the nozzle and the distal end gas flow opening, wherein the nozzle is in fluid communication with the gas delivery circuit and the gas source, wherein the nozzle delivers gas into the nasal interface to create a negative pressure area in the gas flow path at the entrainment port, wherein the nasal interface and the nozzle create a positive pressure area between the entrainment port and the distal end gas flow path, and wherein a combination of gas from the gas source and air entrained through the entrainment port provide ventilatory support.

Embodiments of the present invention may include a method of increasing airway pressure, the method including: providing a nasal interface that allows the patient to breathe ambient air through the nasal interface, wherein the nasal interface comprises a gas flow path, wherein the gas flow path comprises a distal end gas flow path opening and a proximal end gas flow path opening; providing a nozzle associated with a proximal end of the nasal interface at a distance from a nose; providing an entrainment port associated with the nasal interface substantially between the nozzle and a distal end of the nasal interface, wherein at least a portion of the entrainment port is between the nozzle and the distal end gas flow opening; and adapting the nozzle to be in fluid communication with a gas delivery circuit and a gas source, wherein the nozzle is capable of delivering gas into the nasal interface to create a negative pressure area in the gas flow path at the entrainment port, wherein the nasal interface and the nozzle create a positive pressure area between the entrainment port and the distal end of the nasal interface, and wherein a combination of gas from the gas source and air entrained through the entrainment port increases airway pressure.

The systems and methods of the present invention may further include that the nasal interface includes a sound reducing feature. The sound reducing feature may be angling the nozzle at an approximately 1-30 degree angle from a manifold gas flow path centerline axis. The sound reducing feature may be an off-centered nozzle positioned off of the manifold gas flow path centerline by 5-25%. The sound reducing feature may include a secondary gas flow exit that is separate from the entrainment port. The sound generated by the nasal interface may be <50 db at 1 meter. The gas flow path may include a first section that is a substantially lateral-to-midline section and a second section distal to the first section that is a substantially inferior-to-superior section, and a curve between the two sections, with the positive pressure area substantially generated proximal to the curve. A pressure sensing port may terminate in positive pressure region in the gas flow path. The gas flow path may include a left gas flow path and a separate right gas flow path. The left gas flow path and the right gas flow path may be pneumatically interconnected with an interconnecting channel. A manifold may be included, wherein the manifold is curved with a lateral-posterior-inferior curve on each side of the midline to position the manifold where most comfortable to the user. A manifold may be included, wherein the manifold includes at least one flex joint, and the at least one flex joint is located at a midline of the manifold. The manifold may be made of a flexible material. A manifold may be included, and wherein the manifold is made of a malleable material to be shaped to a face of a user. A manifold may be included, and a space adjustment at a center of the manifold. One or more nasal cushions may be attachable to the distal end gas flow opening, the one or more nasal cushions comprising a snap ring on pillows comprising a hard material, and a mating ring surrounding the distal end gas flow openings. One or more nasal cushions attachable to the distal end gas flow opening, the one or more nasal cushions including a rotatable connection to the nasal interface. A cross-sectional area of the gas flow path that may not decrease from the entrainment port to the distal end gas flow opening. A cross-sectional area of the gas flow path may be uniform from the entrainment port to the distal end gas flow opening. A cross-sectional area of the gas flow path may increase from the entrainment port to the distal end gas flow opening. Delivery of gas from the gas source may be synchronized with an inspiratory phase. A time of delivery of gas from the gas source may be modulated with respiratory rate to deliver a set volume at a different time and pressure amplitude based on a patient's spontaneous respiratory rate. The gas from the gas delivery source may be controlled by a wear-able ventilator. Ventilatory support may include reducing the work of breathing to treat respiratory insufficiency. Ventilatory support may include elevating airway pressure to treat sleep apnea. The nozzle and gas delivery tubing may be attached to only one side of the nasal interface. The gas flow path may not include abrupt angles. The abrupt angles may be substantially 90 degrees. A patient may receive approximately 20-200% entrained air relative to gas from the gas source in the combination of gas from the gas source and the air entrained through the entrainment port. The nozzle may include a tip, wherein at least a portion of the entrainment port is between the tip of the nozzle and the distal end gas flow opening. The tip of the nozzle may be located at a midpoint of the entrainment port. The tip of the nozzle may be approximately 5-60 mm from a centerline. The entrainment port may be completely distal to the nozzle. The entrainment port may have an average cross sectional area of approximately 0.035-0.095 square inches. The negative pressure area may be within the gas flow path. The negative pressure area may extend from the entrainment port to a location proximal to the distal end of the nasal interface. The negative pressure may be less than ambient. The negative pressure may be approximately −5 to −40 cmH2O. The positive pressure area may be within the gas flow path. The positive pressure area may extend within the gas flow path from a location distal to the entrainment port the distal end of the nasal interface. The positive pressure may be greater than ambient. The positive pressure may be approximately 0.01 to 0.50 psi. The combination of gas from the gas source and the air entrained through the entrainment port may increase upper airway pressure by approximately 2-35 cwp. The combination of gas from the gas source and the air entrained through the entrainment port may exit the nasal interface as laminar flow. The nasal interface may have throat length of approximately −0.75-2.0 inches. The gas delivery circuit may have an inner diameter of less than approximately 4 mm. At least one sensor may measure phases of breathing. A ventilator may be provided, wherein the ventilator comprises a control unit, and wherein the control unit adjusts an output of the ventilator to match a patient's ventilation needs based on information from the at least one sensor.

Embodiments of the present invention may include a system for increasing airway pressure, the system including: a gas source; a gas delivery circuit; a nasal interface that allows the patient to breathe ambient air through the nasal interface; a gas flow path through the nasal interface, wherein the gas flow path comprises a distal end gas flow path opening; a nozzle associated with a proximal end of the nasal interface at a distance from the distal end gas flow path opening; and wherein the nozzle is in fluid communication with the gas delivery circuit and the gas source, wherein the nozzle delivers gas into the nasal interface to create a negative pressure area in the gas flow path near the proximal end of the nasal interface, wherein the nasal interface and the nozzle create a positive pressure area within the gas flow path distal to the negative pressure area, and wherein a combination of gas from the gas source and air entrained in the gas flow path increases airway pressure.

The systems and methods of the present invention may further include an entrainment port associated with the nasal interface, wherein at least a portion of the entrainment port is between the nozzle and the distal end gas flow opening. The negative pressure area may extend from the entrainment port to a location proximal to the distal end of the nasal interface. A negative pressure may be less than ambient. The negative pressure may be approximately −10 to −50 cmH2O. The positive pressure may be greater than ambient. The positive pressure may be approximately 2-30 cmH2O.

Embodiments of the present invention may include a method of delivering a therapeutic level of gas to a patient wherein the amount of gas increases the pressure in the oropharyngeal airway to a pressure level able to reduce obstructive sleep apnea airway obstructions, the method including: attaching a nasal interface to a patient wherein the interface does not impede the patient from breathing ambient air directly through the interface; placing a jet nozzle in the nasal interface at the proximal end of the interface lateral to the nose, and placing an entrainment port in the nasal interface between the jet nozzle and the distal end of the nasal interface; attaching a ventilator to a gas delivery circuit and the gas delivery circuit to the jet nozzle and delivering gas from the ventilator to the nasal interface; delivering the gas from the nozzle into the nasal interface with a velocity that creates a negative pressure inside the interface at the location of the aperture, at a distance from the interface distal end; and the interface to create a positive pressure between the negative pressure area in the nasal interface and the interface distal end, wherein substantially all of the patient's exhaled gas flows through the ambient air entrainment aperture and virtually none flows through the gas delivery circuit, and wherein the therapeutic level of gas requires (a) gas from the ventilator and (b) ambient air entrained through the aperture by the velocity in the nasal interface created by the ventilation gas delivery.

The systems and methods of the present invention may also include monitoring the breathing pressure of the patient using an open airway pressure sensing port positioned between the entrainment aperture and the patient's nose, in the zone of positive pressure in the interface distal to the entrainment zone in the interface. A sound reduction feature may be provided in the nasal interface, selected from the group of (i) aligning the nozzle off axis with the axis of the gas flow path between the nozzle and the nose, (ii) off-centering the nozzle with the centerline axis of the gas flow path between the nozzle and the nose, (iii) including a secondary port in addition to the aperture in the interface for the escape-age of gas, (iv) a combination of the above. The ventilator may be provided with an OFF-ON mode including a first power-on/gas-delivery-OFF state, and a second power-on/gas-delivery-ON state, the OFF state preceding the ON state and providing zero gas delivery, and the ON state providing the therapeutic gas delivery, and providing a delay between the gas delivery OFF and ON state, wherein the gas delivery OFF state is activated initially after the ventilator is powered on and the interface is connected to the patient, and where during the gas delivery OFF state the patient breathes ambient air freely through the interface, and wherein after a delay, the gas delivery ON state is activated, wherein the activation is selected from the group of: (i) a predetermined time, (ii) a reduction in breath rate, (iii) a reduction in breathing pressure signal, (iv) a reduction in breathing pressure level, (v) a combination of the above. A speech detection filtering algorithm may be provided that prevents inadvertent delivery of gas to the patient in response to speech. Multiple amplitudes of gas may be delivered to the patient, wherein the different amplitudes are synchronized with the spontaneous breathing pattern of the patient, wherein a first amplitude is the therapeutic level of gas delivered in synchrony with the inspiratory phase, and a second amplitude is delivered in synchrony with the expiratory phase, where the transition from the expiratory phase amplitude to the inspiratory phase amplitude begins in expiratory phase before inspiratory phase begins. Greater than ⅓rd of the gas delivered to the patient may come from the ventilator, and greater than ⅕th of the gas delivered to the patient may come from ambient air entrained through the entrainment aperture. The gas delivery pressure output from the ventilator may be greater than 10 psi, wherein the flow rate output from the ventilator may be less than 25 lpm, wherein the gas delivery circuit gas delivery channel internal diameter may be less than 3 mm, and wherein the gas velocity exiting the nozzle may be greater than 100 meters/second. Humidified gas may be delivered to the patient with a delivery circuit in parallel with the ventilator gas delivery circuit and wherein the humidified gas is added to the interface at the negative pressure entrainment zone. A separate left and right breathing sensor may be used to measure, monitor, process and track left nostril and right nostril breathing pressures separately. The gas may be laminar when entering the nose by delivering the gas so that it exits the nozzle into the interface at high velocity of greater than 100 m/s, and enters the patient's nose with the entrained air at low velocity of less than 50 m/sec.

Embodiments of the present invention may include a ventilator for treating sleep apnea, the ventilator including: a gas delivery output, when enabled to deliver the therapeutic level, comprises an output pressure of >15 psi, and output flow rate of <25 lpm; a gas delivery output port of less than 3 mm internal diameter that is connectable to a gas delivery circuit; an input for an airway pressure sensing signal that is not in series with the ventilator gas flow line; a control system including: an input for the airway pressure sensing signal; speech filtering mode configured to prevent speech sounds from being classified as a breath; and an algorithm to deliver a required amount of flow to generate a desired amount of airway pressure proximal to the patient's airway based on the airway pressure sensing signal.

The systems and methods of the present invention may also include that the ventilator includes a cycling mode, the cycling mode comprising delivering multiple amplitudes of gas to the patient, wherein the different amplitudes are synchronized with the spontaneous breathing pattern of the patient, wherein a first amplitude is the therapeutic level of gas delivered in synchrony with the inspiratory phase, and a second amplitude is delivered in synchrony with the expiratory phase, where the transition from the expiratory phase amplitude to the inspiratory phase amplitude begins in expiratory phase before inspiratory phase begins. The ventilator may further include an OFF-ON algorithm comprising a power-on and gas flow off state and a power-on and gas flow on state, and comprising a delay between the gas flow OFF and ON state, wherein the gas flow OFF state is activated initially after the ventilator is powered on and a interface is connected to the patient, and where during the gas delivery OFF the control system receives breathing pressure signals from the patient while the patient breathes ambient air freely through the interface, and wherein after a delay, the gas flow ON state is activated, wherein the activation is selected from the group of: (i) a predetermined time, (ii) a reduction in breath rate, (iii) a reduction in breathing pressure signal, (iv) a reduction in breathing pressure level, (v) a combination of the above. The ventilator control system may be adapted to receive multiple breathing pressure inputs, corresponding to a dedicated input for the left and right nostril, and further wherein the control system comprises an algorithm adapted to adjust the gas output parameters based on comparing the two signals.

Embodiments of the present invention may include a nasal interface for treating sleep apnea comprising a tubular body with a distal end and proximal end and a gas flow path extending from the distal end to the proximal end, wherein the tubular body includes: a distal end configured to impinge with the nostril airway; a tubular body configured to curve laterally from the nostril distal end to the proximal end; an ambient air entrainment aperture in the tubular body between the proximal end and the distal end adapted to permit spontaneous breathing of ambient air directly through the aperture without impeding the user's breathing; a jet nozzle port positioned proximal to the aperture at the proximal end of the tubular body, and adapted to direct gas into the gas flow path and entrain air in from the entrainment aperture; and a pressure sensing port, wherein gas is delivered to the patient airway from a combination of the nozzle and air entrained through the aperture, and wherein substantially all the gas exiting the patient exits out of the aperture.

The systems and methods of the present invention may also include that the gas flow path includes a length between the nozzle and distal end allowing the velocity profile exiting the jet to merge with the walls of the gas flow path, and develop a positive pressure at a location proximal to the distal end and outside the nose. The minimum cross section of the gas flow path may be greater than or equal to the cross sectional area of the entrainment aperture. The entrainment aperture may be positioned in the tubular body at the anterior side of the tubular body, to entrain airflow into the aperture from in front of the face, and to direct exhaled gas flowing out of the aperture away from the face. The tubular body may include a sound reducing feature selected from the group of: a secondary port near the distal end, a nozzle position that is off-centered from the centerline axis of the tubular body, a nozzle angle that directs gas into the wall of the tubular body. The tubular body may include an internal volume of less than 0.40 cubic inches. The tubular body may include a gas flow resistance of less than 4 cmH2O pressure at 60 lpm gas flow. The pressure sensing port may be positioned in the positive pressure area of the tubular body. A left and a right tubular body may be provided, wherein each tubular body includes a pressure sensing port. An entrainment pressure sensing port may be located near the entrainment aperture, and a pressure sensing port may be located near the distal end.

Embodiments of the present invention may include a method of delivering a therapeutic level of gas to a patient wherein a delivered amount of gas increases pressure in an oropharyngeal airway to a pressure level able to reduce an obstructive sleep apnea airway obstruction, the method including: providing a nasal interface that does not impede the patient from breathing ambient air directly through the nasal interface, wherein the nasal interface includes: a jet nozzle in the nasal interface at a proximal end of the nasal interface substantially lateral to a nose; and an entrainment port in the nasal interface substantially between the jet nozzle and a distal end of the nasal interface; a ventilator and a gas delivery circuit, wherein the ventilator is in fluid communication with the jet nozzle via the gas delivery circuit; and delivering gas from the jet nozzle into the nasal interface with a velocity that creates a negative pressure area inside the nasal interface at the location of the entrainment port, at a distance from the distal end of the nasal interface, wherein the nasal interface is adapted to create a positive pressure area between the negative pressure area and the distal end of the nasal interface, and wherein substantially all exhaled gas flows through the entrainment port and virtually none of the exhaled gas flows through the gas delivery circuit. Delivery of gas may be synchronized with breathing of a patient.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention.

FIG. 6 shows a top view of the mask of FIG. 5.

FIG. 7 shows a front sectional view along part of the gas flow path of the mask at line A-A of FIG. 6.

FIG. 8A shows an isometric side view of the mask of FIG. 5.

FIG. 8B shows a sectional view through the gas flow path of the mask at Line B-B of FIG. 8A, showing the gas delivery nozzle.

FIG. 35A graphically shows a square waveform gas delivery pressure, according to one embodiment.

FIG. 35B graphically shows the volume delivery of FIG. 35A.

FIG. 35C graphically shows resulting lung pressure of FIG. 35A.

FIG. 35D graphically shows a sinusoidal waveform gas delivery pressure, according to one embodiment.

FIG. 35E graphically shows the volume delivery of FIG. 35D.

FIG. 35F graphically shows resulting lung pressure of FIG. 35D.

FIG. 35G graphically shows a square waveform gas delivery pressure for a portion of the inspiratory phase, according to one embodiment.

FIG. 35H graphically shows the volume delivery of FIG. 35G.

FIG. 35I graphically shows resulting lung pressure of FIG. 35G.

FIG. 35J graphically shows a multi-level waveform gas delivery pressure, according to one embodiment.

FIG. 35K graphically shows the volume delivery of FIG. 35J.

FIG. 35L graphically shows resulting lung pressure of FIG. 35J.

DETAILED DESCRIPTION OF THE EMBODIMENTS

Figure 1:
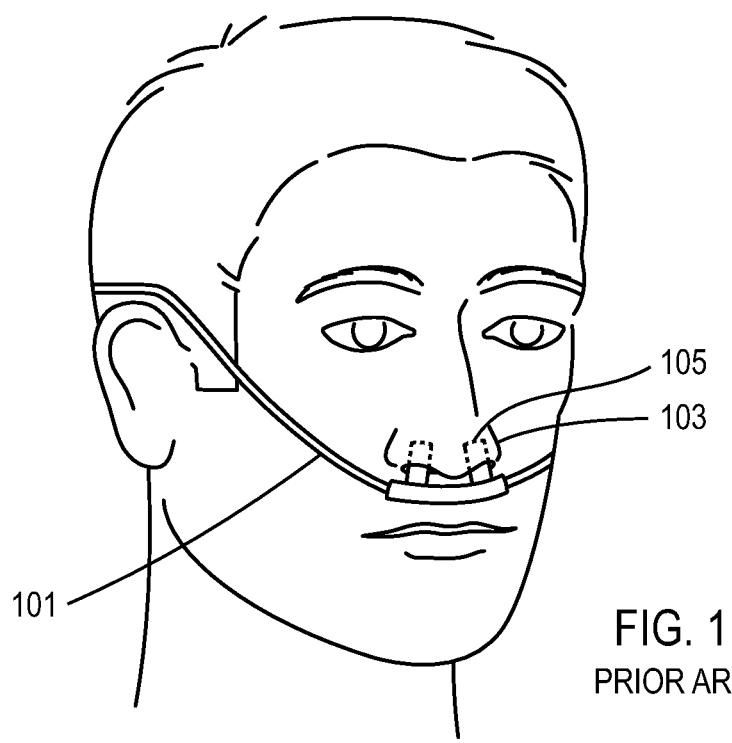
FIG. 1 shows a prior art conventional oxygen delivery cannula for administering oxygen therapy.

FIG. 1 shows a prior art conventional oxygen delivery cannula 101 for administering oxygen therapy. Extensions 105 on the cannula 101 are configured to enter nares 103. A proximal end (not shown) of the cannula 101 is connected to an oxygen delivery device that delivers continuous flow oxygen at 1-6 LPM to the user's nose, or delivers a bolus of oxygen upon detection of an inspiratory effort. The system of FIG. 1 does not mechanically support the work of breathing of the patient, and is not believed to be effective in preventing moderate to severe forms of OSA. The cannula of FIG. 1 is also used with another oxygen delivery therapy, high flow oxygen therapy (HFOT), in which more than 15 LPM of humidified oxygen is delivered at a continuous flow rate to the user's nose. Due to the high flow required for HFOT, the system is non-portable and the oxygen must be humidified.

Figure 2:
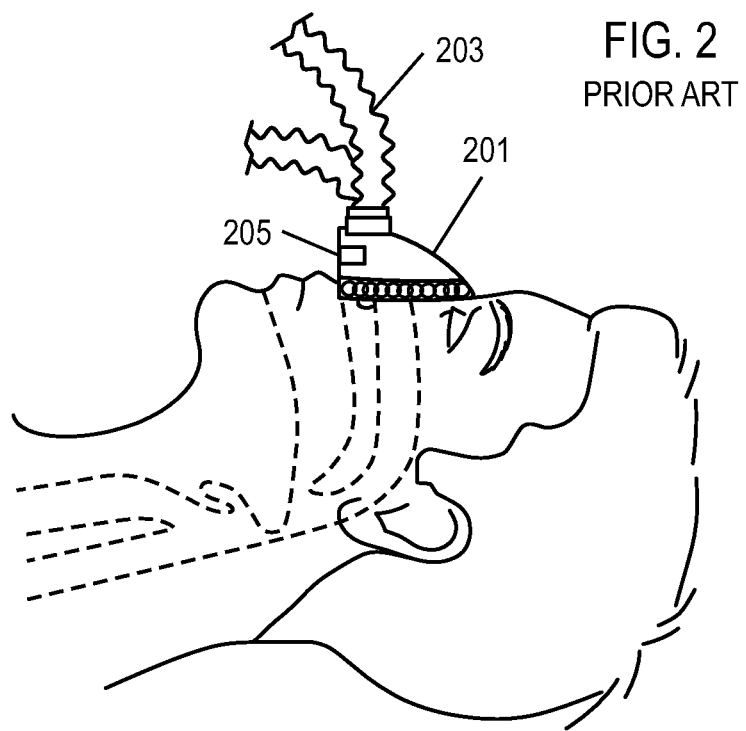
FIG. 2 shows a prior art conventional non-invasive ventilation using a nose mask and using a CPAP or BiPAP ventilation mode.

FIG. 2 shows a prior art respiratory support therapy for non-invasive ventilation (NIV), using a nose mask 201 in a bilevel positive airway pressure (BiPAP) ventilation mode. NIV is used to breathe for the patient, or can be used to help the breathing of a patient, in which case the patient's spontaneous breathing effort triggers the ventilator to deliver the pressure or volume-based mechanical ventilation (MV). All of the volume delivered to and from the lungs is delivered and removed from a ventilation circuit 203 and the nose mask 201.

A similar system to FIG. 2 can be used for OSA where a mask is sealed to the face so ventilation gas is provided by the ventilator and a portion of exhaled gas is exhaled through exhaust vents 205. NIV, continuous positive airway pressure (CPAP) and BiPAP are believed to be clinically effective modes and therapies for spontaneously breathing patients. These modes and therapies, however, do not facilitate activities of daily living (ADL's). For example, the ventilator cannot be borne by the patient, the patient cannot breathe room air naturally and freely because of the sealing mask, and the patient's upper airway cannot function normally and naturally because it is sealed off with the external mask seal, and in addition the gas delivery tubing is too bulky to realistically support mobility and ADL's.

Embodiments of the present invention will now be described with reference to the remaining figures. Respiratory support or airway support is provided in a manner and way that the patient is unencumbered. The non-invasive, non-sealing and unobtrusive systems and methods may allow for mobility and activities of daily life. The systems and methods allow for the sensation of breathing from ambient surroundings normally. The systems and methods provide an easily portable system that can be readily borne or worn by the patient, and gas delivery tubing that does not encumber the patient.

Systems and methods may include a gas delivery source, a gas delivery circuit, and a nasal interface that allow breathing ambient air through the nasal interface. A gas flow path through the nasal interface may have a distal gas flow path opening. A nozzle may be associated with a proximal end of the nasal interface a distance from the distal end gas flow path opening. In certain embodiments, at least a portion of an entrainment port may be between the nozzle and the distal end gas flow opening. The nozzle may deliver gas into the nasal interface to create a negative pressure area in the gas flow path at the entrainment port. The nasal interface and the nozzle may create a positive pressure area between the entrainment port and the distal end of the nasal interface. Gas from the gas delivery source and air entrained through the entrainment port may increase airway pressure.

Figure 3:
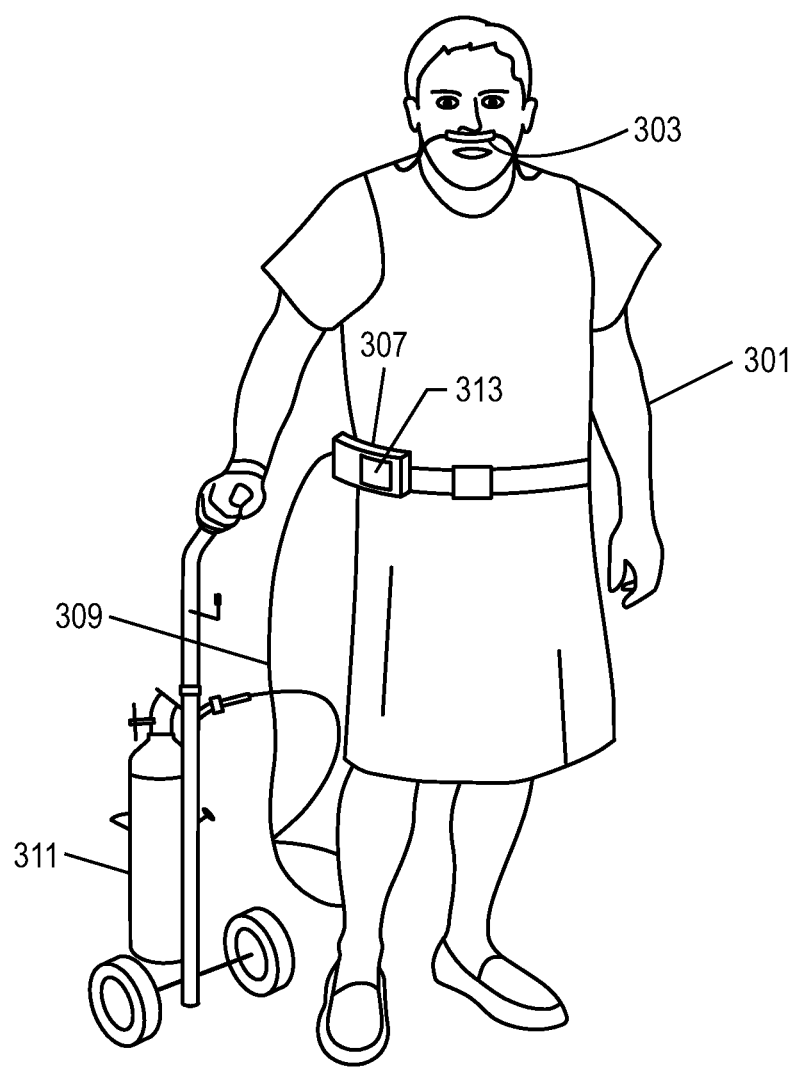
FIG. 3 shows an unencumbered patient using an embodiment of the invention to receive work of breathing support while ambulating.

FIG. 3 shows a patient 301 using an embodiment of the invention to provide mechanical ventilatory support, or work of breathing support, while being mobile. Conventional ventilators would require the patient to be stationary while receiving ventilatory support, or to use a wheel chair to carry the bulky and heavy equipment that is required for conventional ventilators. Conventional ventilators also require an encumbering sealing mask and large bore gas delivery tubing. The patient may also wear a ventilator module 307, which may be ultra-small that enables mobility when the invention is used for respiratory insufficiency. The ventilator may be coupled by tubing or other means 309 to an air and or oxygen supply 311. The ventilator module 307 may include a display 313 and/or input devices.

The present invention may include a non-sealing nasal mask patient interface, connected to the ventilator with small bore gas delivery tubing. The nasal mask may be uniquely non-sealing, so that the patient can inhale and exhale ambient air directly through the mask while receiving ventilatory support, in which there is negligible dead space volume in the mask. The mask may include a unique Venturi system that makes it possible for the ventilator to deliver relatively small amounts of gas to achieve relatively high levels of ventilatory support or airway pressure. The Venturi mask is described in more detail in FIGS. 6-31.

Various embodiments of the nasal interface 303 are described in detail in the following disclosure. The nasal interface 303 may be minimally obtrusive compared to standard masks, so that the patient can feel and act normally while receiving the therapy. For example, the patient can talk, swallow, eat or drink, and feel like they are breathing normally, with the nasal interface and therapy. The gas delivery tubing required may be very small compared to standard ventilator tubing, which more readily allows the patient to move around with the system, and to conceal the equipment and tubing needed for the therapy. The efficiency of the Venturi system in achieving therapeutic levels of lung or airway pressure while using low levels of gas volume, allows the gas supply to be relatively small, further enabling mobility of the patient, and or miniaturization of the ventilation equipment.

While FIG. 3 shows the patient using the invention for mobility, the invention can also be applied to sleep disordered breathing. In the later case, an advantage of the invention is that the mask and tubing is smaller than standard sleep apnea therapy masks and tubing. Additionally, the patient can have the sensation of breathing ambient air more directly making the therapy tolerable to the patient, rather than breathing through a machine, which is the sensation when using standard sleep apnea ventilation devices.

Figure 4:
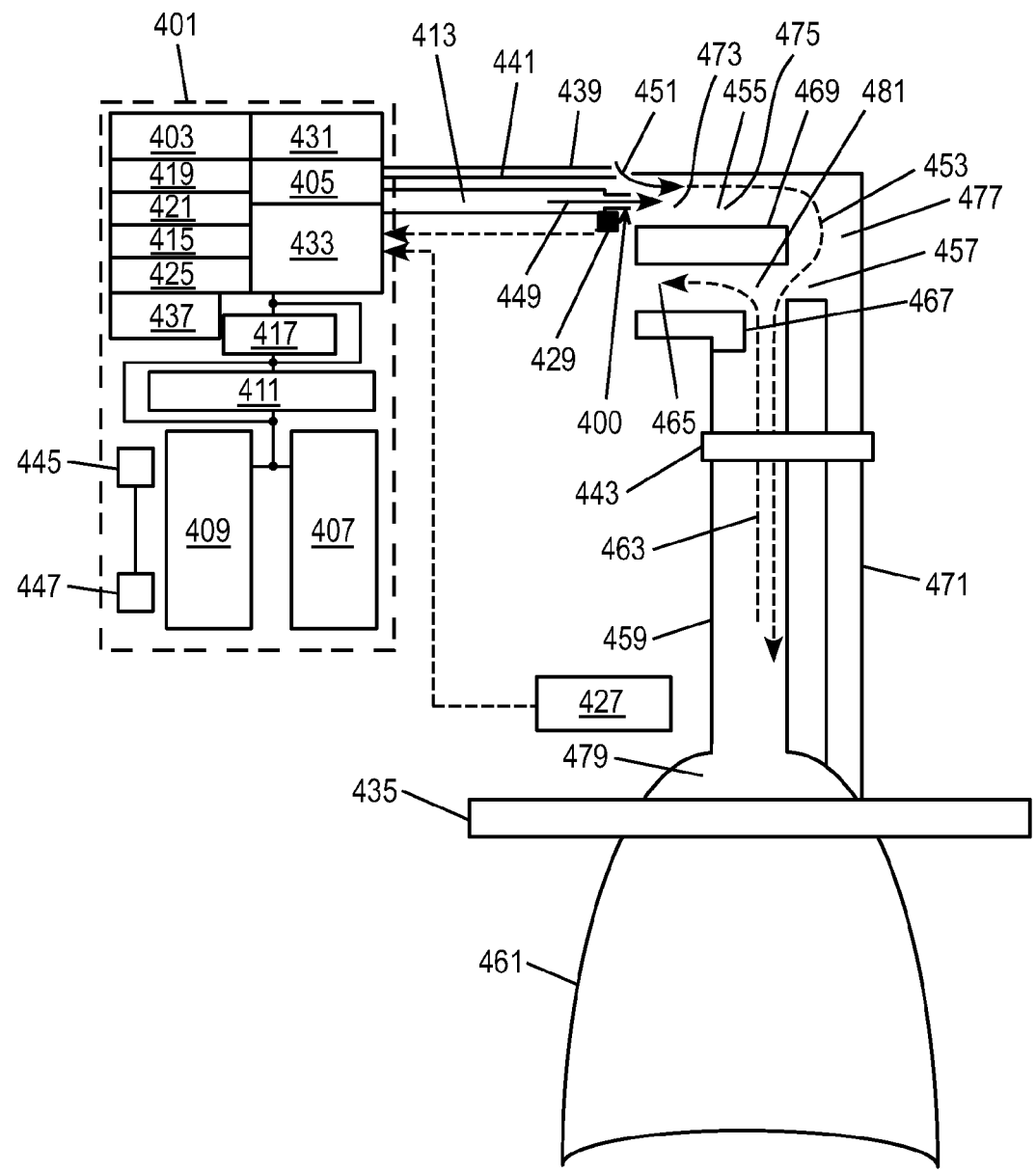
FIG. 4 is a schematic showing an exemplary system of the invention.

FIG. 4 is a block diagram describing an exemplary system of the invention. The exemplary system of FIG. 4 may be a wearable ventilator with portable gas source as shown in FIG. 3, or may be a different ventilator and/or gas source. Ventilator and patient interface features associated with the system are shown schematically. FIG. 4 depicts a non-invasive open nasal interface 400. The non-invasive open nasal interface will be described in various embodiments described herein, for example, in FIGS. 5-8B (curved nasal mask), FIGS. 9-15 (flexible joint), and FIGS. 16-25 and 29-31 (ergonomic configuration).

A ventilator module 401 may include or is in communication with several other functional accessories. The ventilator and the patient's internal anatomy from FIG. 3 are shown in schematic format in FIG. 4. A nasal airflow or nasal pressure sensor 429 is typically included. A transmitter 403 may be included to transmit information regarding the patient, the patient's therapy, and the ventilator performance to a remote location for review, analysis, remote intervention, two-way communication, and archiving. For example, the patient's compliance with the therapy or utilization of the therapy can be monitored and assessed. Important information can be trended, for example the patient's breath rate, I:E ratio, oxygen usage, activity level, or depth of breathing. Also, information can be sent to a ventilator 433, such as for example, sending programming instructions for setting titration options for the ventilator output to meet the needs of the patient, or sending instructions to the patient. The patient can also send information or questions to a remote clinician through the ventilator and transmitter 403.

An oxygen source 407 and/or a compressed air source 409 can be included, typically external to the ventilator module 401. In certain embodiments, however, the oxygen source 407 and/or the compressed air source 409 can be internal to the ventilator module 401 if the therapy is being used for stationary use, for example, in the home. A blender 411 can be included to control the fractional delivered O2 in a gas delivery circuit 413. A pulse oximeter 415 can be used to titrate settings of the ventilator module 401 to meet the physiological needs of the patient, for example setting the correct oxygen blender setting or ventilator volume output. In addition to compressed supplies of oxygen and air gas, the ventilator module 401 can include internal or external air and oxygen generating systems 417, such as a compressor, pump or blower to create pressurized air, an oxygen generator and/or pump to create pressurized oxygen gas, and/or a compressed gas accumulator. The oxygen source can also be liquid oxygen, or a liquid oxygen generating system. An internal or external humidifier 405 can be included for extended uses of the therapy, or if using in dry climates.

As the therapy is frequently used to help ADL's, and to promote activity, a pedometer 419 and/or actigraphy sensor 421 can be included internal to or external to a ventilator module 401. Optional sensors may include a $CO_2$ sensor 425, and/or an external breathing sensor unit 437. A $CO_2$ sensing line 439 and/or an airway pressure sensing line 441 may be present. One or more other external sensors may be included. For example, other external sensors may include an external respiration sensor or respiration effort sensor 427, such as a respiratory muscle effort sensor, a chest impedance sensor 435, or other types of sensors, such as a tracheal or other microphone or vibration sensor 443 or acoustical or ultrasonic sensor. The one or more external sensors may be used either as a redundant sensor to a nasal airflow or nasal pressure sensor 429, or to complement the information obtained from the nasal airflow or nasal pressure sensor 429, or in place of the nasal airflow or nasal pressure sensor 429. An oral airflow breathing sensor may also be used, for example, nasal airflow or nasal pressure sensor 429 may alternatively be an oral airflow sensor.

A drug delivery module 431 can be incorporated internally or externally to a ventilator module 401. Because of the challenges with current aerosolized drug delivery inhalers, the drug delivery module 431 can be used to propel and deposit medication particles deep in the respiratory system without a carrier propellant. Because the patient's using the therapy often may also require prescription medication, this may be a convenient and efficient way to administer the medication.

When the therapy is being used for respiratory support, the user may have two options: (1) wearing or toting the ventilator module 401 so that the user can be ambulatory or enjoy the activities of daily living, or (2) stationary use, in the event the patient plans on being stationary or does not have the ability to ambulate. For the later, the delivery circuit can optionally be provided in a 25-100 foot length, such that the gas source and ventilator module 401 can be stationary in the patient's home, while the patient can move around their home while wearing the interface and receiving the therapy. Or, the gas source can be stationary, and connected to the ventilator module 401 with a 25-100 foot hose, so that the patient can wear or tote the ventilator and be mobile within the range of the hose.

The ventilator module 401 may include one or more processors 445 and one or more memories 447 to analyze information and output therapies.

Ventilation gas 449 may exit at a speed that entrains ambient air 451, such that the combination of ventilation gas 449, entrained ambient air 451 and spontaneously inhaled air, if the patient is spontaneously breathing, is delivered 453 to the patient's airways, such as the nasal cavity 455, oropharyngeal airway 457, trachea 459, lung 461 and others, under power to create a clinically efficacious effect on the lung and airways. Patient may exhale 463 through the nose or mouth. Various airways are also included, such as nostril airway 473, nasal airway 475, oral airway 481, upper airway 477, and lower airway 479.

When using the invention, the patient breathes normally through their upper airway and through their nose, while receiving mechanical support through the interface. During exhalation, the exhaled gas preferably does not enter the gas delivery circuit but rather exits the nose or mouth directly to ambient air, or through, across or around the nasal interface 400 to ambient air. The patient can keep their mouth closed during use for example during inspiration, to help direct the mechanical support to the lower airways and past the oral cavity 465, base of the tongue 467, palate 469 and esophagus 471, or can use a mouth guard or chin band, if necessary. The patient may exhale through their mouth when using the therapy.

Figure 5:
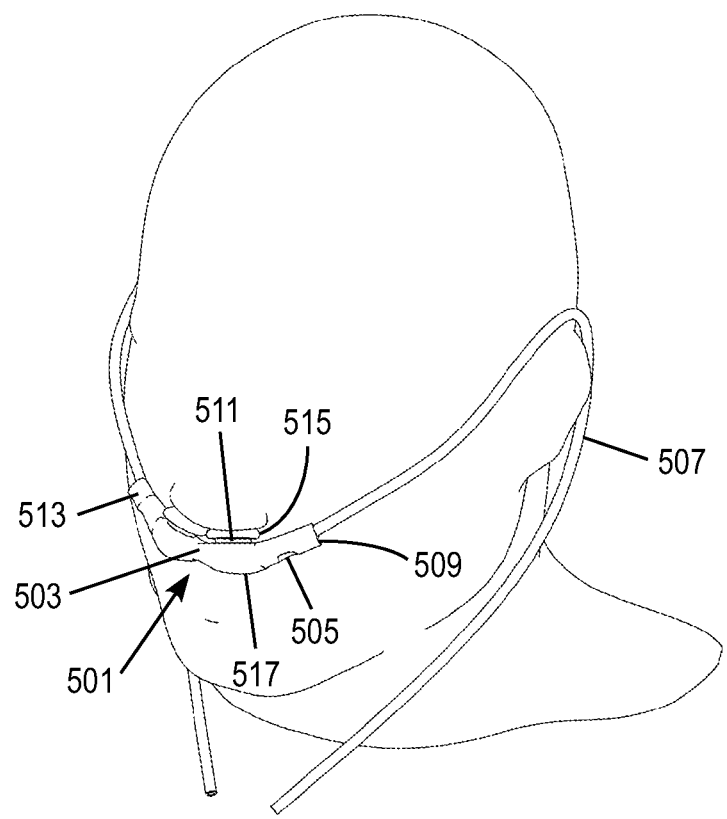
FIG. 5 shows an exemplary embodiment of a nasal interface where an open, non-sealing nasal mask may be curved and configured to be placed under the nose of the user, and which may extend bilaterally from the midline of the face to the sides of the nose.

FIGS. 5-8B describe an embodiment of the non-sealing open-airway nasal mask with a unique Venturi arrangement. FIG. 5 describes the nasal mask being worn on a person's face, with gas delivery exemplary shown routed around the patient's ears. FIG. 6 shows a top view of the mask of FIG. 5. FIG. 7 shows a sectional view of the mask of FIG. 6 along a mid-line A-A showing internal features of the mask. FIG. 8A shows a top-side view of the mask of FIG. 5 and FIG. 8B shows a sectional view of the mask of FIG. 8A along a line B-B showing internal features of the mask. As shown in FIGS. 6-8B, the mask may include a manifold 517, which can include one or more gas flow path 601 (FIG. 7) inside the manifold 517, one or more gas delivery jet nozzles 611 (FIG. 7) in communication with the gas flow path, and a gas delivery tube attachment 513 (FIG. 6) typically at or near a proximal end 509 (FIG. 6) of the manifold 517 and in communication with the gas delivery jet nozzles 611.

The gas flow path 601 may terminate at a distal end at a distal end gas opening 603 on a superior or superior-posterior side of the manifold 517 just lateral to a midline 503 of the manifold 517 on both sides of the midline 503. Each side of the manifold 517 may include a separate or interconnected gas flow path 601. The gas flow path 601 may direct ventilation gas into the user's nasal airway. The distal end gas flow openings 603 may include and/or be in fluid communication with a nasal cushion 515, which may engage with and/or impinge on the nostrils. The gas flow path 601 may proximally terminate at or near a proximal end of the gas flow path 601 at entrainment apertures 505 on an inferior, anterior, or inferior-anterior side of the manifold 517. The gas flow path 601 may distally terminate at or near the distal end gas flow openings 603.

The gas exiting the gas delivery jet nozzles 611 within the gas flow path 601 may create a negative pressure area at and/or near the entrainment apertures 505. The negative pressure may draw ambient air into the gas flow path 601 through the entrainment apertures 505. Preferably, at least a portion of the entrainment apertures 505 are located between the gas delivery jet nozzles 611 and the distal end gas flow openings 603. This unique Venturi configuration may allow a negative pressure region to form in the gas flow path 601 just inside the entrainment apertures 505 while forming a positive pressure region between the entrainment apertures 505 and the distal end gas openings 603. When gas is emitting from the gas delivery jet nozzles 611, this gas creates a cone-shaped flow or velocity profile. Typically, as explained in more detail subsequently, the area within this cone is positive pressure and the area outside of this cone is negative pressure. Typically, when the cone intersects with the internal walls of the gas flow path 601, the entire area distal to that intersecting point is under positive pressure.

Typically, the nasal interface 501 permits the user to breathe ambient air freely in and out of the manifold 517, through the entrainment apertures 505. Alternatively, the user may breathe ambient air at least partially in and out of separate spontaneous breathing ports, which may be separate from the entrainment apertures 505 and positioned elsewhere along the gas flow path 601 of the manifold 517, which will be described in more detail subsequently. The entrainment apertures 505 may be single apertures or multiple apertures and the spontaneous breathing ports, if present and separate from the entrainment apertures, may be single ports or multiple ports. In certain embodiments, the spontaneous breathing ports can be roughly or substantially in-line with the distal end gas flow openings 603. Alternatively, the spontaneous breathing ports can be located on a superior, inferior, or anterior surface of the manifold 517, or a combination of these surfaces. In general, the spontaneous breathing ports are preferably placed so that exhaled gas from the patient is directed in a natural velocity and or direction, so it does not irritate the users.

The entrainment apertures 505 are preferably located near tips 613 of the gas delivery jet nozzles 611, but can be placed in other locations on the manifold 517 as well. In certain embodiments, the tips 613 of the gas delivery jet nozzles 611 can be completely proximal to the entrainment aperture 505. In other embodiments, the tips 613 may be approximately flush with a proximal end 615 of the entrainment aperture 505, between a distal end 617 and the proximal end 615 of the entrainment aperture 505, or approximately flush with the distal end 617 of the entrainment aperture 505.

The entrainment apertures 505 can be positioned near the lateral proximal ends 509 of the manifold 517, and can be on the superior, anterior, inferior surfaces of the manifold 517 or combinations thereof. The entrainment apertures 505 can be variably adjusting. For example, the entrainment apertures 505 can be adjusted between fully open and fully closed. The adjustment can control the level of ventilatory support to the desired level that the overall system is intended to provide for the prevailing situation. The adjustment can be manual, but is preferably automatic with the use of valves, for example a valve that is controlled by a pressure signal delivered from the ventilator though a small bore conduit to the valve. Alternatively, the position of the gas delivery jet nozzles 611 relative to the entrainment apertures 505 can be adjusted by a slide mechanism, either manually or automatically. The level of support can range from partial support to full ventilator support.

As shown in FIG. 7, the gas delivery nozzle 611 of certain embodiments of the present invention may be proximal to the entrainment aperture 505, or as shown in other embodiments, the gas delivery nozzle 611 may be proximal to at least a portion of the entrainment aperture 505.

In contrast, typical jet pump systems position a nozzle distal and/or concentric to an entrainment port. The proximal positioning of the gas delivery jet nozzle 611 in the present invention preferably allows flow inside the manifold 517 to develop into positive pressure laminar flow in the shortest possible length or distance, which preferably minimizes obtrusiveness, which is a significant advantage. It is a significant advantage to develop laminar positive pressure flow within the manifold 517 prior to the gas entering the patient. Turbulent flow entering the nose is uncomfortable to the patient. Typical jet pumps are not concerned with generating positive pressure laminar flow within the jet pump area, rather the aim of a jet pump is to maximize the pressure exiting the jet pump area. Turbulent flow, if entering the patient, would include vortices and velocities that would create shearing effects that would increase noise and boundary effects that would irritate the nasal tissue. The laminar flow generated by the present invention may smooth out the flow profile, such that vortices and velocity profiles are more uniform, reducing the noise and irritation to a level acceptable for the application. For example, turbulent flow may include localized velocity currents that are greater than 300 lpm, whereas the laminar flow of the invention may produce a maximum localized velocity current of less than 200 lpm, based on nominal conditions.

In certain embodiments of the present invention, the gas flow path cross sectional area may not reduce between the entrainment aperture 505 and the distal end of the gas flow path 601, whereas typical jet pump systems include a reduction in cross section, which increases pressure output but decreases flow rate throughput, which would be undesirable in a medical ventilation application. The substantially uniform or optionally increasing cross sectional area between the proximal and distal ends of the gas flow path 601, may maximize the flow rate capable of being delivered by the system into the patient, and also reduces the inhalation and exhalation resistance through the manifold 517. In alternative embodiments, the gas delivery jet nozzles 611 can be positioned in the manifold 517 near the base of nasal cushions 515, inside the nasal cushions 515, or in the manifold 517 at any distance proximal to the nasal cushions 515.

It may be desirable to measure pressure being delivered to the patient, which can be done by sensing the pressure in the manifold 517 in a positive pressure zone using a pressure sensing lumen 621 terminating at a sensing port 619 in the positive pressure zone, shown in FIG. 7. The pressure inside the manifold 517 may be measured continuously by a transducer in a ventilator by a conduit connecting the pressure tap 607 to the transducer. Ideally, the pressure tap 607 may terminate at a point in the gas flow path 601 that has as few artifacts as possible, which is typically as close as possible to the distal end gas flow openings 603. The pressure taps 607 may typically include the pressure sensing port 619 and a sensing lumen 621 that extends back to the ventilator and is in communication with the ventilator control system.

The pressure inside the manifold 517 may be measured to detect the breathing of the patient, determine the phases of breathing, patient status, and time the delivery of the ventilation gas as appropriate, as well as for monitoring of the patient and ventilation pressure for alarm and control system purposes.

One or more other respiration sensors may be located inside the manifold 517 or on a surface of the manifold 517, as depicted in FIG. 4 by nasal airflow or nasal pressure sensor 429. The one or more other respiration sensors may be positioned in a location that is minimally affected by artifacts caused by the gas delivery jet nozzles 611, such as a vacuum signal. The one or more other respiration sensors can be other types of sensors, such as thermal, sound, vibration, gas composition, humidity, and force, or any combination thereof. The one or more other respiration sensors can be used to measure breathing pressures, but can also be used to measure breathing gas flows, or other breath-related parameters, such as sound or gas composition. There may be a combination of respiration sensors inside the manifold 517 and/or one or more respiration sensors on the outside of the manifold 517. The respiration sensors can be integral to the manifold 517, or located remotely from the nasal interface 501 in a ventilator (not shown). There may be two breath sensors, one for each nostril, or a single breath sensor. There may be multiple respiration sensors for a nostril, for example, an inspiratory breath sensor, and an expiratory breath sensor. The sensors can also be used to measure gas flow and gas volume, for example inspired and expired flow rate and inspired and expired tidal volume, of both the ventilator delivered gas and the spontaneously breathed gas. In addition to breath sensing, the apparatus may also include gas composition sensors, such as end-tidal $CO_2$ sensors, and oxygen sensors. $CO_2$ is a useful clinical parameter to measure and respond to, and can also be used as an additional breath detector, apnea detector, leak detector, and interface fitting detector (a certain characteristic $CO_2$ signal may indicate proper or improper fitting and placement of the interface). Oxygen may be a useful parameter to measure and can be used to determine the FIO2 being delivered by the system to the patient and therefore can be used as a measured parameter and to make ventilator adjustments to achieve the desired FIO2.

The mask may be configured to curve from the nose laterally and posteriorly away from the nose, which positions the components of the mask lateral to the nose, which makes the mask as unobtrusive as possible. The mask therefore does not hinder speaking or eating, and is away from the line of sight. The manifold 517 may be typically shaped in a compound arcuate shape to match the contours of the face under and to the side of the nose. The manifold 517 may typically curve bilaterally and posteriorly. The manifold 517 can also curve superiorly or inferiorly as it is curving laterally and posteriorly. The mask can be a bilateral assembly meaning gas delivery tubing 507 is attached to both the left and right side, or it can be unilateral meaning that the gas delivery tubing 507 is attached to only one side. The later configuration may be useful for side sleeping or to reduce the obtrusiveness on one side of the face.

FIGS. 5-8B describe a curved flow path devoid of abrupt angles, and a divided left and right flow path that are not pneumatically interconnected in the manifold 517. Abrupt angles may be substantially 90 degrees. Abrupt angles may hinder formation of laminar flow and may, therefore, be undesirable. The gas delivery tubing 507 can be routed around the ears of the user, or routed differently. The gas delivery tubing 507 may include a channel for delivering gas from the ventilator, and additional lumens, for example those found in FIG. 28, such as a pressure sensing lumen, gas sampling lumen or humidification delivery lumen.

Overall cross sectional geometry of the manifold 517 can be generally round or semi-round, or can be D-shaped, oval or variable, to optimize performance and ergonomics. The cross-sectional area can be variable, variably increasing from proximal to distal, and/or constant. Flatter cross sectional geometries that do not protrude far from the user's skin may be configured ergonomically. The internal structure of the manifold 517 may be devoid of corners and abrupt bends and angles to facilitate efficient gas flow fluid dynamics and sound generation. An abrupt bend or angle may be a bend or angle other than approximately 90 degrees, preferably approximately 120-150 degrees.

The manifold 517 may be made of a semi-rigid material, either a thermoplastic or elastomeric material, typically of 30-60 Shore A hardness in applications in which the manifold 517 is desired to be flexible, and 60-90 Shore A hardness in applications in which the manifold 517 is desired to be rigid or semi-rigid. The manifold 517 can also be constructed of both semi-rigid or rigid and flexible materials, for example a rigid construction for the gas flow path 601 and/or sensing lumen 621 portions. A soft flexible material may be found at one or more flex points, as described below in regards to FIGS. 9-31, or surrounding the gas flow path 601 and/or sensing lumen 621 portions. Alternatively, the skin or posterior side of the manifold 517 can be soft and flexible, while the anterior side of the manifold 517 can be rigid or semi-rigid.

The manifold 517 can also be constructed to be malleable or moldable by the user for the user to make minor adjustments to allow the nasal interface 501 to fit ideally to that individual. The overall nasal interface 501 can be disassemble-able, so the user can take the assembly apart for cleaning, or to assemble correct sizes of the different parts together to customize the fit. The manifold 517 and nasal cushions 515, if included, may typically be translucent, but also can be transparent or opaque. The gas flow path 601 geometry can be round in cross section or can be non-round, such as D-shaped, oval, or elliptical, in order to optimize both flow dynamics, sound and ergonomics. The gas flow path 601 in the manifold 517 may be dimensioned such that the patient can breathe freely through the gas flow path 601 without feeling restricted. Typically, the gas flow path 601 and Venturi are configured so that positive pressure is developed in the gas flow path 601 before the gas flow path 601 curves superiorly toward the distal end gas flow opening 603. The gas flow path 601 may be curved and devoid of abrupt angles and corners to channel the gas with as little resistance and disturbance as possible and so that the gas being delivered by the gas delivery jet nozzles 611 flows in an organized flow profile with minimal turbulence.

An inner diameter of the tip 613 of the gas delivery jet nozzle 611 can be between approximately 0.010" to approximately 0.080" in diameter or effective diameter, and may be preferably approximately 0.020" to approximately 0.060" in diameter or effective diameter. Other dimensions are possible depending on certain uses. The position of the gas delivery jet nozzles 611 within the manifold 517 and relative to the entrainment apertures 505 can be adjustable such that the adjustment can change the level of ventilatory support provided. Typically, the gas delivery jet nozzles 611 are positioned bilaterally; however, a single gas delivery jet nozzle is also contemplated.

The supplemental ventilation gas from the ventilator may be delivered to the manifold 517 from the ventilator via gas delivery tubing 507, which may be coupled to the lateral proximal ends 509 of the manifold 517. The gas delivery tubing 507 may include both a ventilator gas delivery channel and a pressure sensing conduit, as well as other channels such as a CO2 sampling channel or a humidification delivery channel, as depicted in FIG. 4. The gas delivery tubing 507 may typically extend around the ear to secure the nasal interface 501 to the patient, or may be routed in other positions on the user's face, for example, around the corners of the mouth to the front of the neck, in which case a strap may be included to strap the manifold 517 to the face and head.

Nasal cushions 515 may be coupled with and extend superiorly from the distal end gas flow openings 603. The nasal cushions 515 may impinge on the rim of the nostril, seal on the rim of the nostril, seal inside the nostril, impinge on the tissue underneath the nose, or various combinations of the above. The nasal cushions 515 may typically be soft and compliant to allow for comfortable contact with the nostril and, if a seal is intended, compress against the nostril in a comfortable manner. The nasal cushions 515 may typically include convolutions in the shape to allow the extension to flex in multiple planes, and to compresses along a centerline axis, to conform to the user's nose. The nasal cushions 515 can seal against the nostril rim or other part of the nostril so that there is not inadvertent leakage between the nasal cushions 515 and nose and so that the majority of the breathing gas flows through the nasal cushions 515. However, this seal does not need to be leak free, and in some embodiments the may be a desired gas flow between the nasal cushions 515 and the nostril. The nasal cushions 515 can be permanently affixed to the nasal interface 501 or can be removably attached. The nasal cushions 515 may be available in different sizes so that the user can select a size that matches their anatomy.

Figure 9:
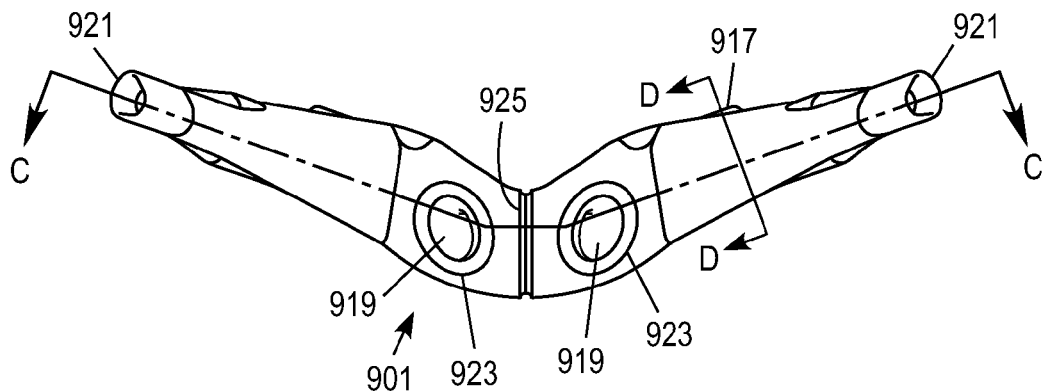
FIG. 9 shows a view of an alternate embodiment of a nasal mask of the invention.
Figure 10:
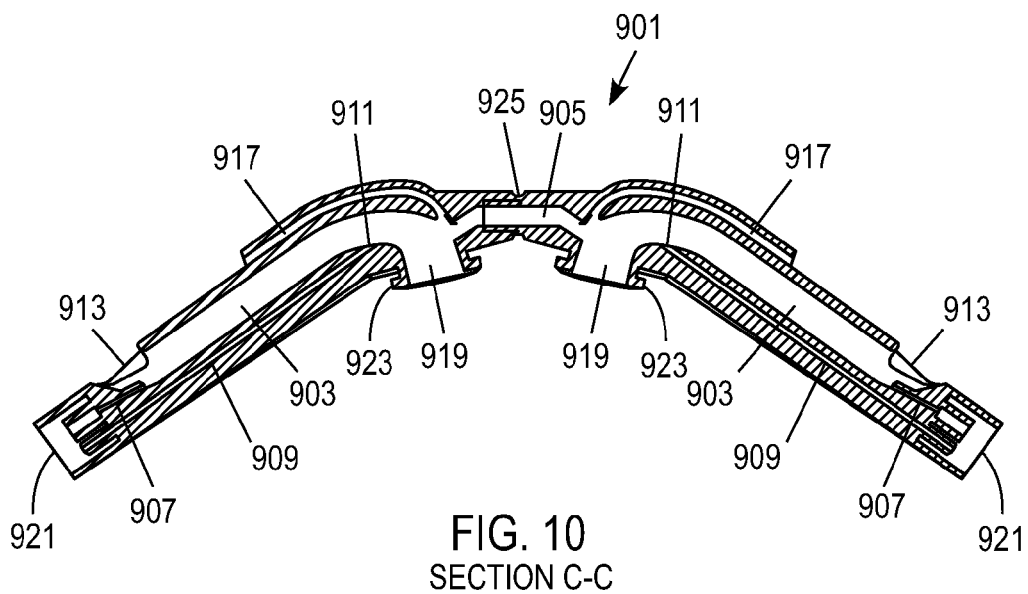
FIG. 10 shows a rear sectional view through the gas flow path of the mask at line C-C of FIG. 9.
Figure 11:
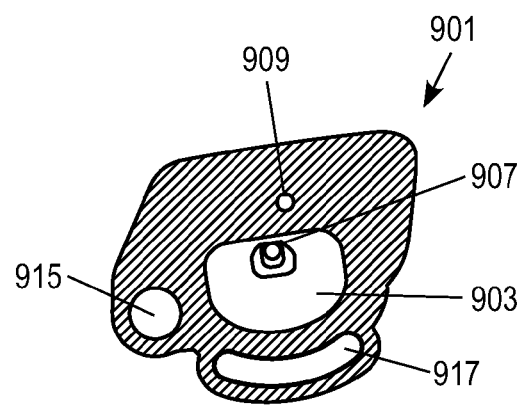
FIG. 11 shows a sectional view of the mask of FIG. 9 along a line D-D.

FIGS. 9-15 describe an alternate embodiment of a manifold 901. FIG. 9 shows a top view of the manifold 901. FIG. 10 shows a cross-sectional view of the manifold 901 at line C-C of FIG. 9, showing internal features including a gas flow path 903, an interconnecting channel 905, gas delivery jet nozzles 907, pressure sensing lumens 909, pressure sensing ports 911, entrainment apertures 913, gas sampling channel/spontaneous breathing aperture 915, exhaust flow path 917, and distal end gas flow openings 919. In this embodiment, spontaneous breathing is achieved through the entrainment apertures 913 and exhaust flow path 917. FIG. 11 shows a cross-sectional end view at line D-D of FIG. 9, showing internal features including the gas delivery jet nozzle 907, the gas flow path 903, the breathing and manifold pressure sensing lumen 909, gas sampling channel/spontaneous breathing aperture 915 and the exhaust flow path 917. The manifold 901 may flex along a centerline 925.

As shown in FIG. 10, the left and right gas flow path 903 can alternatively be joined together pneumatically with an interconnecting channel 905. A channel 905 may be useful in equalizing the flow delivery to each nostril in the event one nasal passage is congested. Providing an interconnecting channel 905 may allow the positive pressure in the left and right gas flow path 903 to equalize. The interconnecting channel 905 can be a fixed unchanging channel, or can be a channel with a valve that changes flow characteristics as needed. The interconnecting channel 905 cross sectional area may typically be greater than half of the cross sectional area of the gas flow path 903. In an alternate embodiment, the manifold 901 and the gas flow path 903 can also include a secondary channel, an exhaust flow path 917, used to divide the flows of exhaled gas exiting the patient and gas being delivered to the patient by the mask. Dividing these paths may significantly reduce shearing that occurs when gases are simultaneously exiting and being delivered to the patient, when these gas flows share a common path. The reduction in shearing leads to a reduction in sound generated by the system, which is a significant advantage in the applications intended by the invention, such as mobile ventilatory support, and sleep disordered breathing. When the exhaust flow path 917 is included, the exhaust flow path 917 may permit the patient to inspire through the exhaust flow path 917 in addition to inspiring through the entrainment aperture 913. The total gas inspired by the patient may be a combination of (1) supplemental ventilation gas being delivered from a ventilator through the gas delivery jet nozzles 907, (2) entrained air drawn through the entrainment apertures 913 by the ventilation gas exiting the gas delivery jet nozzles 907, and (3) air drawn through the entrainment apertures 913 or spontaneous breathing ports from the patient's own spontaneous breathing effort. Exhaled gas may be exhaled entirely through the entrainment apertures 913, through other ports in the manifold 901, through the patient's mouth, or any combination thereof.

The gas delivery jet nozzle 907 directional alignment may be aligned with the average centerline arc of the internal gas flow path 903 geometry of the manifold 901 in applications in which pressure generation is more important than minimizing sound. In alternate embodiments as shown, when minimizing sound generation is more important however, the gas delivery jet nozzles 907 can be angled away from a centerline and can be off-center which reduces sound generation but reduces pressure output generation. In the mobile ventilation application, a balance in the sound and pressure generated by the device is achieved by placing the gas delivery jet nozzle 907 at an approximately 10-30 degree angle to centerline, and approximately 5-25% off center, which can result in a sound of approximately 40-60 dbs and a maximum pressure output of approximately 12-35 cmH2O.

The gas delivery jet nozzle 907 at a proximal end 921 of the manifold 901 may also slightly protrude into the manifold gas flow path 903 to reduce sound generation, but not distal to the entrainment aperture 913 as shown. The manifold 517 may also include a nasal cushion connection element 923 at the distal end gas flow openings 919 of the gas flow opening 603 to which soft cushions may be attached, which impinge with or engage with the nares.

Figure 12:
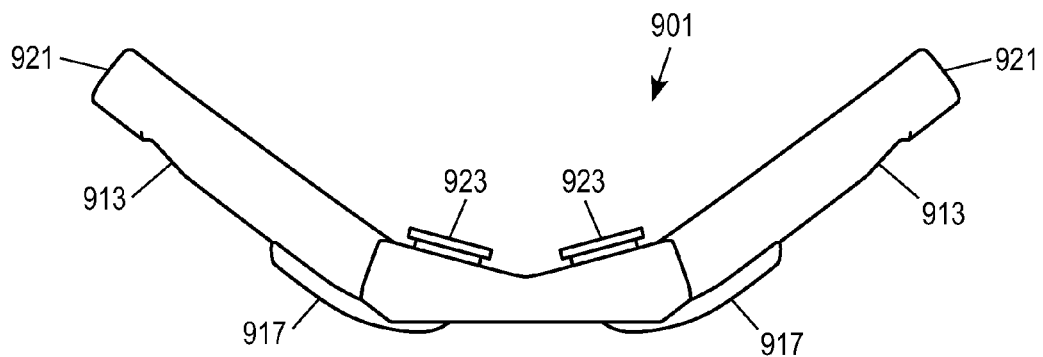
FIG. 12 is a front view of the mask of FIG. 9.
Figure 13:
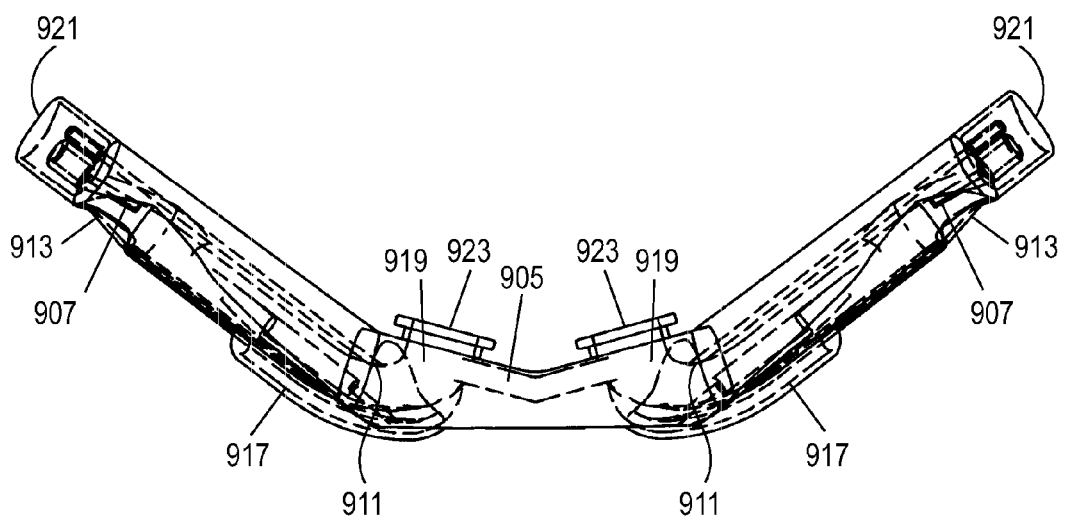
FIG. 13 is a hidden line view of the mask as oriented in FIG. 12 showing the gas flow path and exhaust flow path.
Figure 14:
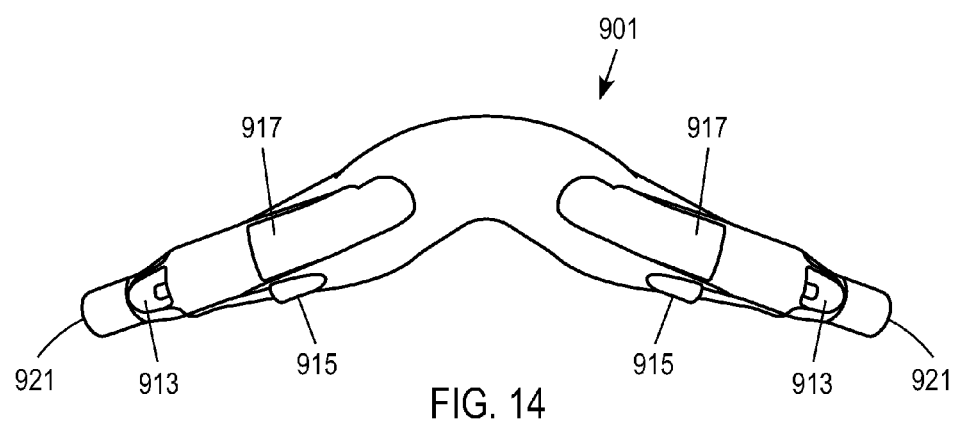
FIG. 14 is a bottom view of the mask of FIG. 12.
Figure 15:
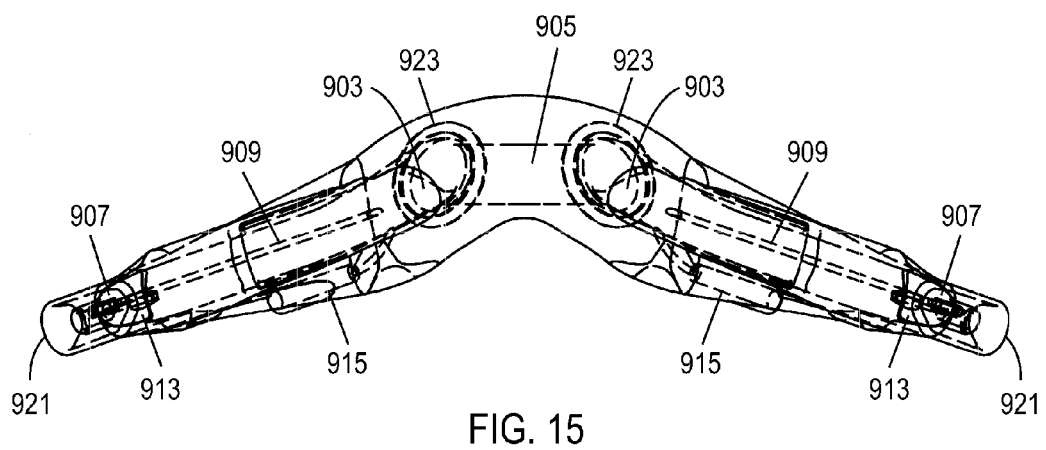
FIG. 15 is a hidden line view of the mask as oriented in FIG. 14, showing the gas flow path and sensing path.

FIGS. 12-15 describe in more detail the gas flow path 903, the exhaust flow path 917, the pressure sensing lumen 909 and pressure sensing port 911, the gas delivery jet nozzle 907, and the gas sampling channel/spontaneous breathing aperture 915 and the entrainment aperture 913. FIG. 13 is a hidden line view of the mask manifold front view shown in FIG. 12, and FIG. 15 is a hidden line view of the mask manifold bottom view shown in FIG. 14.

Figure 16:
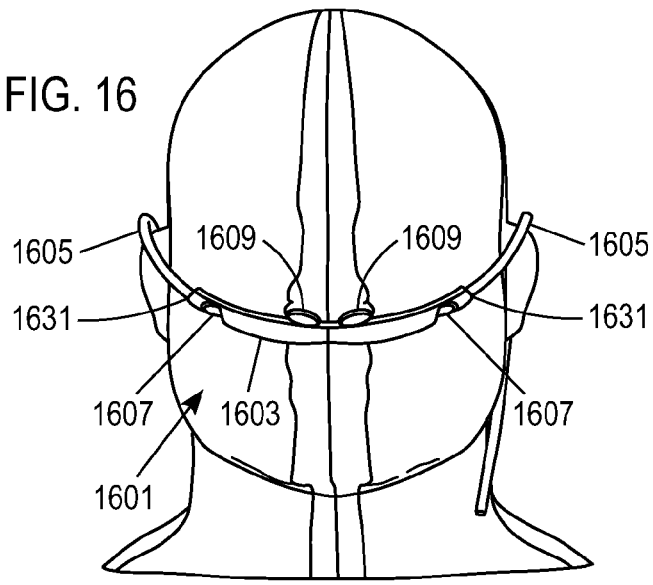
FIG. 16 shows a front view of an alternative embodiment of the nasal mask being worn by a patient, in which the mask is optimized for minimal size, ergonomics, form, fit and function.
Figure 17:
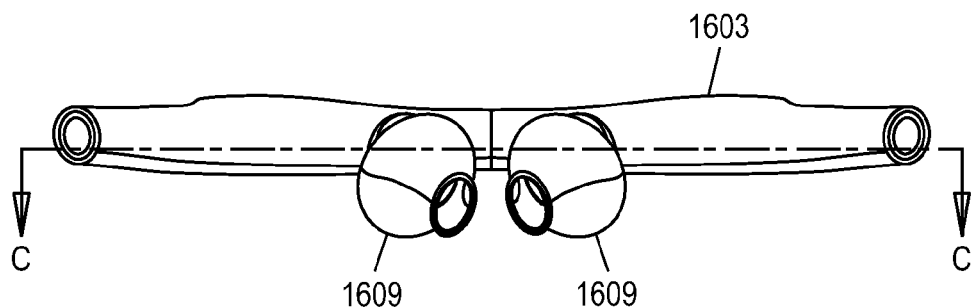
FIG. 17 is a top-posterior view of the mask shown in FIG. 16.

FIGS. 16-23 describe an alternate embodiment in which a nasal mask 1601 includes a manifold 1603 that is optimized for minimal size, minimal obtrusiveness, ergonomics, maximum comfort in form and fit, and maximal function. The nasal mask 1601 may include gas delivery tubing 1605, entrainment apertures 1607, and/or nasal cushions 1609. FIG. 16 shows a front view of the nasal mask 1601 being worn by a person. FIG. 17 is a top-posterior view of the mask shown in FIG. 16.

In certain embodiments, rotatable joints 1631 between the gas delivery tubing 1605 and the manifold 1603 may include detent settings. These detent setting joints can be used to adjust the angle of the manifold 1603 to adjust the angle of gas delivery nozzles to be in alignment with the patient's nostril airway. Alternatively, the gas delivery tubing 1605 can be connectable to the manifold 1603 in different rotational orientations to likewise align the gas delivery nozzles with the patient's nostril airway.

Figure 18:
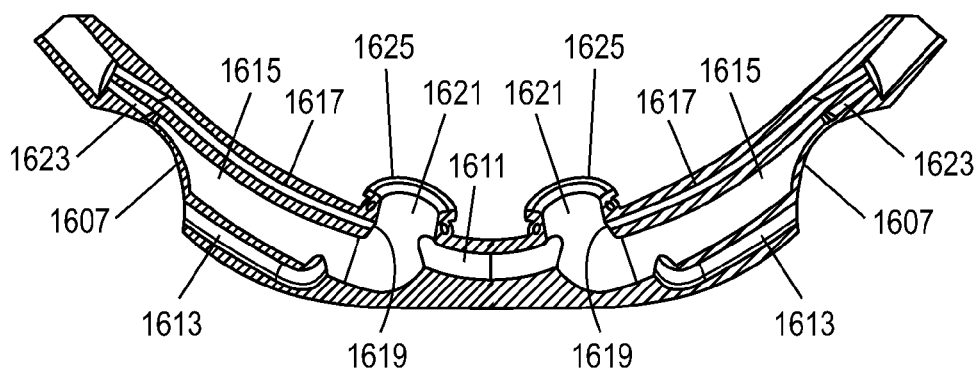
FIG. 18 shows a front cross-sectional view through the gas flow path, sensing line path and exhaust path of the mask of FIG. 16 through line E-E.

FIG. 18 is a front cross-sectional view of the nasal mask 1601 of FIG. 17 at line E-E, without nasal cushions. FIG. 18 shows the internal manifold features, including an interconnecting channel 1611, exhaled gas exhaust paths 1613, gas flow path 1615, pressure sensing lumens 1617 and ports 1619 terminating near a distal end 1621 of the gas flow path 1615, entrainment apertures 1607, gas delivery nozzles 1623 positioned proximal to a portion of the entrainment apertures 1607, and stems 1625 for attachment of the nasal cushions 1609. The stems 1625 can be positioned on the superior surface of the manifold 1603, or the superior-posterior surface. The nasal cushions 1609 can be attached to the manifold 1603 with a flex joint or comprise a flex point or corrugation to allow the nasal cushions 1609 to flex, bend, or angulate under slight pressure so that they self-align with the nostril openings. The nasal cushions 1609 can also compress inward toward the manifold 1603 so that the contact force at the contact points between the nasal cushions 1609 and the nostril are dampened and absorbed. The nasal cushions 1609 can have a distal round or oval opening that is off-center from the proximal base. For example, the distal end opening can be biased to the inward edge and posterior edge of the nasal cushions 1609. These features may make the nasal cushions 1609 a flexible seal or flexible quasi-seal with the nares and may make the assembly more forgiving to mate with different facial structures and inadvertent movement of the nasal mask

1601 while being worn. The nasal cushions 1609 are typically a compliant material such as silicone or elastomeric or thermoplastic material of Shore 10-60A, but other materials may be used.

Figure 19A:
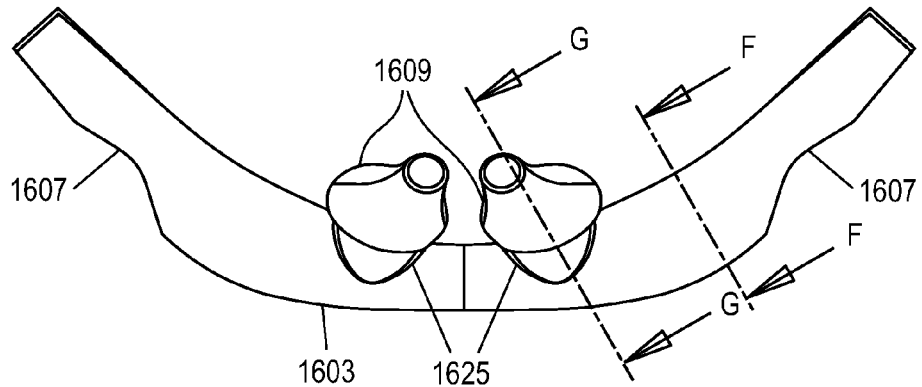
FIG. 19A shows a top view of the mask of FIG. 16.
Figure 19B:
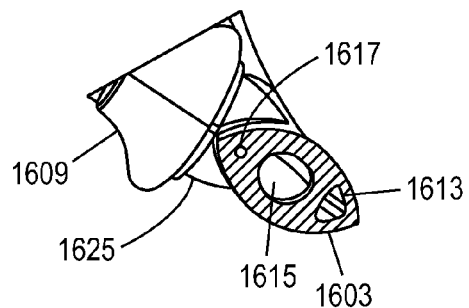
FIG. 19B shows a sectional view through the gas flow path, sensing line path and exhaust path of the mask of FIG. 19A through line F-F.
Figure 19C:
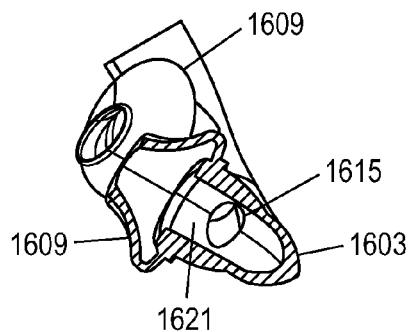
FIG. 19C shows a sectional view through the gas flow path of FIG. 19A through line G-G.
Figure 20:
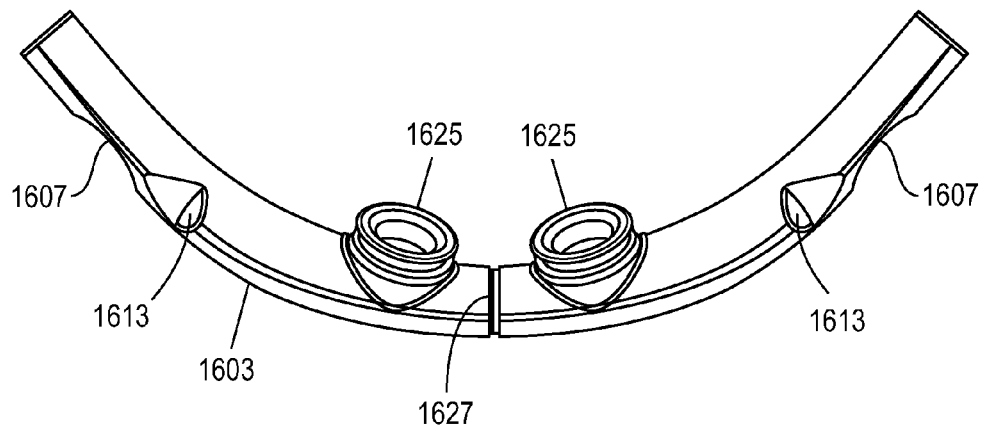
FIG. 20 shows a top view of the mask of FIG. 16 without nasal cushions.
Figure 21:
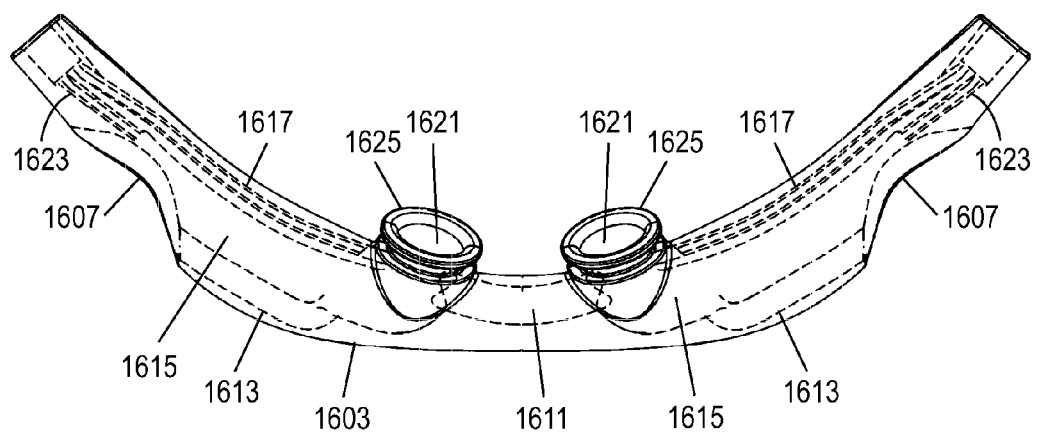
FIG. 21 shows a hidden line view of the gas flow path of the mask of FIG. 16, showing the gas flow path.
Figure 22:
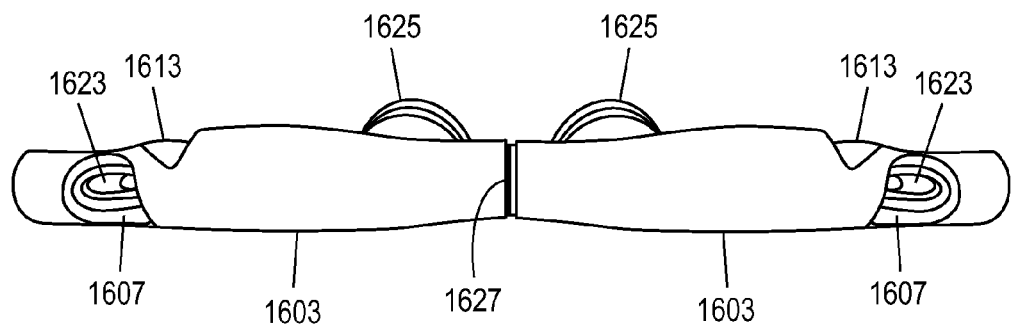
FIG. 22 shows an anterior-bottom view of the mask of FIG. 16.
Figure 23:
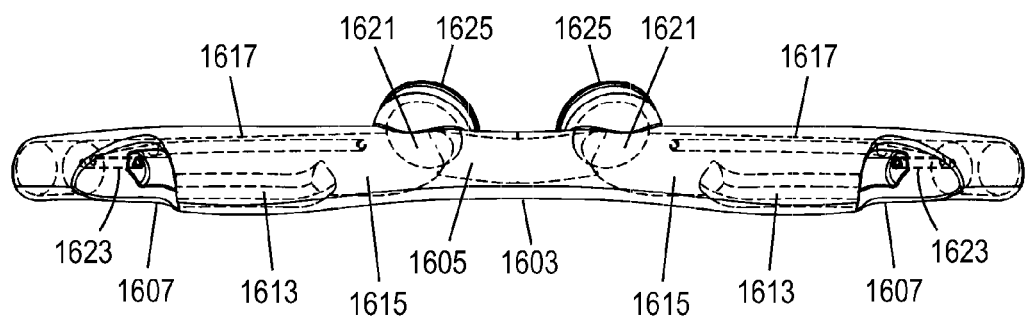
FIG. 23 shows a hidden line view of the mask as oriented in FIG. 22, showing the gas flow path.

FIG. 19A shows a top view of the mask of FIG. 16. FIG. 19B shows a sectional view through the gas flow path 1615, pressure sensing lumen 1617 and exhaust path 1613 of the mask of FIG. 19A through line F-F. FIG. 19C shows a sectional view through the gas flow path 1615 of FIG. 19A through line G-G. FIG. 20 shows a top view of the nasal mask 1601 of FIG. 16 without nasal cushions 1609. A flexible joint 1627 may be included. FIG. 21 shows a hidden line of the gas flow path 1615 of the nasal mask 1601 of FIG. 16. FIG. 22 describes an anterior-bottom view of the nasal mask 1601 of FIG. 16. FIG. 23 shows a hidden line view of the gas flow path 1615 of the nasal mask 1601 of FIG. 22.

Figure 24:
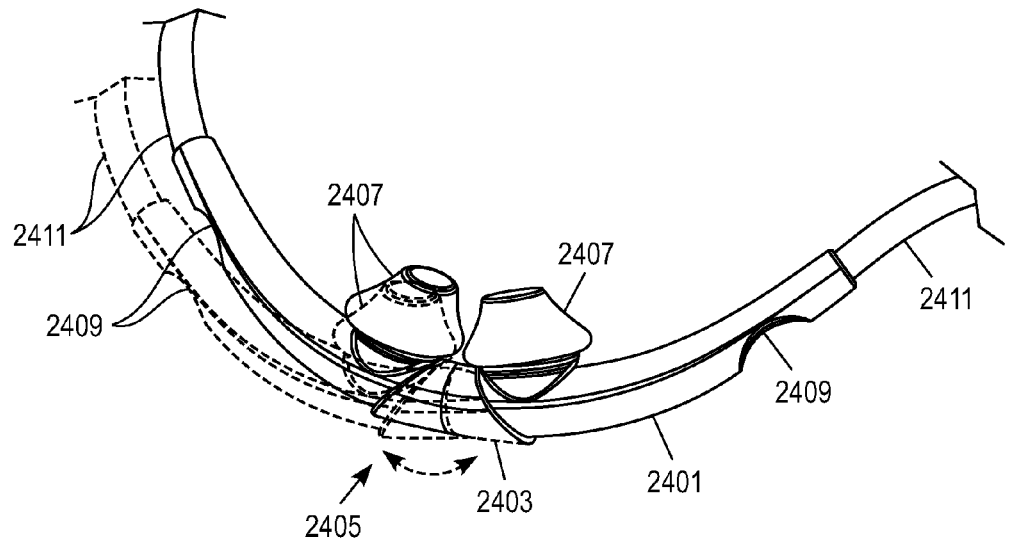
FIG. 24 shows an alternative embodiment of the mask of FIG. 16 in which the mask can flex at its center portion.
Figure 25:
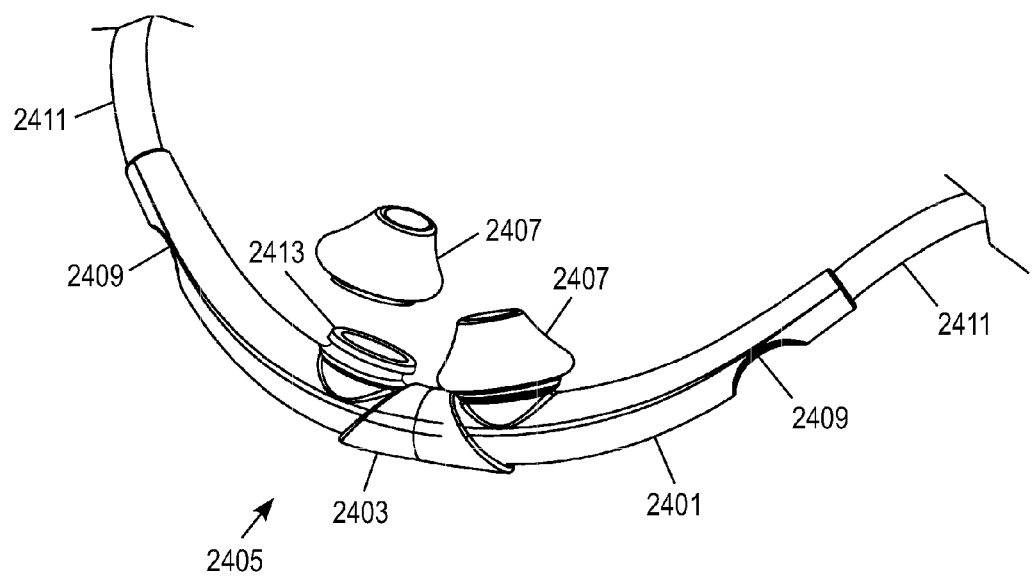
FIG. 25 shows that the nasal cushions may be removable.

FIG. 24 is a front view of a device with a flexible manifold 2401, according to one embodiment, in which a center portion 2403 of the manifold 2401 flexes to allow a more comfortable and or secure fit for the user. A nasal interface 2405 may include nasal cushions 2407, entrainment apertures 2409, and gas tubing 2411. FIG. 25 illustrates that the nasal cushions 2407 may be removable from stems 2413. The removable nasal cushions 2407 may allow for cleaning or customizing fit by replacing with more appropriate sized nasal cushions 2407.

Figure 26:
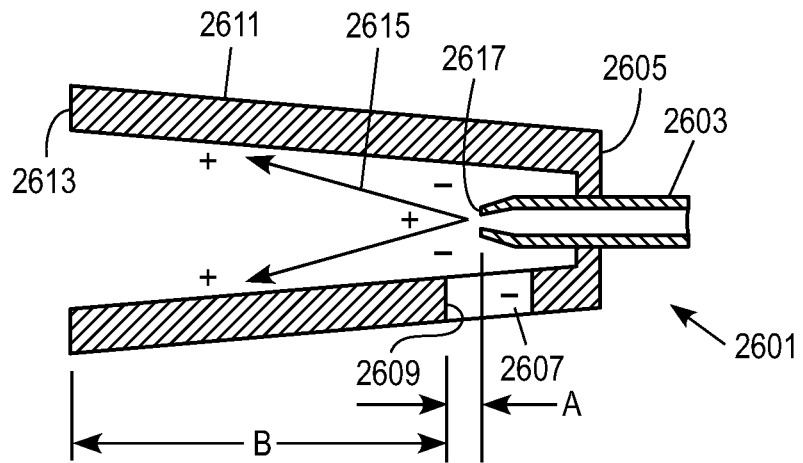
FIG. 26 is a schematic sectional view of a Venturi system embodiment of the invention, with the gas delivery nozzle protruding slightly distally from the proximal end of the entrainment window.

FIG. 26 is a schematic view of a section of a nasal mask manifold 2601, describing the basic dimensional relationships. One half of a nasal interface is shown, for example, the left side or the right side. A gas delivery jet nozzle 2603 is positioned near a proximal end 2605 of the manifold 2601 and proximal to a distal end 2609 of an entrainment aperture 2607. The gas delivery jet nozzle 2603 is shown positioned in parallel with the entrainment aperture 2607, rather than in series or coaxial. For purposes of this disclosure, parallel refers to gas flow direction. As such, the parallel position of FIG. 26 refers to the parallel flow of the ventilation gas delivered from the gas delivery jet nozzle 2603 and the flow of entrained ambient air through the entrainment aperture 2607.

The Venturi configuration of FIG. 26 may allow the device to accomplish several important things. First, it allows the nasal interface to be as small as possible because the gas delivery jet nozzle 2603 does not obstruct the spontaneous breathing path. If the gas delivery jet nozzle 2603 is in the spontaneous breathing path, the area around the gas delivery jet nozzle 2603 likely must be bigger to compensate for the space taken up by the gas delivery jet nozzle 2603 so that the flow path is not made too resistive. Additionally, the parallel entrainment aperture 2607 may allow the device to channel the gas flow away from the mouth. Also, locating the entrainment aperture 2607 parallel to the gas delivery jet nozzle 2603 may reduce the sound created by the gas delivery jet nozzle 2603. An outer tube 2611 can be a nasal cushion or a manifold 2601. The outer tube 2611 in the schematic is shown expanding from a proximal end 2605 to a distal end 2613, but it could have a constant cross section. Additionally, the outer tube 2611 may be straight or curved. The area included inside the gas delivery path being emitted from the nozzle, depicted by cone 2615, that is, inside and to the left of the cone 2615, may have positive pressure, and the area to the right of and outside of the cone 2615 may have negative pressure.

Dimension "A" is distance from a tip 2617 of the gas delivery jet nozzle 2603 to a distal end 2609 of the entrainment aperture 2607. Dimension "B" is a length of throat area of device. A+B should be kept to a minimum length while still (1) producing the entrainment desired, (2) producing the positive pressure desired, and (3) minimizing the overall size for user acceptance. Optimizing size, sound and output pressure and flow require an ideal dimension for A+B. Moving the gas delivery jet nozzle 2603 to the distal end 2609 of the entrainment aperture 2607, may set dimension A negative, which may require a commensurate increase in B, which is undesirable. Increasing A may move the gas delivery jet nozzle 2603 distally, and cause an increase in noise, which is undesirable. Positioning the tip 2617 of the gas delivery jet nozzle 2603 in the middle of the entrainment aperture 2607 may optimize pressure and flow performance while minimizing size and noise.

Figure 27:
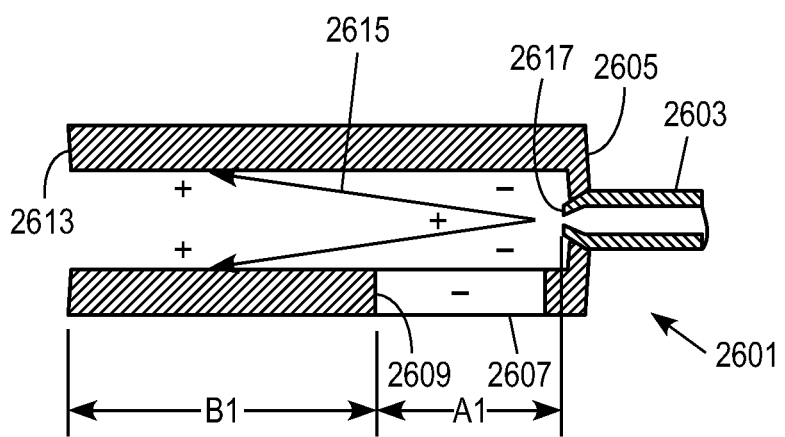
FIG. 27 is a schematic sectional view of a Venturi system embodiment of the invention, with the gas delivery nozzle proximal to the entrainment window.

FIG. 27 illustrates an alternate embodiment of FIG. 26 where increased sound levels are acceptable, and in which the gas delivery jet nozzle 2603 is positioned at the proximal end 2605 of the manifold 2601 and proximal to an entrainment aperture 2607. In this embodiment, A1+B1 from FIG. 27=A+B from FIG. 26, thus resulting in the same length but increasing sound.

Figure 28A:
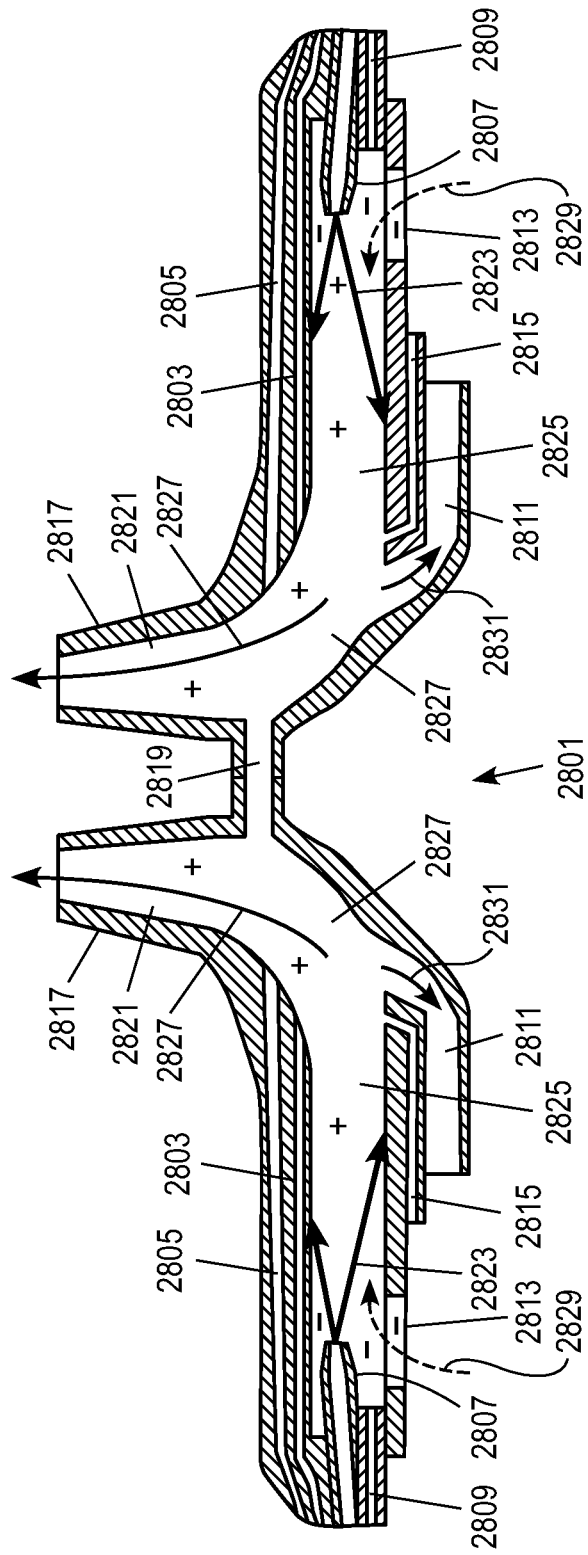
FIG. 28A is a schematic sectional view of a mask and a Venturi system embodiment, shown during gas delivery phase, with additional features for additional sound reduction, pressure balancing, flow measurement, gas sampling, pressure artifact dampening, and humidification delivery.

FIG. 28A is a schematic cross-sectional view of a nasal interface 2801, according to one embodiment. Multiple pressure sensing ports may be used, for example a first port 2803 and a second pressure sensing port 2805 to give the nasal interface 2801 the ability to also work as a pneumotach and determine flow rates and volumes flowing through the nasal interface 2801 during inhalation including gas from a gas delivery jet nozzle 2807 plus entrained air plus spontaneously breathed air, and during exhalation. Optionally, multiple pressure sensing port locations can be used by measuring an inspiratory phase signal in one ideal location and an expiratory phase signal in a different ideal location. Alternatively, an ideal location can be used to measure spontaneous breathing pressures while a second location can be used to measure the ventilation gas delivery pressure. A dampening feature (not shown) may be included near the pressure sensing ports to smooth out artifacts, for example a screen to produce eddy currents or flow dampening near the sensing port.

FIG. 28A describes the system during ventilation gas delivery, typically during the patient's spontaneous inspiratory phase and optionally during expiratory phase. Gas delivered by the ventilator through the gas delivery nozzles 2807 is depicted by arrows, ambient air entrained is depicted by 2829, gas being delivered to the patient is depicted by 2827, and surplus gas depicted by 2831 is directed out of the nasal interface 2801 through the exhaled gas exhaust port to prevent the surplus gas 2831 from colliding with gas being delivered by the nozzles 2807 and gas being entrained by the delivered gas 2829. Surplus gas 2831 may occur when gas is being delivered to the patient after inspiration has been completed, or during periods when the prevailing conditions downstream inside the patient's respiratory tract generate enough back pressure to cause gas flow to move at least in part away from the nose. Positive pressure is created inside and distal to the cone of flow 2823 emitted from the gas delivery nozzles 2807, and negative pressure is created outside and proximal to this cone of flow 2823.

Figure 28B:
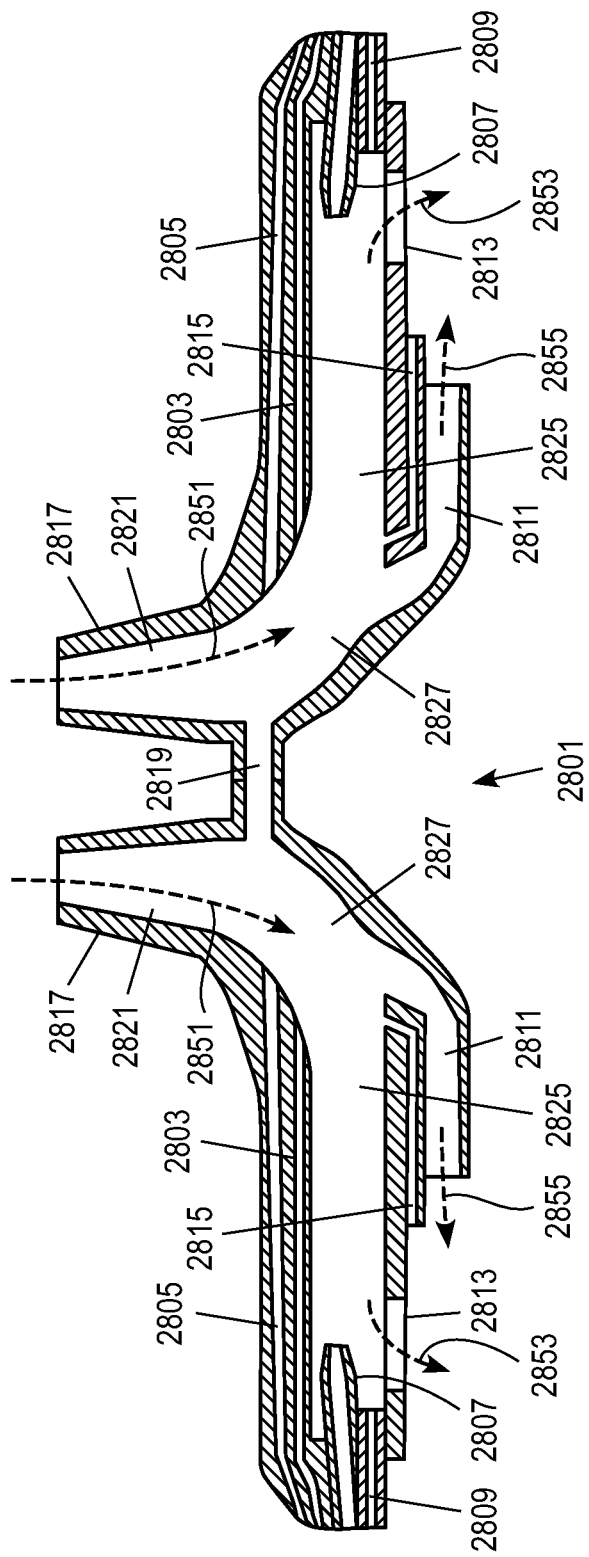
FIG. 28B shows the mask of FIG. 28A shown during an expiratory phase when gas delivery is off.
Figure 29:
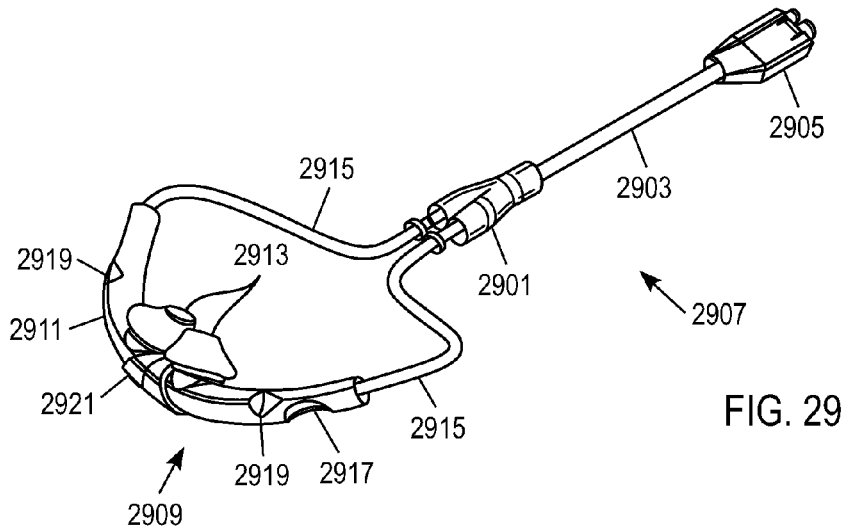
FIG. 29 is a perspective view of the nasal mask assembly of FIG. 16, but including a flexible center portion as shown in FIG. 24.
Figure 30:
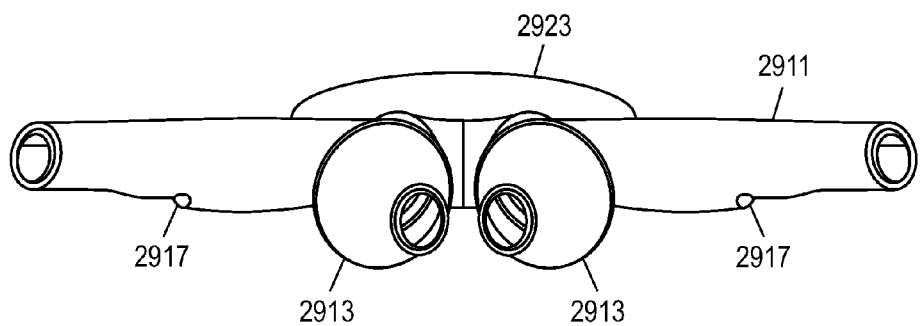
FIG. 30 is a top-posterior view of the mask of FIG. 16, with an optional posterior side skin positioning cushion.
Figure 31:
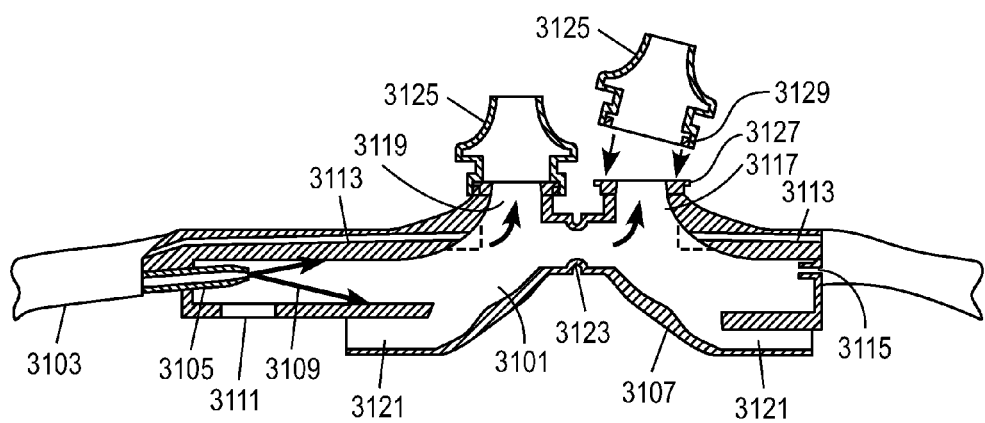
FIG. 31 is a schematic view of an optional embodiment in which the ventilation gas is delivered to one side of the mask, with other features including a snap fit nasal cushion and a flex joint in the mask between the cushions.

FIG. 28B describes the nasal interface 2801 of FIG. 28A when the gas delivery is off, typically during the patient's spontaneous expiratory phase. Gas exhaled by the patient 2851 can exit 2853 through the entrainment aperture 2813 and/or exit 2855 through the exhaled gas exhaust path 2811.

An angled gas delivery jet nozzle 2807 may further reduce sound generation. An exhaled gas exhaust path 2811 or return path divides delivered flow and exhaust flow to reduce sound generation caused by shearing. An entrainment aperture 2813 is positioned distal to or in part distal to the gas delivery jet nozzle 2807. One or more gas sampling ports 2815 may be located in the nasal interface 2801, such as for ETCO2 or FIO2 sampling. Nasal cushions 2817 may be located at gas flow path distal ends 2821. The gas flow path distal ends 2821 may or may not be connected by a channel 2819. Positive pressure which is created inside of a gas delivery cone of flow 2823 is created in the substantially constant cross-sectional area throat section 2825, before the gas flow path begins to curve 2827 superiorly toward the gas flow path distal ends 2821.

Humidification can be added to the gas delivery circuit, either by active heated humidification or by aerosolizing liquid particles into the gas delivery system, typically into the nasal interface 2801 or by adding a heat moisture exchanger (HME) to the manifold gas exit path or combinations of the above. To prevent rainout from occurring in the nasal interface 2801, the nasal interface 2801 may have a drainage line (not shown) to scavenge any moisture that is collecting. A humidification/aerosol injection port 2809 is preferably located in a negative pressure zone so that the aerosol can enter the nasal interface 2801. If the humidification/aerosol injection port 2809 was in a positive pressure zone, the pressure would prevent the humidified gas or aerosol from entering the nasal interface 2801. Alternately, a heat moisture exchanger (HME) (not shown) may be coupled with exhaled gas exhaust path 2811 or entrainment aperture 2813.

FIG. 29 is an isometric view of a nasal mask assembly 2907, with a nasal mask 2909, which includes the mask manifold 2911, nasal cushions 2913, bilateral gas delivery tubing 2915, entrainment apertures 2917, exhaust ports 2919, flexible connector 2921, a Y-connector 2901, a gas delivery circuit 2903, and a ventilator connector 2905.

FIG. 30 is a top view of the device of FIG. 29 with the optional embodiment of a skin cushion 2923 which may also serve as an angle adjustment cushion. The skin cushion 2923 can be made of a soft elastomeric or viscoelastic material that conforms to the user's face under their nose, and can be used to cushion and dissipate any forces of strapping the nasal mask 2909 and manifold 2911 to the user's face. The skin cushion 2923 can be used to space the manifold 2911 at the appropriate distance from the skin so that the distal end gas flow openings in the manifold 2911, or nasal cushions 2913 if included, are properly aligned with the entrance to the nose and the nasal foramen in the saggital plane. The skin cushion 2923 can be removably attachable for cleaning or replacement if dirty, and available in different sizes to set the correct angle. The shape of the skin cushion 2923 shown is convex at the posterior side; however, the skin cushion 2923 can be concave to match the curvature of the user's skin, or flat. Alternately, the skin cushion 2923 can create multiple separate contact points with the skin, for example, at a point directly under the nose, and at two additional points on each lateral side of the nose. The surface of the skin cushion 2923 may be treated with a special surface to prevent it from irritating the user's skin or causing ulcerations, such as with a lubricous coating, such as a hylauronic acid coating or hydrophilic coating, and can be dimpled so that air pockets can form between the skin cushion 2923 and skin, to avoid drying out of the skin.

FIG. 31 is a cross sectional diagram through a gas flow path 3101 of an optional embodiment in which gas delivery tubing 3103 and a gas delivery nozzle 3105 connect to only one side of the mask's manifold 3107 to create a unilateral design. Gas enters the manifold 3107 from the gas delivery nozzle 3105 on one side, left side of FIG. 31 although the sides may be reversed, of the manifold 3107 and generates negative pressure on the proximal side of a Venturi gas flow cone 3109. Air may be entrained through an entrainment port 3111 on the left side of the manifold 3107. Positive pressure may be created inside the manifold 3107 on the right side of the Venturi cone 3109. The positive pressure in the manifold may be measured in the left and right side of the manifold 3107 by the pressure sensing lumens 3113 and ports 3115. Gas may flow out of manifold distal end gas flow openings 3117, 3119. The left distal end gas flow opening 3119 can be more restrictive than the right side distal end gas flow openings 3117 so as to direct an equal amount of flow to the right side distal end gas flow opening 3117 and balance the gas output between the left and right openings. The manifold 3107 may include secondary gas flow path for exhaust 3121 on both the left and right side of the manifold 3107, or just the left or just the right side of the manifold 3107. The mask may include a humidification delivery port, as shown in FIG. 28, or a gas sensing composition port, a flex joint 3123 to flex the included angle between the left and right gas distal end gas flow openings 3117, 3119 or nasal cushions 3125, if included. The nasal cushions 3125, if included, can be removably attachable from mating connection features 3127, for cleaning, replacement or adjustment. The nasal cushions 3125 can include a semi-rigid or rigid ring 3129 at or near its proximal end base which snaps over or onto a mating connection feature 3127 or boss on the manifold 3107. The ring 3129 can be a complete 360 degree ring or a partial incomplete ring. The nasal cushions 3125 can be rotationally adjustable on the manifold 3107, and can optionally have detent settings for facilitating a correct rotational setting.

The dimensions of key functional features may be selected and varied to optimize the primary critical performance attributes such as sound, entrained flow, and output pressure. Functional features may include, but are not limited to: throat length and diameter, input pressure to the gas delivery nozzle, input flow rate to the gas delivery nozzle, nozzle exit diameter, nozzle end internal diameter radius, gas exit velocity from the gas delivery nozzle, breathing resistance of the mask, entrainment aperture size, gas delivery jet nozzle distance to the entrainment aperture, gas delivery nozzle distance to the throat entrance, exhaust flow path cross sectional area, gas delivery nozzle, and gas delivery nozzle concentricity.

Because the dimensions of functional features may compete with one another in a way that can oppositely affect performance attributes, these variables preferably must be balanced to create a successful device. If throat diameter is decreased, pressure and flow can increase, however, breathing resistance may increase, which is undesirable. If the gas delivery jet nozzle is moved further away from the throat, pressure and entrainment may increase, however, noise may also increase, which is undesirable. If the entrainment aperture cross sectional area is increased, entrainment can increase, however, a bigger overall device may be needed to accommodate the larger entrainment aperture. The entrainment aperture is dimensioned such that it is about 0-50% and preferably about 10-20% more than the minimum cross sectional area of the throat section to ensure that the entrainment aperture does not restrict breathing resistance, and to optimize entrainment while limiting the overall size of the device. If the entrainment aperture location is at the proximal end of the device, approximately a 2-5× entrainment factor can be achieved (3 to 5 times more entrained flow than delivered flow). If the entrainment aperture is on a side of the device, approximately a 1-3× entrainment factor can be achieved. The side configuration may be selected to optimize the balance between output and the intended application in which it is desired to direct exhaled flow in a natural direction away from the face. If the gas delivery jet nozzle diameter is reduced, the exit velocity can increase and the entrainment can increase, however, this can reduce the output pressure, so a balance is selected. The overall length is selected so that fully developed positive pressure flow is achieved before the flow path turns to the nasal cushions section of the nasal interface, for optimal flow and pressure performance.

Embodiments of the present invention may achieve up to 35 cmH2O lung pressure (output pressure) and up to 150 LPM total flow (delivered flow plus entrained flow), and a sound level of approximately 30-60 db, with the following configuration variables. The tables list exemplary values only and are not to be construed as limiting the disclosure.

TABLE 1

Nasal Mask Exemplary Key Dimensions and Values

| Feature | Preferred/ideal | Range |
|---|---|---|
| Nozzle diameter: | 0.033" | .010-.050 |
| Flow rate delivered to nozzle: | 30 lpm | 6-40 lpm |
| Input pressure delivered to nozzle: | 35 psi | 5-60 psi |
| Throat length: | 1.9" | 1.0-3.0" |
| Throat typical cross sectional area: | 0.04 in$^2$ | 0.02-0.06 in$^2$ |
| Entrainment aperture cross sectional area: | 0.06 in$^2$ | 0.04-0.08 in$^2$ |
| Nozzle distance to proximal edge of entrainment window: | 0.19 in | 0.10-0.30 in |
| Nozzle distance to throat area: | 0.07 in | 0.05-0.09 in |

TABLE 2

Exemplary Ventilatory Support Parameters

| Parameter | Range | Preferred (Adult*) |
|---|---|---|
| Lung Volume Augmentation (%) | 10-150% | 15-65% |
| WOB reduction (%) | 5-80% | 10-50% |
| Lung Pressure increase (cwp) | 1-30 | 3-20 |
| Upper Airway pressure increase (cwp) | 3-34 | 7-25 |
| Lung Pressure or Volume Waveform | — (1) | R |
| Entrained ambient air (% of Ventilator gas delivery) | 20-200% | 50-100% |
| Gas exit speed out of gas delivery nozzle (m/sec) | 25-300 | 50-200 |
| Ventilator Output flow rate, average (lpm) | 5-40 | 10-20 |
| Gas Delivery Tubing outer diameter (mm) | 3-7 | 4-6 |
| Ventilator Output Pressure (psi) | 10-60 | 20-40 |
| Ventilator Drive Pressure (psi) | 10-80 | 20-50 |
| Ventilator Operating Pressure (psi) | 5-40 | 25-35 |
| Ventilator Output Volume (ml) | 25-750 | 50-350 |
| Ventilator Output Pulse Time (sec.) | 0.100-1.200 | 0.200-1.200 |
| Therapy's nominal source gas consumption (lpm) | 0.5-6.0 | 2-3 |
| Ventilator Output Synchronization (ms) | variable depending on comfort and need (25-500 ms delay) | variable depending on comfort and need (75-250 ms delay) |
| Ventilator Output Waveform | (1) | Descending |

TABLE 3

Sleep Apnea Parameters

| Parameter | Range | Preferred (Adult*) |
|---|---|---|
| Airway Pressure (cwp) | 0-30 | 5-25 |
| Lung Pressure increase (cwp) | 0-20 | 4-20 |
| Upper Airway pressure increase (cwp) | 3-30 | 7-20 |
| Lung Waveform | (1) | Rounded |
| Tubing outer diameter to patient (mm) | 3-7 | 4-6 |
| Entrained ambient air (%) | 20-200% | 50-100% |
| Gas exit speed out of patient interface (m/sec) | 25-300 | 50-200 |
| Ventilator Output Pressure (psi) | 5-40 | 25-35 |
| Ventilator Output flow rate, average (lpm) | 5-40 | 10-20 |
| Ventilator Operating Pressure (psi) | 10-80 | 20-50 |
| Ventilator Output | Continuous, intermittent or multilevel continuous | Continuous, intermittent or multilevel continuous |
| Ventilator Intermittent mode Output Volume per breath (ml) | 50-1000 | 60-500 |
| Ventilator Intermittent mode Output Pulse Time (sec.) | 0.250-2.000 | 0.400-1.50 |
| Ventilator Intermittent mode Output Waveform | (1) | Descending |

NOTES:
*Pediatric and neonatal: Pressure and volume values are 25-75% less (Ped) and 50-90% less (Neo).
(1) Square, Rounded, Descending, Ascending, Sinusoidal, Oscillating.

TABLE 4

Additional Exemplary Dimensions, Values and Materials

| Feature Dimensions | Range | Preferred Range |
|---|---|---|
| Gas delivery hose, ID (mm) | 2.0-7.0 | 2.5-4.5 |
| Gas delivery hose, Length (ft), ambulating with wearable system | 2-6 | 2.5-4 |
| Gas delivery hose, Length (ft), ambulating with stationary system | 20-75 | 40-60 |
| Gas delivery hose, Length (ft), sleeping | 4-15 | 6-10 |
| Nozzle, ID (mm) | 0.25-2.0 | 0.05-1.75 |
| Nozzle, Length (mm) | 1.0-30 | 4-12 |
| Nozzle distance to nose (and/or centerline of manifold) (mm) | 5-60 mm | 15-40 mm |
| Manifold Length (mm) | 20-160 mm | 30-80 mm |
| Manifold throat cross sectional area ($in^2$) | .015-.080 | .025-.050 |
| Manifold gas flow path volume | 2-12 ml | 3-6 ml |
| Manifold Pillow opening CSA ($in^2$) | .040-.120 | .065-.105 |
| Manifold pressure sensing line diameter (in) | .015-.055 | .025-.045 |
| Manifold sound reducing return vent CSA ($in^2$) Should be $1/5^{th}$ to $2/3^{rd}$'s the area of the manifold entrainment port | .002-.050 | .005-.020 |
| Manifold breathing resistance ($cmH_2O$ @ 60 lpm) | 1-4 | 1.5-2.5 |
| Breathing sensing port, distance to nose (mm) | −5-30 | 0-20 |
| Angle adjustment in front plane between nozzles and/or outer tubes | Parallel to 45 degree included angle | 5-20 degree included angle |

| Materials | Types | Preferred |
|---|---|---|
| Gas delivery hose | PP, PE, PS, PVC | PE |
| Cannula | PU, PVC, Silicone | PVC, Silicone |
| Manifold | PVC, Silicone, PU, PE, Polysolfone | PVC, Silicone |
| Jet Nozzle | Metal, Ultem, Nylon, LCP, PVC, PC, ABS, PEEK | PVC |
| Pillows | PVC, Silicone, PS | Silicone |
| Attachment and Positioning Pad | Silicone, Foam | Silicone |

Dimensions listed are exemplary and for average sized adults; pediatric sizes 20% less, neonatal sizes 50% less.
Diameters listed are effective diameters (average cross sectional dimension).

Figure 32:
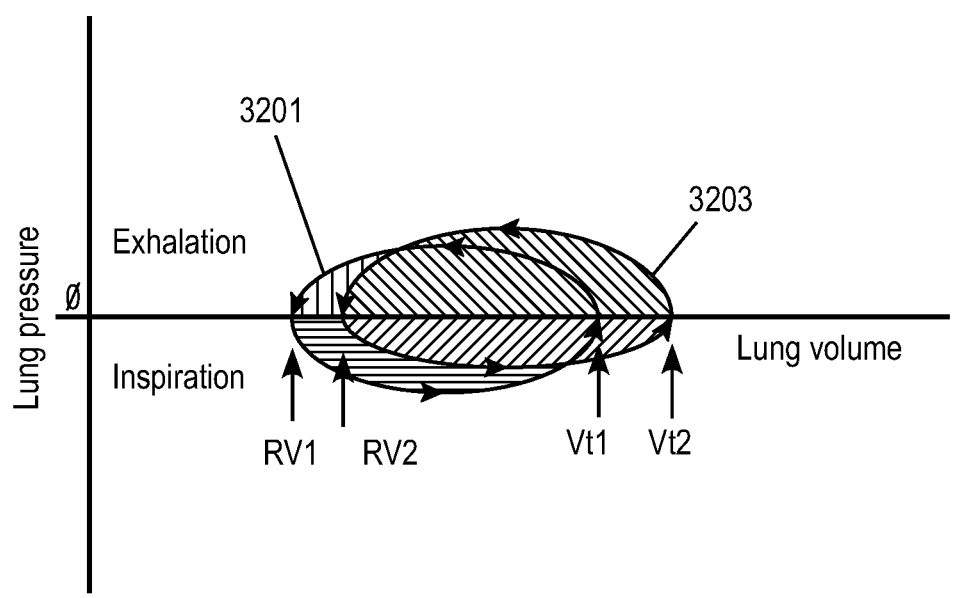
FIG. 32 graphically shows how the patient's work of breathing may be beneficially affected by the invention when the invention is used for lung disease or neuromuscular disease applications.

FIG. 32 describes the mechanism of action of the invention, and how the patient's work of breathing may be beneficially affected by the invention, when the invention is used for lung disease or neuromuscular disease applications. The patient's lung volume may be graphed as a function of lung pressure, the area inside the curve representing work, typically expressed in Joules per Liter (J/L), and for a normal healthy adult can be 0.3-0.6 J/L. For a respiratory compromised patient, 4-10 times more work can be required to breathe during rest, and even more during exertion, to overcome the diseased state of the tissue, for example to overcome static and dynamic hyperinflation as in the case of COPD, or to overcome high airways resistance as in the case of fibrosis or ARDS.

In the graph shown, the area inside the curve below the pressure axis is the inspiratory WOB, and the area defined by the area inside the curve above the pressure axis is the expiratory WOB. The arrows show the progression of a single breath over time, starting from RV to VT then returning from VT to RV. RV1 and VT1 are the residual volume and tidal volume without the therapy. Line 3201 represents spontaneous breathing without non-invasive open nasal ventilation. Line 3203 represents spontaneous breathing with non-invasive open nasal ventilation, with inspiratory augmentation and positive end-expiratory pressure (PEEP) therapy. RV2 and VT2 are the residual volume and tidal volume with the therapy. As can be seen, RV increases with the therapy because in this example, expiratory flow is provided as part of the therapy, which may increase residual volume. Importantly, VT is increased with the therapy and is increased more that the RV is increased, indicating that more volume is entering and leaving the lung as a result of the therapy. The increase in tidal volume is considered clinically efficacious, however is technically challenging to achieve in an open ventilation, non-invasive and minimally obtrusive system. As is shown in the graph, the patient's inspiratory WOB with the invention ON may be about 25% less than the patient's inspiratory WOB with the invention OFF. Also, inspiratory lung pressure increases (is less negative) and tidal volume increases, and optionally exhaled pressure increases if the therapy is provided during exhalation. While residual volume increases in the example shown because the ventilator is providing gas in this example during the expiratory phase, the ventilation parameters can be titrated to not effect residual volume, and because of the ability of the patient to exercise their lung muscles when receiving the therapy, the patient's lung mechanics may remodel in the case of COPD, actually causing a reduction of residual volume to a more normal value. In the graph shown, the waveform with therapy assumes an early inspiratory trigger time for the ventilator inspiratory phase therapy output, and that the volume output is delivered within the patient's inspiratory time. Optionally, however, different delivery waveforms and delivery synchronizations can be performed, which may adjust the WOB curve. For example, the ventilator inspiratory phase therapy can be delivered late in the person's inspiratory cycle, with delivery completing at the end of inspiration, and delivered with a square or ascending waveform profile. In this case the WOB curve with therapy will be tilted upward to the right of the curve, such that inspiration ends and transitions to exhalation at a point above the lung pressure zero axis.

Figure 33:
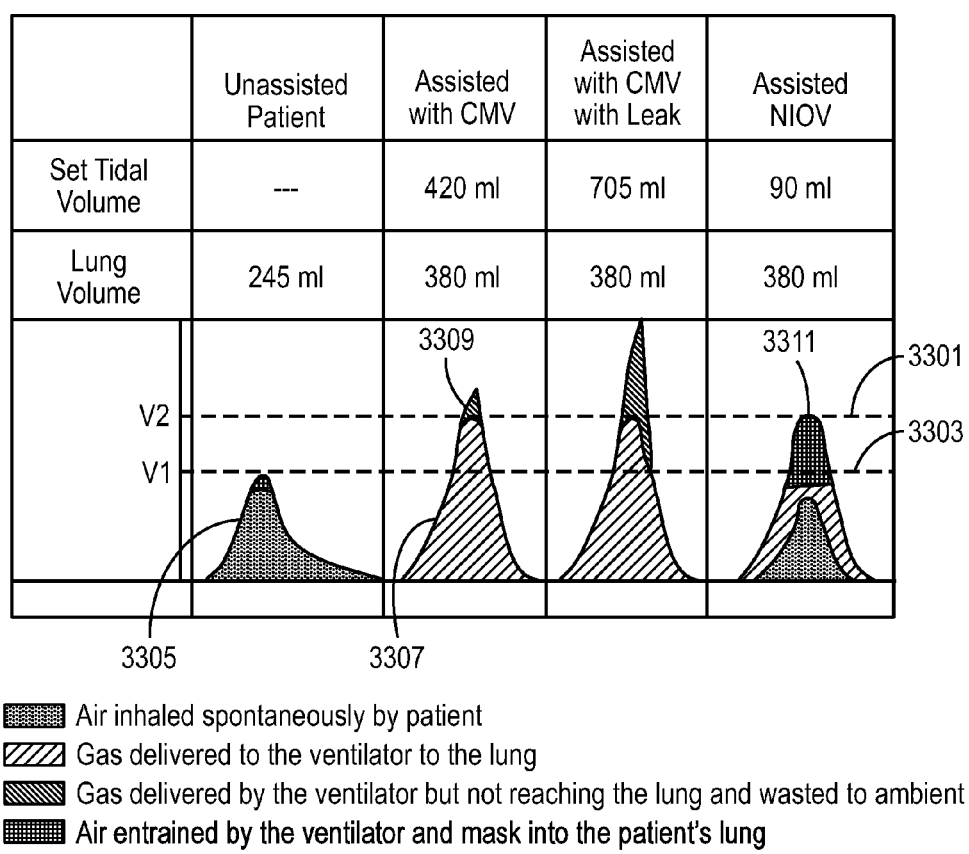
FIG. 33 graphically shows lung volume on the x-axis and lung pressure on the y-axis to illustrate how the lung volumes achieved with NIOV on a lung simulator bench model in comparison to conventional ventilation.

FIG. 33 graphically illustrates the lung volumes achieved with NIOV on a lung simulator bench model in comparison to conventional ventilation. In all the waveforms the simulated patient is spontaneously breathing at the same inspiratory effort which results in a tidal volume of 245 ml, and the clinical goal is to increase the patient's tidal volume from 245 ml 3301 to 380 ml 3303. In the first waveform from left to right in the graph, the patient's breath 3305 is un-assisted and thus the patient receives a tidal volume of 245 ml. In the next waveform, the simulated patient with the same effort is assisted with a traditional closed system ventilator, such as with a sealed breathing mask or cuffed airway tube. The ventilator output 3309 is set to a level to achieve the desired "assisted" tidal volume of 380 ml. The ventilator is set to 420 ml to achieve this goal, as there is a discrepancy between the gas delivered to the lung by the ventilator versus the gas delivered by the ventilator but not reaching the lung and wasting to ambient 3307. In the third waveform, a small leak is introduced in the conventional ventilator system, such as would be done in the case of weaning the patient off of the ventilator. To achieve the desired "assisted" tidal volume of 380 ml, the ventilator must now be set at 705 ml. In the second and third waveforms, it can also be seen that all of the volume received by the patient's lung originates from the ventilator, which it must in these conventional systems. In the forth waveform, the patient is assisted with the NIOV, and as can be seen, the NIOV ventilator output only has to be set at 90 ml to achieve desired "assisted" level of 380 ml. In this case, only some of the 380 ml tidal volume comes from the ventilator, and a substantial portion of the 380 ml comes from entrainment and spontaneously inspired ambient air 3311, therefore making the NIOV system far more efficient, comfortable, and healthier, than the other systems.

Figure 34:
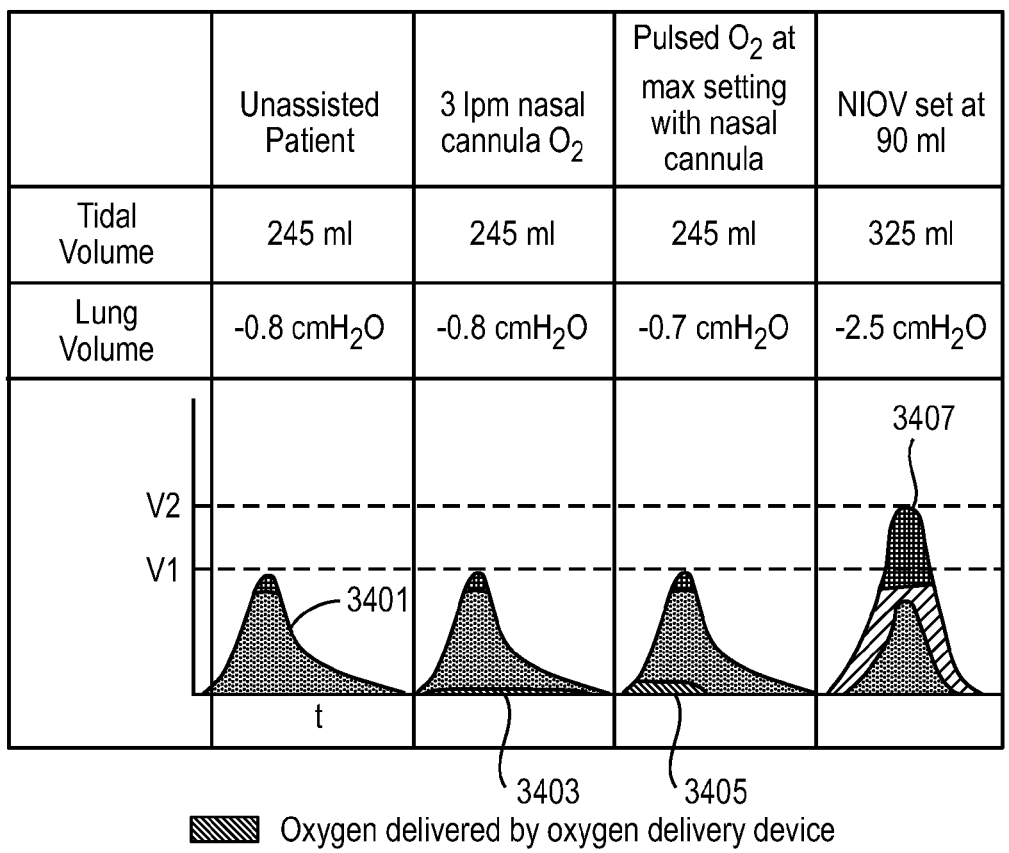
FIG. 34 graphically illustrates the lung volumes achieved with NIOV in comparison to oxygen therapy, using the lung simulator bench model.

FIG. 34 graphically shows NIOV in comparison to oxygen therapy, using the lung simulator bench model. In the first waveform on the left, the patient is unassisted and breathes at an effort of –0.8 cmH2O, generating 248 ml of inspired tidal volume 3401. In the second waveform and third waveform, the patient receives continuous flow 3403 and pulsed flow 3405 of oxygen respectively via nasal cannula, with no or negligible effect on lung pressure and tidal volume. In the forth waveform, NIOV 3407 is used which shows a marked increase in lung pressure and tidal volume, thus indicating that NIOV helps in the work-of-breathing as described earlier, despite the fact that NIOV is an open airway system.

FIGS. 35A-35L show exemplary ventilation gas delivery profiles of the invention and their respective effect on lung volume and lung pressure.

FIGS. 35A, 35D, 35G and 35J show exemplary pressure and/or flow waveforms delivered by the ventilator. FIG. 35A describes a square waveform 3501 delivered during the complete inspiratory cycle; FIG. 35D describes an ascending and descending waveform 3503; FIG. 35G describes a square waveform 3507 delivered for the first part of the patient's spontaneous inspiratory time; FIG. 35J shows a multilevel amplitude waveform 3509 with a first amplitude 3511 delivered during the inspiratory phase and a second amplitude 3513 during the expiratory phase, where the second amplitude 3513 for example is used to deliver positive end-expiratory pressure (PEEP), which in some clinical applications will be efficacious. Other waveforms are also included in the invention, such as a descending trapezoidal or ascending trapezoidal square wave. The pressure and flow rate output from the ventilator into the gas delivery tubing is typically in the 5-40 psi and 6-30 lpm range.

FIGS. 35B, 35E, 35H and 35K describe the lung volume being delivered by the therapy including a ventilator output 3515 and an entrained volume 3517.

FIGS. 35C, 35F, 35I and 35L show the lung pressure without therapy represented by the dashed line 3519, and the resultant lung pressures with the therapy represented by the solid line 3521, showing a positive inspiratory pressure in FIG. 35C for the entire inspiratory phase, a positive inspiratory pressure for part of the inspiratory phase in FIGS. 35F and 35I, with therapy extending into exhalation 3523, and an elevated negative inspiratory pressure in FIG. 35L.

FIGS. 36A-36L describe additional exemplary ventilation gas delivery profiles of the invention and their respective effect on lung volume and lung pressure.

Figure 36A:
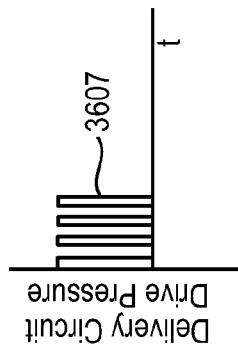
FIG. 36A graphically shows an ascending waveform gas delivery pressure, according to one embodiment.
Figure 36D:
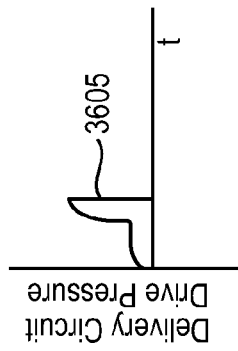
FIG. 36D graphically shows a descending waveform gas delivery pressure, according to one embodiment.
Figure 36J:
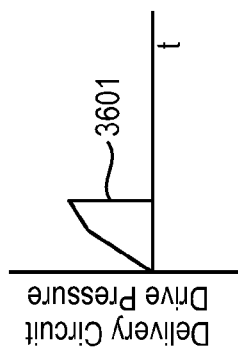
FIG. 36J graphically shows an oscillatory waveform gas delivery pressure, according to one embodiment.
Figure 36B:
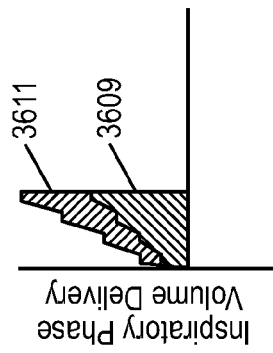
FIG. 36B graphically shows the volume delivery of FIG. 36A.
Figure 36E:
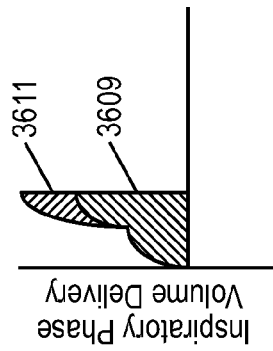
FIG. 36E graphically shows the volume delivery of FIG. 36D.
Figure 36H:
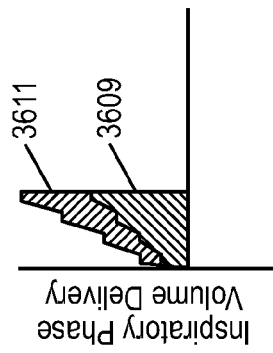
FIG. 36H graphically shows the volume delivery of FIG. 36G.
Figure 36C:
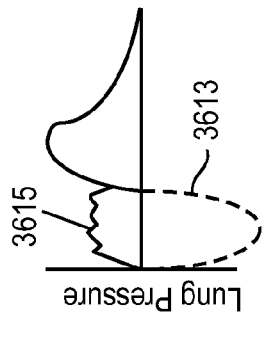
FIG. 36C graphically shows resulting lung pressure of FIG. 36A.
Figure 36F:
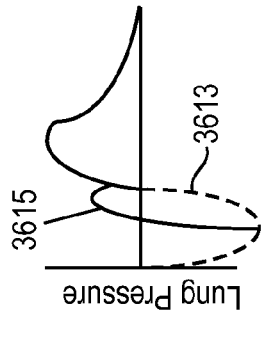
FIG. 36F graphically shows resulting lung pressure of FIG. 36D.
Figure 36I:
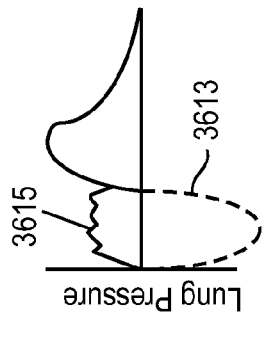
FIG. 36I graphically shows resulting lung pressure of FIG. 36G.
Figure 36G:
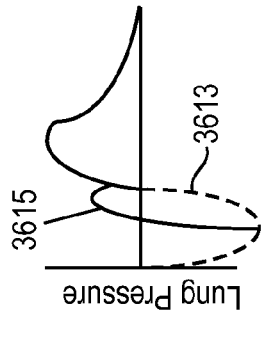
FIG. 36G graphically shows a two-stage amplitude waveform gas delivery pressure for a portion of the inspiratory phase, according to one embodiment.
Figure 36K:
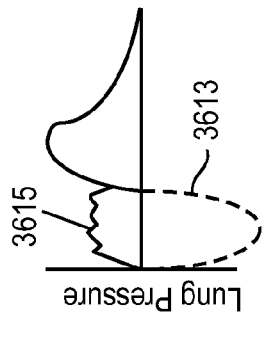
FIG. 36K graphically shows the volume delivery of FIG. 36J.
Figure 36L:
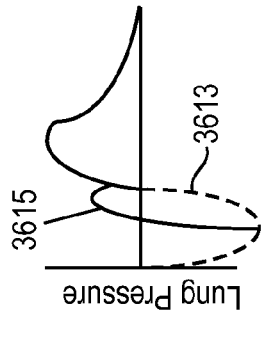
FIG. 36L graphically shows resulting lung pressure of FIG. 36J.

FIG. 36A describes an ascending waveform 3601. FIG. 36D describes a descending waveform 3603. FIG. 36G describes a multi-level waveform 3605 with a lower amplitude in the first portion of the inspiratory phase, for example to deliver the necessary oxygen molecules to the lung early in the breath phase, and a higher amplitude in the second portion of the inspiratory phase, for example to deliver the mechanical support portion of the therapy to help the work of breathing. FIG. 36J describes an oscillatory waveform 3607, which may be use the gas supply more efficiently while producing nearly the same Venturi, entrainment and therapeutic effect.

FIGS. 36B, 36E, 36H and 36K describe the lung volume being delivered by the therapy including a ventilator output 3609 and an entrained volume 3611.

FIGS. 36C, 36F, 36I and 36L show the lung pressure without therapy represented by the dashed line 3613, and the resultant lung pressures with the therapy represented by the solid line 3615.

The lung pressure resulting from the therapy may be governed by a combination of factors: the gas delivery circuit pressure, the jet pump design and configuration, the patient's lung compliance and airway resistance, the patient's breathing effort, the timing of the ventilator output relative to the patient's inspiratory phase, and the ventilator output waveform. Typically, however, a gas delivery circuit pressure of 30 psi delivering 100 ml with a square waveform, and delivered for 500 msec starting at the beginning of the patient's inspiratory phase, may increase lung pressure by 5-15 cmH2O. And, typically a gas delivery circuit pressure of 30 psi delivering 250 ml with a trapezoidal waveform, and delivered for 700 msec during the majority of the patient's inspiratory phase, may increase lung pressure by 10-25 cmH2O. The gas delivered by the ventilator can be oxygen, air, oxygen-air mixtures, or therapeutic gases such as helium. In a main mechanism of action of the invention, the patient's lung pressure and lung volume is increased, which allows the patient to exert them self without being limited by fatigue and dyspnea. In another main mechanism of action of the invention, the patient reduces their breathing effort in response to the pressure and volume support provided by the therapy, thus resulting in no change in total lung volume from the therapy, but resulting in a reduced work of breathing. In another main embodiment of the invention, a combination of the above two mechanisms of action can occur.

Figure 37:
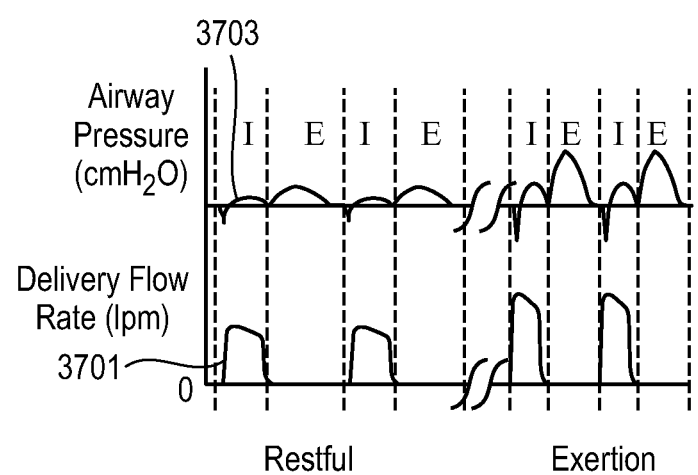
FIG. 37 graphically shows the timing and amplitude of a breath frequency modulated gas flow amplitude delivery, according to one embodiment.

FIG. 37 is a diagram of timing and gas flow delivery, according to one embodiment. Amplitude of gas flow delivery rate 3701 modulates with respiratory rate to affect airway pressure 3703. The faster the respiratory rate, the higher the amplitude. The volume delivery may be maintained at a constant rate, unless changed by the user, between the restful state and exertion state. However, the amount of power delivered by the system may be higher during the exertion state, because the faster flow rate entrains more gas, which produces more power and higher lung pressures during inspiratory phase. Further, the delivery time of the delivered flow can be adjusted by the user as a percentage of the breath period. For example, if the breath period is 3 seconds, a 25% delivery time setting would equal a delivered flow pulse width of 0.75 seconds. The delivered flow pulse width would change with the breath rate; however, it may continue to be 25% of the breath period (unless changed by the user). The setting can be set for example in the range of 15% to 70% of the breath period. The setting may be independent of the volume setting. For example, a setting of 25% versus 40% may still deliver the same set volume, and may merely deliver the set volume at different flow rates. The algorithm for adjusting the delivered flow pulse time may, for example, look at the preceding 3 to 5 breaths to determine what the current breath period is, and may have a correction factor to rule out outlier breaths.

Figure 38:
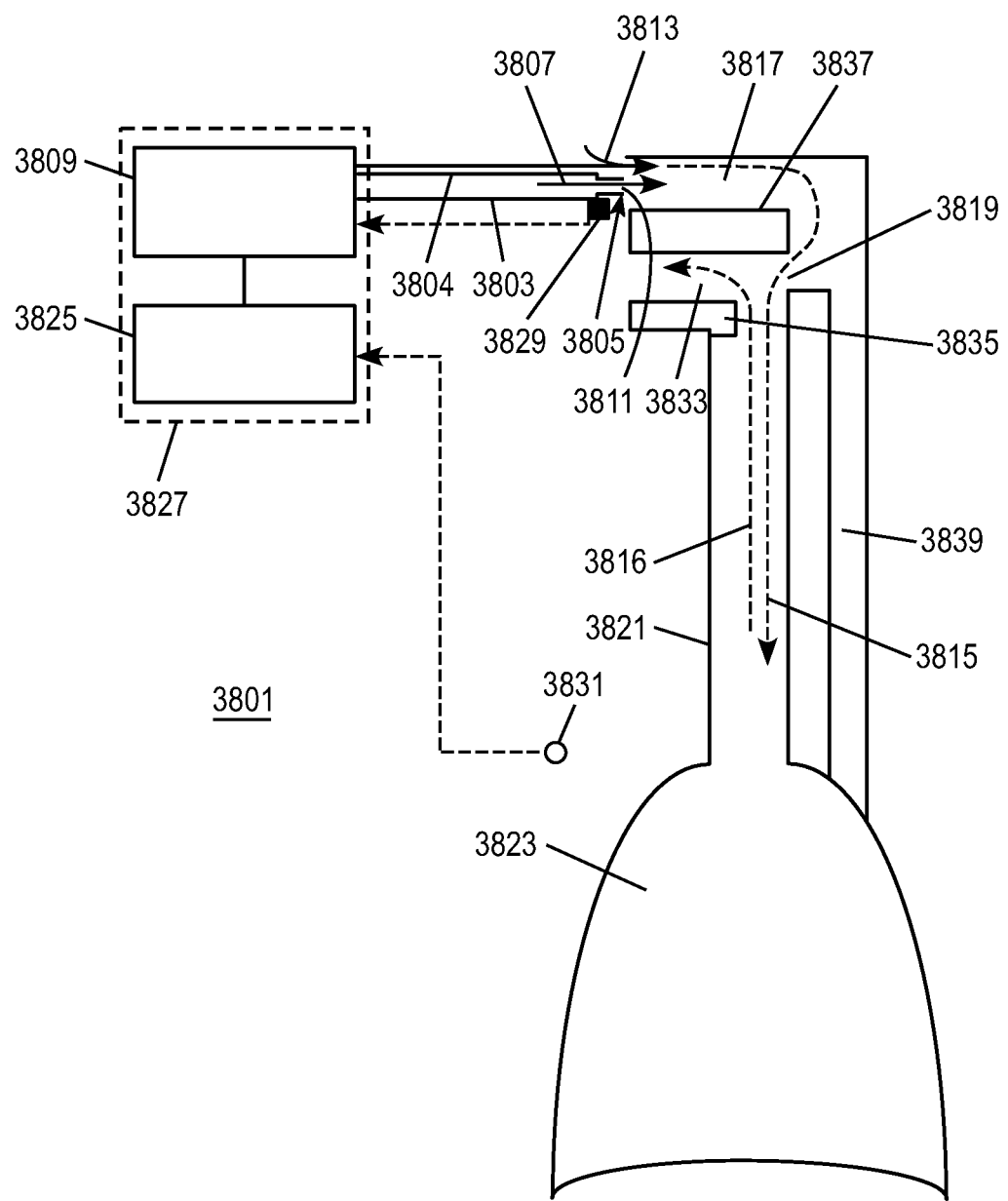
FIG. 38 describes a system schematic diagram when the invention is used for treating sleep apnea.

FIG. 38 describes a schematic diagram of an exemplary overall system 3801 when used to treat sleep apnea. In this embodiment, a ventilator 3809 delivers gas to a nasal interface 3805 from a gas generating system 3825, such as a scroll pump.

A patient may be ventilated with non-invasive open ventilation (NIOV) using a ventilation gas delivery circuit 3803, an airway pressure sensing line 3804, and non-sealing nasal interface 3805. The nasal interface 3805 preferably does not seal against the patient's nose such as is typical with other ventilation interfaces, and rather leaves the nose open for the user to breathe normally and freely from the ambient surroundings. Ventilation gas 3807 delivered from a ventilator 3809 may travel through the ventilation gas delivery circuit 3803 and out one or more gas exit ports 3811 in the nasal interface 3805. The ventilation gas 3807 may exit at a speed that entrains ambient air 3813, such that the combination of ventilation gas 3807, entrained ambient air 3813 and spontaneously inhaled air 3815, if the patient is spontaneously breathing, is delivered to the patient's airways, such as the nasal cavity 3817, oropharyngeal airway 3819, trachea 3821, lung 3823 and others, under power to create a clinically efficacious effect on the lung and airways. Patient may exhale 3816 through the nose or mouth.

The nasal interface 3805 geometry and dimensions may optimize the physics and fluid dynamics of the system to maximize performance, and user acceptable and tolerability. The performance of the system may create an increase in lung volume, or increase in lung pressure, or reduction in the work-of-breathing of the user, or increase in airway pressure.

The NIOV ventilation system may also include the ventilator 3809 in fluid communication with a gas supply or gas generating system 3825. The ventilator 3809 and/or gas supply or gas generating system 3825 may be separate or in a single ventilation system 3827. Ventilation gas 3807 can be oxygen as in the case of respiratory insufficiency applications, air in the case of sleep apnea or neuromuscular applications, combinations thereof, or any other clinically beneficial gas. The ventilator 3809 may have a control unit or system. The ventilator 3809 may be powered on and may have a delay of a predetermined time prior to supplying ventilation gas 3807. After a predetermined time, the ventilator 3809 may deliver gas as needed, such as in synchrony with a breathing pattern.

A spontaneous breathing respiration sensor 3829 may also be used to detect, determine and measure the spontaneous breathing pattern and phases of the patient, as well as apnea or hypopnea events, via communication with the ventilation system 3827, and also determine and measure other patient parameters such as respiratory rate or activity level. Using this information, the ventilator 3809 may then synchronize and titrate the therapy to the needs of the patient and to match the gas delivery with the patient's breathing for maximal comfort and therapeutic titration.

An additional sensor 3831 may be used to detect breathing effort. The invention may be used to support the respiration of the patient, including supporting the work of breathing by increasing pressure and volume in the lung, and can be used for maintaining airway patency of the upper airways such as the oropharyngeal airway 3819. When using the invention, the patient breathes normally through their upper airway and through their nose, while receiving mechanical support through the interface. During exhalation, the exhaled gas preferably does not enter the gas delivery circuit but rather exits the nose or mouth directly to ambient air, or through, across or around the nasal interface 3805 to ambient air. The patient can keep their mouth closed during use for example during inspiration, to help direct the mechanical support to the lower airways and around the oral cavity 3833, base of the tongue 3835, palate 3837 and esophagus 3839, or can use a mouth guard or chin band, if necessary. The gas delivery can be delivered cyclically in synchrony with the patient's breath phases, or continuously, or combinations thereof as will be described in subsequent sections. The patient can use the therapy while stationary, while being transported, while mobile and active, or while resting or sleeping. The therapy has homecare, hospital, subacute care, emergency, military, pandemic and transport applications.

Figure 39:
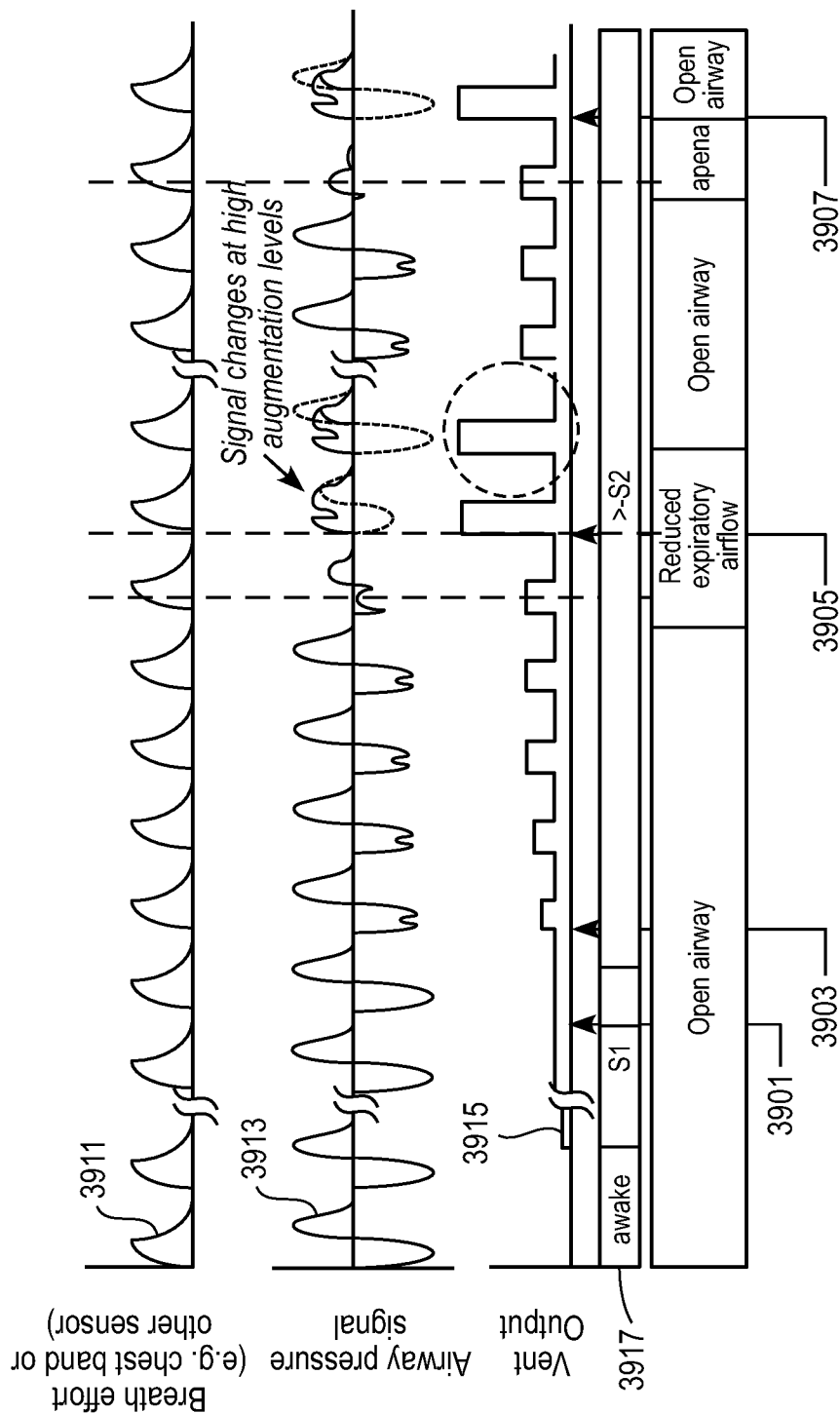
FIG. 39 is a diagram showing the timing and operation of an embodiment of the invention when used to treat sleep apnea, including ramping and biofeedback algorithms.

FIG. 39 graphically describes the timing and operation of the invention when used to treat sleep apnea. The top graph shows the patient's breathing pattern and effort 3911, based on a respiration sensor that measures breathing effort, such as for example a chest impedance band, a neck sensor that measures breath effort by sensing tracheal activity, or other sensors, referred to as A. The middle graph indicates the patient's airway pressure signal as measured by the nasal mask and ventilator of the invention 3913, referred to as B, and the lower graph indicates the ventilator output 3915 at the different stages of sleep in the bar 3917 below the lower graph, and different stages of airway obstruction as indicated in the lower bar. A bias flow is ramped at time 3901, ventilator low output triggering is initiated at time 3903 in response to the signal B and optionally A (amplitude ramps), ventilator therapeutic output triggering is initiated at time 3905 in response to reduced airflow signal detected by B and optionally A, for example one breath after reduced expiratory airflow is detected by B), and ventilator output triggering is initiated in response to an apnea signal B for example one breath after B indicates no breath when a breath was expected, and optionally A simultaneously indicates a breath effort at time 3907.

At the beginning of the sleep session during the awake state, the ventilator gas flow output is off, however the ventilator monitoring functions are on, such as airway pressure monitoring. The patient can freely breathe through the spontaneous breathing apertures in the nasal mask during this stage. Before, when or after the patient enters S1, when the airway may still be open, the ventilator gas output switches to an on state and delivers flow and pressure constantly or intermittently at levels below the therapeutic level to acclimate the patient to the sensation of the therapy. As some time before or after the airway begins to obstruct, such as when reduced expiratory airflow is detected typically in S2, the ventilator gas flow output switches to a cyclical output and ramps to a therapeutic output which is capable of preventing or reversing airway obstruction, and is synchronized with the inspiratory effort of the patient.

Ideally, airway obstructions will thus be prevented for the remainder of the sleep session, however, if an apnea is detected the ventilator output can increase, for example unsynchronized continuous flow can increase, until airflow is detected once again. In addition, the cyclical output can decrease until reduced expiratory airflow is detected, in order to titrate the therapy to lowest possible levels. In addition, delivering non-therapeutic levels of gas earlier in the session also serves to provide information to the system regarding the fit and function of the nasal interface. For example, the breathing pressure signal can be used to ascertain if the interface is attached and aligned properly. If the interface is attached correctly, the system will detect that and proceed normally, but if the interface is not attached or aligned correctly, the system will detect this with signal processing, and can alert the user to make adjustments before the patient enters a deep stage of sleep. Alternatively, the system can provide therapeutic levels of therapy soon after the nasal interface is attached, and determine if the interface is connected properly, and if not, instruct the patient to make the necessary adjustments. Once properly fitted, as determined by the signal processing of the system, the ventilation gas output is turned off until needed, as described in the foregoing.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A system for providing ventilatory support comprising:
a gas source;
a gas delivery circuit;
a nasal interface adapted to allow a patient to breathe ambient air through the nasal interface;
a gas flow path through the nasal interface, wherein the gas flow path comprises a distal end gas flow path opening;
a nozzle positioned on a proximal end of the nasal interface at a distance from the distal end gas flow path opening; and
an entrainment port associated with the nasal interface, wherein at least a portion of the entrainment port is between the nozzle and the distal end gas flow opening,
wherein the nozzle is in fluid communication with the gas delivery circuit and the gas source,
wherein the nozzle delivers gas into the nasal interface to create a negative pressure area in the gas flow path at the entrainment port,
wherein the nasal interface and the nozzle create a positive pressure area between the entrainment port and the distal end gas flow path, and
wherein a combination of gas from the gas source and air entrained through the entrainment port provide ventilatory support.

2. The system of claim 1, wherein the nasal interface includes a sound reducing feature.

3. The system of claim 2, wherein the sound reducing feature is angling the nozzle at an approximately 1-30 degree angle from a manifold gas flow path centerline axis.

4. The system of claim 2, wherein the sound reducing feature is an off-centered nozzle positioned off of the manifold gas flow path centerline by 5-25%.

5. The system of claim 2, wherein the sound reducing feature comprises a secondary gas flow exit that is separate from the entrainment port.

6. The system of claim 1, wherein sound generated by the nasal interface is <50 db at 1 meter.

7. The system of claim 1, wherein the gas flow path comprises a first section that is a lateral-to-midline section and a second section distal to the first section that is a inferior-to-superior section, and a curve between the first section and the second section, with the positive pressure area generated proximal to the curve.

8. The system of claim 1, further comprising a pressure sensing port terminating in the positive pressure area in the gas flow path.

9. The system of claim 1, wherein the gas flow path comprises a left gas flow path and a separate right gas flow path.

10. The system of claim 9, wherein the left gas flow path and the right gas flow path are pneumatically interconnected with an interconnecting channel.

11. The system of claim 1, further comprising a manifold, wherein the manifold is curved with a lateral-posterior-inferior curve on each side of a midline of the manifold to position the manifold where the manifold is most comfortable to the user.

12. The system of claim 1, further comprising a manifold, wherein the manifold includes at least one flex joint, and the at least one flex joint is located at a midline of the manifold.

13. The system of claim 12, wherein the manifold is made of a flexible material.

14. The system of claim 1, further comprising a manifold, and wherein the manifold is made of a malleable material to be shaped to a face of a user.

15. The system of claim 1, further comprising a manifold, and a space adjustment at a center of the manifold.

16. The system of claim 1, further comprising one or more nasal cushions attachable to the distal end gas flow opening, the one or more nasal cushions comprising a snap ring on pillows comprising a hard material, and a mating ring surrounding distal end gas flow openings.

17. The system of claim 1, further comprising one or more nasal cushions attachable to the distal end gas flow opening, the one or more nasal cushions comprising a rotatable connection to the nasal interface.

18. The system of claim 1, wherein a cross-sectional area of the gas flow path does not decrease from the entrainment port to the distal end gas flow opening.

19. The system of claim 1, wherein a cross-sectional area of the gas flow path is uniform from the entrainment port to the distal end gas flow opening.

20. The system of claim 1, wherein a cross-sectional area of the gas flow path increases from the entrainment port to the distal end gas flow opening.

21. The system of claim 1, wherein delivery of gas from the gas source is synchronized with an inspiratory phase.

22. The system of claim 1, wherein a patient spontaneous respiratory rate is determined, and a time of delivery of gas from the gas source is modulated to deliver a set volume at a different time and pressure amplitude based on the patient's spontaneous respiratory rate.

23. The system of claim 1, wherein the gas from the gas source is controlled by a wear-able ventilator.

24. The system of claim 1, wherein ventilatory support comprises reducing work of breathing to treat respiratory insufficiency.

25. The system of claim 1, wherein ventilatory support comprises elevating airway pressure to treat sleep apnea.

26. The system of claim 1, wherein the nozzle and gas delivery tubing is attached to only one side of the nasal interface.

27. The system of claim 1, wherein the gas flow path does not include abrupt angles.

28. The system of claim 27, wherein the abrupt angles are substantially 90 degrees.

29. The system of claim 1, wherein a patient receives approximately 20-200% entrained air relative to gas from the gas source in the combination of gas from the gas source and the air entrained through the entrainment port.

30. The system of claim 1, wherein the nozzle comprises a tip, wherein at least a portion of the entrainment port is between the tip of the nozzle and the distal end gas flow opening.

31. The system of claim 30, wherein the tip of the nozzle is located at a midpoint of the entrainment port.

32. The system of claim 30, wherein the tip of the nozzle is 5-60 mm from a centerline.

33. The system of claim 1, wherein the entertainment port is completely distal to the nozzle.

34. The system of claim 1, wherein the entrainment port has an average cross sectional area of approximately 0.035-0.095 square inches.

35. The system of claim 1, wherein the negative pressure area is within the gas flow path.

36. The system of claim 35, wherein the negative pressure area extends from the entrainment port to a location proximal to the distal end of the nasal interface.

37. The system of claim 1, wherein a negative pressure is less than ambient.

38. The system of claim 37, wherein the negative pressure is approximately $-5$ to $-40$ cmH$_2$O.

39. The system of claim 1, wherein the positive pressure area is within the gas flow path.

40. The system of claim 39, wherein the positive pressure area extends within the gas flow path from a location distal to the entrainment port the distal end of the nasal interface.

41. The system of claim 1, wherein the positive pressure is greater than ambient.

42. The system of claim 41, wherein the positive pressure is 0.01 to 0.50 psi.

43. The system of claim 1, wherein the combination of gas from the gas source and the air entrained through the entrainment port increase upper airway pressure by 2-35 cwp.

44. The system of claim 1, wherein the combination of gas from the gas source and the air entrained through the entrainment port exits the nasal interface as laminar flow.

45. The system of claim 1, wherein the nasal interface has throat length of approximately $-0.75$ to 2.0 inches.

46. The system of claim 1, wherein the gas delivery circuit has an inner diameter of less than 4 mm.

47. The system of claim 1, further comprising at least one sensor for measuring phases of breathing.

48. The system of claim 1, further comprising a ventilator, wherein the ventilator comprises a control unit, and wherein the control unit adjusts an output of the ventilator to match a patient's ventilation needs based on information from the at least one sensor.

49. A system for increasing airway pressure, comprising:
a gas source;
a gas delivery circuit;
a nasal interface adapted to allow a patient to breathe ambient air through the nasal interface;
a gas flow path through the nasal interface, wherein the gas flow path comprises a distal end gas flow path opening;
a nozzle positioned on a proximal end of the nasal interface at a distance from the distal end gas flow path opening; and
wherein the nozzle is in fluid communication with the gas delivery circuit and the gas source,
wherein the nozzle delivers gas into the nasal interface to create a negative pressure area in the gas flow path near the proximal end of the nasal interface,
wherein the nasal interface and the nozzle create a positive pressure area within the gas flow path distal to the negative pressure area, and
wherein a combination of gas from the gas source and air entrained in the gas flow path increases airway pressure.

50. The system of claim 49, further comprising an entrainment port associated with the nasal interface, wherein at least a portion of the entrainment port is between the nozzle and the distal end gas flow opening.

51. The system of claim 50, wherein the negative pressure area extends from the entrainment port to a location proximal to the distal end of the nasal interface.

52. The system of claim 49, wherein a negative pressure is less than ambient.

53. The system of claim 52, wherein the negative pressure is $-10$ to $-50$ cmH$_2$O.

54. The system of claim 49, wherein the positive pressure is greater than ambient.

55. The system of claim 54, wherein the positive pressure is 2-30 cmH$_2$O.

56. A nasal interface for treating sleep apnea comprising a tubular body with a distal end and proximal end and a gas flow path extending from the distal end to the proximal end, wherein the tubular body curves laterally from a nostril distal end to the proximal end, and comprises:
a. a distal end configured to impinge a nostril airway;
b. an ambient air entrainment aperture in the tubular body between the proximal end and the distal end adapted to permit spontaneous breathing of ambient air directly through the ambient air entrainment aperture without impeding a user's breathing;
c. a jet nozzle port positioned proximal to the ambient air entrainment aperture at the proximal end of the tubular body, and adapted to direct gas into the gas flow path and entrain air in from the ambient air entrainment aperture; and
d. a pressure sensing port,
wherein gas is configured to be delivered to a patient airway from a combination of the gas directed from the jet nozzle port and air entrained through the ambient air entrainment aperture, and wherein substantially all the gas exiting the user exits out of the ambient air entrainment aperture.

57. The nasal interface of claim 56, wherein the gas flow path comprises a length between the nozzle and distal end allowing a velocity profile exiting the jet nozzle port to merge with the walls of the gas flow path, and develop a positive pressure at a location proximal to the distal end and outside the nostril.

58. The nasal interface of claim 56, wherein the gas flow path has a minimum cross sectional area greater than or equal to a cross sectional area of the ambient air entrainment aperture.

59. The nasal interface of claim 56, wherein the ambient air entrainment aperture is positioned at an anterior side of the tubular body, to entrain airflow into the ambient air entrainment aperture from in front of a patient's face, and to direct exhaled gas flowing out of the aperture away from the patient's face.

60. The nasal interface of claim 56, wherein the tubular body includes a sound reducing feature selected from a group of: a secondary port near the distal end, a nozzle position that is off-centered from the centerline axis of the tubular body, a nozzle angle that directs gas into the wall of the tubular body.

61. The nasal interface of claim 56, wherein the tubular body includes an internal volume of less than 0.40 cubic inches.

62. The nasal interface of claim 56, wherein the tubular body includes a gas flow resistance of less than 4 cmH2O pressure at 60 lpm gas flow.

63. The nasal interface of claim 56, wherein the pressure sensing port is positioned in the positive pressure area of the tubular body.

64. The nasal interface of claim 56, further comprising a left and a right tubular body, wherein each tubular body comprises a pressure sensing port.

65. The nasal interface of claim 56, further comprising an entrainment pressure sensing port located near the ambient air entrainment aperture, and a pressure sensing port located near the distal end.

* * * * *